(12) United States Patent
Chen et al.

(10) Patent No.: US 11,524,958 B2
(45) Date of Patent: Dec. 13, 2022

(54) TRICYCLIC COMPOUND AS CRTH2 INHIBITOR

(71) Applicant: CHIA TAI TIANQING PHARMACEUTICAL GROUP CO., LTD., Lianyungang (CN)

(72) Inventors: Bin Chen, Shanghai (CN); Yuanshan Yao, Shanghai (CN); Yuan Chen, Shanghai (CN); Ao Li, Shanghai (CN); Ran Xu, Shanghai (CN); Zhensheng Huang, Shanghai (CN); Dongdong Tian, Shanghai (CN); Hongwei Li, Shanghai (CN); Chengshuai Yang, Shanghai (CN); Jian Li, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 936 days.

(21) Appl. No.: 16/318,298

(22) PCT Filed: Jul. 21, 2017

(86) PCT No.: PCT/CN2017/093850
§ 371 (c)(1),
(2) Date: Jan. 16, 2019

(87) PCT Pub. No.: WO2018/014867
PCT Pub. Date: Jan. 25, 2018

(65) Prior Publication Data
US 2021/0403466 A1   Dec. 30, 2021

(30) Foreign Application Priority Data
Jul. 21, 2016 (CN) .......................... 201610581810.X

(51) Int. Cl.
C07D 471/04   (2006.01)
(52) U.S. Cl.
CPC .................. *C07D 471/04* (2013.01)
(58) Field of Classification Search
None
See application file for complete search history.

(56) References Cited

U.S. PATENT DOCUMENTS 7,144,913 B2 * 12/2006 Wang ...................... A61P 11/06
514/411

FOREIGN PATENT DOCUMENTS

| CN | 101189011 A | 5/2008 |
|---|---|---|
| WO | 2002/094830 A2 | 11/2002 |
| WO | 2006/052798 A2 | 3/2006 |
| WO | 2006/026273 A2 | 5/2006 |
| WO | 2006/089309 A2 | 8/2006 |

OTHER PUBLICATIONS

International Search Report in PCT/CN2017/093850, dated Oct. 10, 2017.
Beaulieu, et al. "Identification of prostaglandin D 2 receptor antagonists based on a tetrahydropyridoindole scaffold." Bioorganic & medicinal chemistry letters 18, No. 8 (2008): 2696-2700.

* cited by examiner

*Primary Examiner* — Po-Chih Chen
(74) *Attorney, Agent, or Firm* — Kilpatrick Townsend & Stockton LLP

(57) ABSTRACT

Provided are a tricyclic compound as shown in formula (I) as a CRTH2 inhibitor, or a pharmaceutically acceptable salt, a tautomer, a stereoisomer or a solvate thereof, and the use thereof in treating diseases related to CRTH2 receptors.

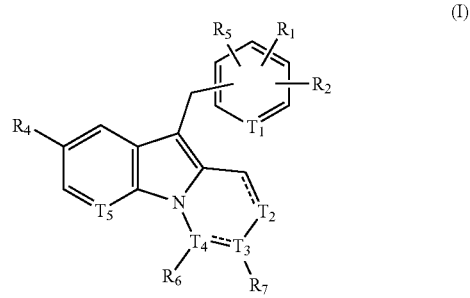

(I)

15 Claims, No Drawings

TRICYCLIC COMPOUND AS CRTH2 INHIBITOR

CROSS-REFERENCES TO RELATED APPLICATIONS

The present application is a U.S. National Phase of PCT/CN2017/093850, International Filing Date Jul. 21, 2017, which claims the benefit of Chinese Patent Application No. 201610581810.X filed at the China National Intellectual Property Administration on Jul. 21, 2016, the disclosures of which are incorporated in their entirety herein by reference.

TECHNICAL FIELD

The present application relates to a fused tricyclic compound as a CRTH2 inhibitor and use thereof in the treatment of a disease associated with a CRTH2 receptor.

BACKGROUND

CRTH2 (DP2 or GPR44) is a G protein-coupled receptor. After combined with prostaglandin (PGD2), it is involved in the activation and chemotaxis of Th2 lymphocytes, eosinophils and basophils, inhibits the apoptosis of Th2 lymphocytes, and stimulates the production of IL4, IL5 and IL13. These interleukins are involved in important biological responses, including eosinophil recruitment and survival, mucus secretion, airway hyperresponsiveness, and immunoglobulin E (IgE) production.

Ramatroban is a TP (thromboxane-type prostanoid) receptor antagonist, triggering extremely strong vascular and bronchial smooth muscle contraction, and platelet activation. Ramatroban is a weak CRTh2 receptor antagonist. Ramatroban has been approved in Japan for treating allergic rhinitis.

WO2005044260 has reported Compound OC459; and WO2005123731 has reported Compound QAW-039.

Ramatroban

OC459

QAW-039

SUMMARY OF THE INVENTION

In one aspect, the present application provides a compound represented by formula (I), or a pharmaceutically acceptable salt, tautomer, stereoisomer, or solvate thereof, (I)

wherein
$T_1$ is selected from the group consisting of N and CH;
$T_2$ is selected from the group consisting of a single bond, N, NH, $CH_2$, and CH;
$T_3$ and $T_4$ are each independently selected from the group consisting of C, $CR_3$, and N;
$T_5$ is selected from the group consisting of N and CH;
$R_1$ and $R_2$ are each independently selected from the group consisting of H, F, Cl, Br, I, —OH, and —$NH_2$; or are each independently selected from the following groups: $C_{1-6}$ alkyl, $C_{1-3}$ alkyl-S(=O)$_2$—, $C_{1-3}$ alkyl-S(=O)—, $C_{1-3}$ alkyl-C(=O)—, phenyl, 5- to 6-membered heteroaryl, phenyl-$L_1$-, and 5- to 6-membered heteroaryl-$L_1$-, which are optionally substituted with 1, 2, or 3 R; or
$R_1$ and $R_2$ together with the ring-forming atoms they are attached to form a 5- to 6-membered ring, which is optionally substituted with 1, 2, or 3 R;
$L_1$ is selected from the group consisting of —S(=O)$_2$—, —S(=O)—, —C(=O)O—, —C(=O)—, and —C(=O)NH—;
one of $R_6$ and $R_7$ is -L-COOH, and the other is selected from the group consisting of H and $C_{1-3}$ alkyl optionally substituted with 1, 2, or 3 R;
L is selected from the group consisting of a single bond and —$CH_2$—;
each $R_3$ is independently selected from the group consisting of H and $C_{1-3}$ alkyl optionally substituted with 1, 2, or 3 R;
$R_4$ is selected from the group consisting of H, halogen, —OH, and —$NH_2$; or is selected from the following groups: $C_{1-3}$ alkyl and $C_{1-3}$ alkoxy, which are optionally substituted with 1, 2, or 3 R;

$R_5$ is selected from the group consisting of H and the following groups: $C_{1-3}$ alkyl and $C_{1-3}$ alkoxy, which are optionally substituted with 1, 2, or 3 R;

each R is independently selected from the group consisting of F, Cl, Br, I, —CN, —OH, and —COOH; or is independently selected from the following groups: —NH$_2$, $C_{1-6}$ alkyl, $C_{3-6}$ cycloalkyl, 3- to 6-membered heterocycloalkyl, phenyl, and 5- to 6-membered heteroaryl, which are optionally substituted with 1, 2, or 3 R'; and each R' is independently selected from the group consisting of F, Cl, Br, I, —OH, —CN, —NH$_2$, —COOH, Me, Et, —CF$_3$, —CHF$_2$, —CH$_2$F, —NHCH$_3$, and —N(CH$_3$)$_2$.

In another aspect, the present application provides a pharmaceutical composition, comprising a compound represented by formula (I) of the present application, or a pharmaceutically acceptable salt thereof, or a tautomer thereof, or a stereoisomer thereof, or a solvate thereof, and a pharmaceutically acceptable adjuvant.

In another aspect, the present application provides a method for treating a disease mediated by a CRTH2 receptor in a mammal, comprising administering to a mammal, preferably a human, in need thereof a therapeutically effective amount of a compound represented by formula (I), or a pharmaceutically acceptable salt thereof, or a tautomer thereof, or a stereoisomer thereof, or a solvate thereof, or a pharmaceutical composition thereof.

In still another aspect, the present application relates to use of a compound represented by formula (I), or a pharmaceutically acceptable salt thereof, or a tautomer thereof, or a stereoisomer thereof, or a solvate thereof, or a pharmaceutical composition thereof in the preparation of a medicament for preventing or treating a disease mediated by a CRTH2 receptor.

In yet another aspect, the present application relates to a compound represented by formula (I), or a pharmaceutically acceptable salt thereof, or a tautomer thereof, or a stereoisomer thereof, or a solvate thereof, or a pharmaceutical composition thereof for use in preventing or treating a disease mediated by a CRTH2 receptor.

DETAILED DESCRIPTION OF THE INVENTION

In the following description, certain specific details are included to provide a thorough understanding of various disclosed embodiments. However, those skilled in the relevant art will recognize that the embodiments may be practiced without one or more of these specific details, but with other methods, components, materials, and the like.

Unless the context requires otherwise, throughout the specification and the claims thereafter, the word "comprise" and English variations thereof, such as "comprises" and "comprising", should be construed in an open, inclusive sense, that is, as "including, but not limited to".

Reference throughout this specification to "one embodiment", or "an embodiment", or "another embodiment", or "some embodiments" means that a particular referent element, structure, or characteristic described in connection with the embodiment is included in at least one embodiment. Accordingly, the phase "in one embodiment", or "in an embodiment", or "in another embodiment", or "in some embodiments" that appears in various places throughout this specification are not necessarily all referring to the same embodiment. In addition, the particular elements, structures, or characteristics may be combined in any suitable manner in one or more embodiments.

It should be understood that, as used in this specification and the appended claims, the singular forms "a", "an" and "the" include plural referents unless the context clearly dictates otherwise. Accordingly, for example, reference to a reaction in which "a catalyst" is involved includes a single catalyst, or two or more catalysts. It should also be understood that the term "or" is generally used in its sense including "and/or", unless the context clearly dictates otherwise.

The present application provides a compound represented by formula (I), or a pharmaceutically acceptable salt, tautomer, stereoisomer, or solvate thereof,

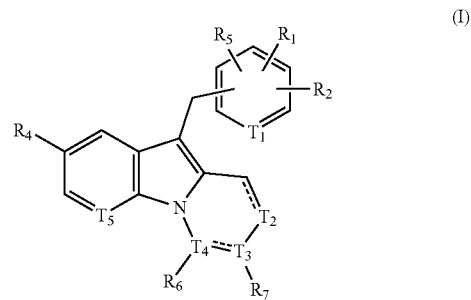

(I)

wherein $T_1$ is selected from the group consisting of N and CH;

$T_2$ is selected from the group consisting of a single bond, N, NH, CH$_2$, and CH;

$T_3$ and $T_4$ are each independently selected from the group consisting of C, CR$_3$, and N;

$T_5$ is selected from the group consisting of N and CH;

$R_1$ and $R_2$ are each independently selected from the group consisting of H, F, Cl, Br, I, —OH, and —NH$_2$; or are each independently selected from the following groups: $C_{1-6}$ alkyl, $C_{1-3}$ alkyl-S(═O)$_2$—, $C_{1-3}$ alkyl-S(═O)—, $C_{1-3}$ alkyl-C(═O)—, phenyl, 5- to 6-membered heteroaryl, phenyl-L$_1$-, and 5- to 6-membered heteroaryl-L$_1$-, which are optionally substituted with 1, 2, or 3 R; or $R_1$ and $R_2$ together with the ring-forming atoms they are attached to form a 5- to 6-membered ring, which is optionally substituted with 1, 2, or 3 R;

L$_1$ is selected from the group consisting of —S(═O)$_2$—, —S(═O)—, —C(═O)O—, —C(═O)—, and —C(═O)NH—;

one of R$_6$ and R$_7$ is -L-COOH, and the other is selected from the group consisting of H and $C_{1-3}$ alkyl optionally substituted with 1, 2, or 3 R;

L$_1$ is selected from the group consisting of a single bond and —CH$_2$—;

each R$_3$ is independently selected from the group consisting of H and $C_{1-3}$ alkyl optionally substituted with 1, 2, or 3 R;

R$_4$ is selected from the group consisting of H, halogen, —OH, and —NH$_2$; or is selected from the following groups: $C_{1-3}$ alkyl and $C_{1-3}$ alkoxy, which are optionally substituted with 1, 2, or 3 R;

R$_5$ is selected from the group consisting of H and the following groups: $C_{1-3}$ alkyl and $C_{1-3}$ alkoxy, which are optionally substituted with 1, 2, or 3 R;

each R is independently selected from the group consisting of F, Cl, Br, I, —CN, —OH, and —COOH; or is independently selected from the following groups: —NH$_2$, $C_{1-6}$ alkyl, $C_{3-6}$ cycloalkyl, 3- to 6-membered heterocycloalkyl, phenyl, and 5- to 6-membered heteroaryl, which are optionally substituted with 1, 2, or 3 R'; and each R' is independently selected from the group consisting of F, Cl, Br, I, —OH, —CN, —NH$_2$, —COOH, Me, Et, —CF$_3$, —CHF$_2$, —CH$_2$F, —NHCH$_3$, and —N(CH$_3$)$_2$.

In some embodiments of the present application, each R is independently selected from the group consisting of F, Cl, Br, I, —CN, —OH, and —COOH; or is independently selected from the group consisting of —NH$_2$ and C$_{1-4}$ alkyl, which are optionally substituted with 1, 2, or 3 R'.

In some embodiments of the present application, each R is independently selected from the group consisting of F, Cl, Br, I, —CN, —OH, —NH$_2$, —COOH, Me, Et, —CF$_3$, —CHF$_2$, —CH$_2$F, —NHCH$_3$, —N(CH$_3$)$_2$,

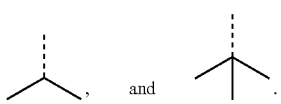

In some embodiments of the present application, R$_1$ and R$_2$ are each independently selected from the group consisting of H, F, Cl, Br, I, —OH, and —NH$_2$; or are each independently selected from the following groups: C$_{1-3}$ alkyl, C$_{1-3}$ alkyl-S(═O)$_2$—, C$_{1-3}$ alkyl-S(═O)—, C$_{1-3}$ alkyl-C(═O)—, phenyl-L$_1$-, and 5- to 6-membered heteroaryl-L$_1$-, which are optionally substituted with 1, 2, or 3 R.

In some embodiments of the present application, R$_1$ and R$_2$ are each independently selected from the group consisting of H, F, Cl, Br, I, —OH, and —NH$_2$; or are each independently selected from the following groups: C$_{1-3}$ alkyl, C$_{1-3}$ alkyl-S(═O)$_2$—, C$_{1-3}$ alkyl-S(═O)—, C$_{1-3}$ alkyl-C(═O)—, phenyl-L$_1$-, pyridinyl-L$_1$-, and pyrimidyl-L$_1$-, which are optionally substituted with 1, 2, or 3 R.

In some embodiments of the present application, R$_1$ and R$_2$ are each independently selected from the group consisting of H, F, Cl, Br, I, —OH, and —NH$_2$; or are each independently selected from the following groups: Me, Et,

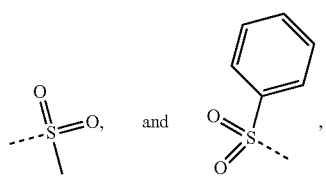

which are optionally substituted with 1, 2, or 3 R.

In some embodiments of the present application, R$_1$ and R$_2$ are each independently selected from the group consisting of H, F, Cl, Br, I, —OH, —NH$_2$, Me, —CF$_3$, Et,

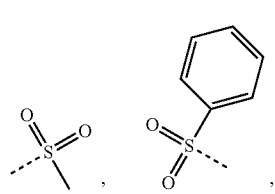

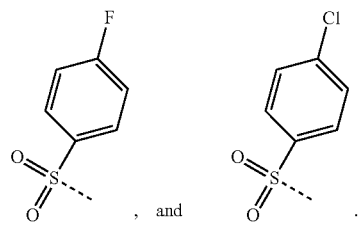

In some embodiments of the present application, L$_1$ is —S(═O)$_2$—.

In some embodiments of the present application, R$_5$ is selected from the group consisting of H, —CF$_3$, and MeO;

In some embodiments of the present application, the structural unit

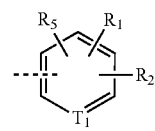

is selected from the group consisting of:

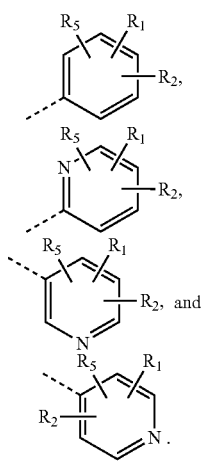

In some embodiments of the present application, the structural unit

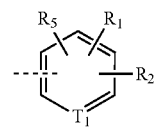

is selected from the group consisting of:

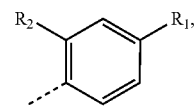

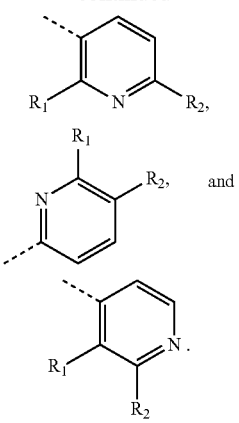
In some embodiments of the present application, the structural unit
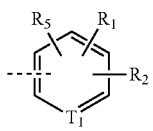
is selected from the group consisting of:
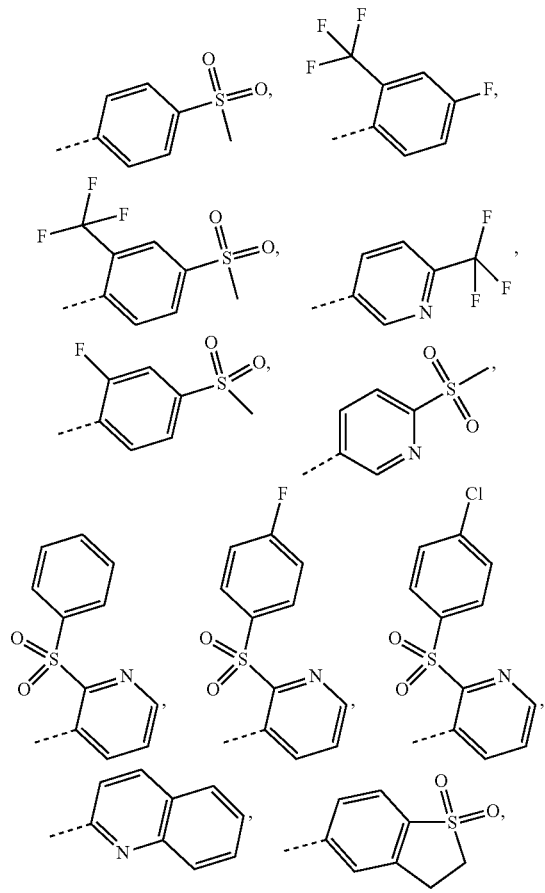
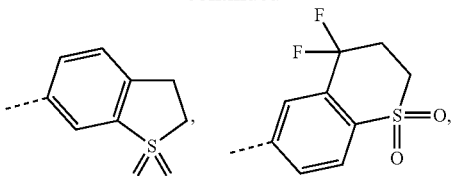
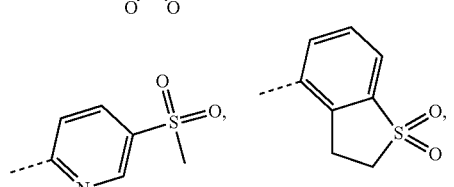
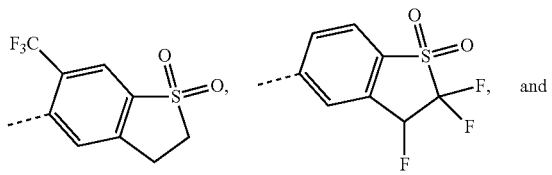
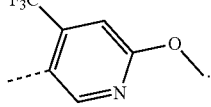
In some embodiments of the present application, the structural unit
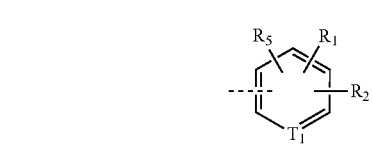
is selected from the group consisting of:
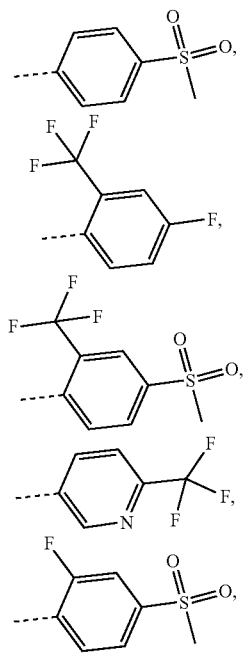

-continued

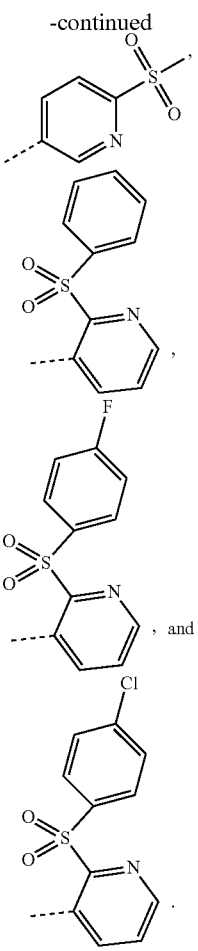, and

In some embodiments of the present application, $R_1$ and $R_2$ together with the ring-forming atoms they are attached to form a benzene ring, a cyclobutyl sulfone ring, or a cyclopentyl sulfone ring, which are optionally substituted with 1, 2, or 3 R.

In some embodiments of the present application, when $R_1$ and $R_2$ together with the ring-forming atoms they are attached to form a 5- to 6-membered ring, the structural unit

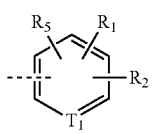

is selected from the group consisting of:

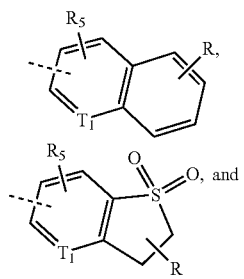

-continued

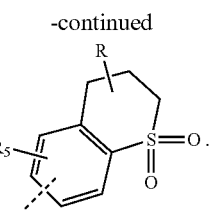

In some embodiments of the present application, when $R_1$ and $R_2$ together with the ring-forming atoms they are attached to form a 5- to 6-membered ring, the structural unit

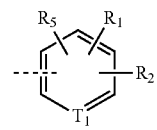

is selected from the group consisting of:

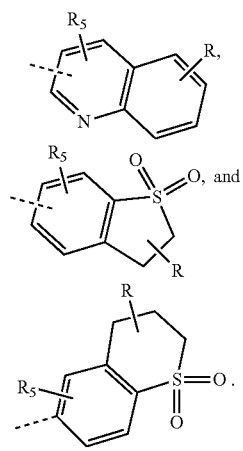

In some embodiments of the present application, when $R_1$ and $R_2$ together with the ring-forming atoms they are attached to form a 5- to 6-membered ring, the structural unit

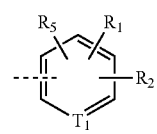

is selected from the group consisting of:

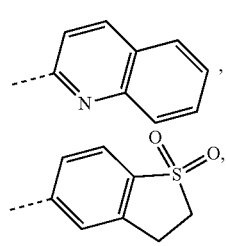

-continued

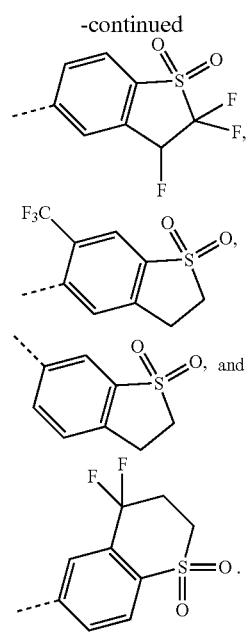

In some embodiments of the present application, when $R_1$ and $R_2$ together with the ring-forming atoms they are attached to form a 5- to 6-membered ring, the structural unit

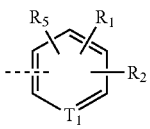

is selected from the group consisting of:

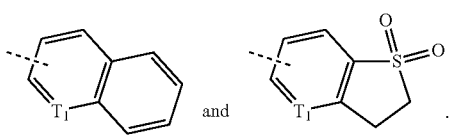

In some embodiments of the present application, when $R_1$ and $R_2$ together with the ring-forming atoms they are attached to form a 5- to 6-membered ring, the structural unit

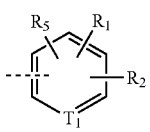

is selected from the group consisting of:

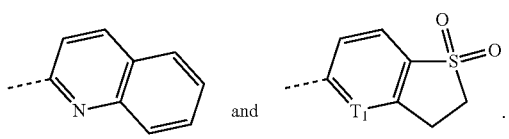

In some embodiments of the present application, each $R_3$ is independently selected from the group consisting of H and Me.

In some embodiments of the present application, $R_4$ is selected from the group consisting of H, F, Cl, Br, I, —OH, —NH$_2$, methoxy, and difluoromethoxy.

In some embodiments of the present application, $R_4$ is selected from the group consisting of H, F, Cl, Br, I, —OH, and —NH$_2$.

In some embodiments of the present application, the compound represented by formula (I) is selected from a compound represented by formula (II)

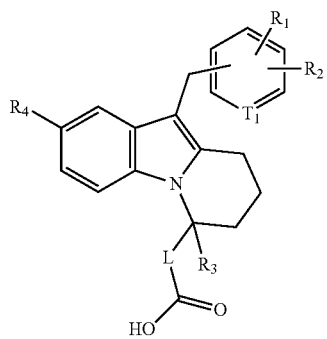

(II)

wherein $R_1$, $R_2$, $R_3$, $R_4$, L, and $T_1$ are defined as in formula (I).

In some embodiments of the present application, the compound represented by formula (I) is selected from a compound represented by formula (III)

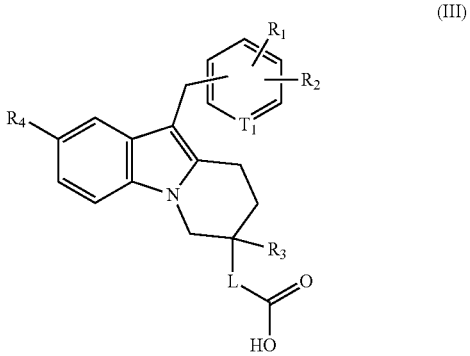

(III)

wherein $R_1$, $R_2$, $R_3$, $R_4$, L, and $T_1$ are defined as in formula (I).

In some embodiments of the present application, the compound represented by formula (I) is selected from a compound represented by formula (IV)

(IV)

wherein $R_1$, $R_2$, $R_4$, L, and $T_1$ are defined as in formula (I).

In another aspect, the present application provides a compound represented by formula (V), a pharmaceutically acceptable salt thereof, and a tautomer thereof, (V)

wherein $T_{11}$ is selected from the group consisting of N and CH;

$T_{21}$ is selected from the group consisting of N, NH, $CH_2$, and CH;

L is selected from the group consisting of a single bond and —$CH_2$—;

$R_{11}$ and $R_{21}$ are each independently selected from the group consisting of H, F, Cl, Br, I, —OH, and —$NH_2$; or are each independently selected from the following groups: $C_{1-6}$ alkyl, $C_{1-6}$ heteroalkyl, phenyl, 5- to 6-membered heteroaryl, phenyl-$L_1$-, and 5- to 6-membered heteroaryl-$L_1$-, which are optionally substituted with 1, 2, or 3 $R_8$;

$L_1$ is selected from the group consisting of —S(=O)$_2$—, —S(=O)—, —C(=O)O—, —C(=O)—, and —C(=O)NH—; or $R_{11}$ and $R_{21}$ are attached to each other to form a 5- to 6-membered ring, which is optionally substituted with 1, 2, or 3 $R_8$;

$R_{31}$ is selected from the group consisting of H and $C_{1-3}$ alkyl optionally substituted with 1, 2, or 3 $R_8$;

$R_{41}$ is selected from the group consisting of H, halogen, —OH, and —$NH_2$; or is selected from the following groups: $C_{1-3}$ alkyl and $C_{1-3}$ heteroalkyl, which are optionally substituted with 1, 2, or 3 $R_8$;

$R_8$ is selected from the group consisting of H, F, Cl, Br, I, —CN, —OH, —$NH_2$, and —COOH; or is selected from the group consisting of $C_{1-6}$ alkyl, $C_{1-6}$ heteroalkyl, $C_{3-6}$ cycloalkyl, 3- to 6-membered heterocycloalkyl, phenyl, and 5- to 6-membered heteroaryl, which are optionally substituted with 1, 2, or 3 $R_8$';

$R_8$' is selected from the group consisting of F, Cl, Br, I, —OH, —CN, —$NH_2$, —COOH, Me, Et, —$CF_3$, —$CHF_2$, —$CH_2F$, —$NHCH_3$, and —$N(CH_3)_2$;

The term "hetero" represents a heteroatom or a heteroatom group selected from the group consisting of —C(=O)NH—, —NH—, =N—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$—, and —NHC(=O)NH—; and the number of the heteroatom or heteroatom group is each independently selected from the group consisting of 1, 2, and 3.

In some embodiments of the present application, in the compound represented by formula (V), $R_8$ is selected from the group consisting of H, F, Cl, Br, I, —CN, —OH, —$NH_2$, and —COOH, or is selected from $C_{1-4}$ alkyl optionally substituted with 1, 2, or 3 $R_8$'.

In some embodiments of the present application, in the compound represented by formula (V), $R_8$ is selected from the group consisting of H, F, Cl, Br, I, —CN, —OH, —$NH_2$, —COOH, Me, Et, —$CF_3$, —$CHF_2$, —$CH_2F$, —$NHCH_3$, —$N(CH_3)_2$, , and .

In some embodiments of the present application, in the compound represented by formula (V), $R_{11}$ and $R_{21}$ are each independently selected from the group consisting of H, F, Cl, Br, I, —OH, and —$NH_2$; or are each independently selected from the following groups: $C_{1-3}$ alkyl, $C_{1-3}$ heteroalkyl, phenyl-$L_1$-, and 5- to 6-membered heteroaryl-$L_1$-, which are optionally substituted with 1, 2, or 3 $R_8$.

In some embodiments of the present application, in the compound represented by formula (V), $R_{11}$ and $R_{21}$ are each independently selected from the group consisting of H, F, Cl, Br, I, —OH, and —$NH_2$; or are each independently selected from the following groups: $C_{1-3}$ alkyl, $C_{1-3}$ alkyl-S(=O)$_2$—, $C_{1-3}$ alkyl-S(=O)—, $C_{1-3}$ alkyl-C(=O)—, pyridinyl-$L_1$-, and pyrimidyl-$L_1$-, which are optionally substituted with 1, 2, or 3 $R_8$.

In some embodiments of the present application, in the compound represented by formula (V), $R_{11}$ and $R_{21}$ are each independently selected from the group consisting of H, F, Cl, Br, I, —OH, and —$NH_2$; or are each independently selected from the following groups: Me, Et, , and , which are optionally substituted with 1, 2, or 3 $R_8$.

In some embodiments of the present application, in the compound represented by formula (V), $R_{11}$ and $R_{21}$ are each independently selected from the group consisting of H, F, Cl, Br, I, —OH, —$NH_2$, Me, —$CF_3$, Et,

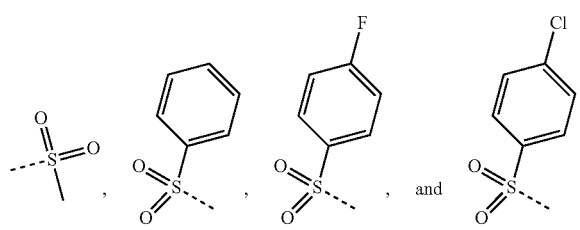

In some embodiments of the present application, in the compound represented by formula (V), the structural unit

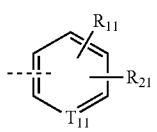

is selected from the group consisting of:

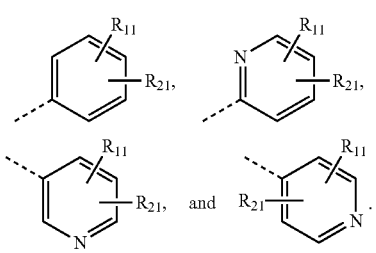

In some embodiments of the present application, in the compound represented by formula (V), the structural unit

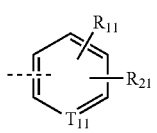

is selected from the group consisting of:

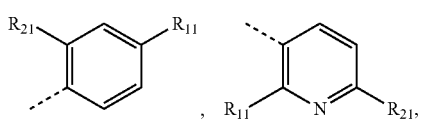

In some embodiments of the present application, in the compound represented by formula (V), the structural unit

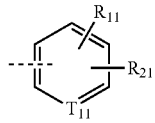

is selected from the group consisting of:

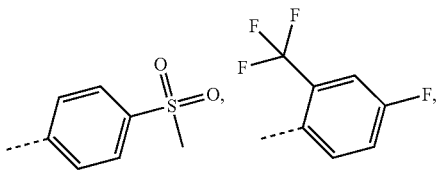

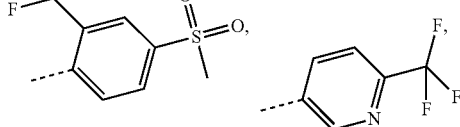

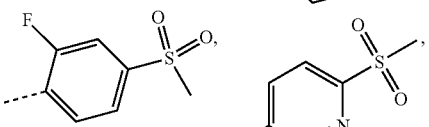

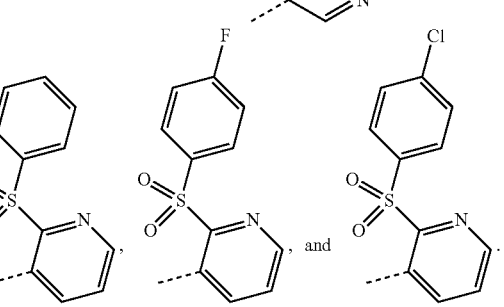

In some embodiments of the present application, in the compound represented by formula (V), $R_{11}$ and $R_{21}$ are attached to each other to form a benzene ring or a cyclobutyl sulfone ring, which are optionally substituted with 1, 2, or 3 $R_8$.

In some embodiments of the present application, in the compound represented by formula (V), when $R_{11}$ and $R_{21}$ are attached to each other, the structural unit

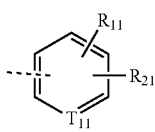

is selected from the group consisting of:

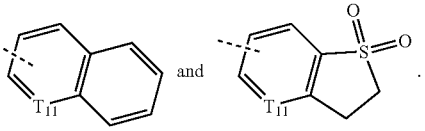

In some embodiments of the present application, in the compound represented by formula (V), when $R_{11}$ and $R_{21}$ are attached to each other, the structural unit

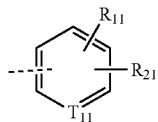

is selected from the group consisting of:

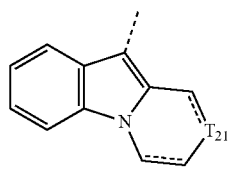

In some embodiments of the present application, in the compound represented by formula (V), $R_{31}$ is selected from the group consisting of H and Me.

In some embodiments of the present application, in the compound represented by formula (V), $R_{41}$ is selected from the group consisting of H, F, Cl, Br, I, —OH, and —NH$_2$.

In some embodiments of the present application, in the compound represented by formula (V), the structural unit

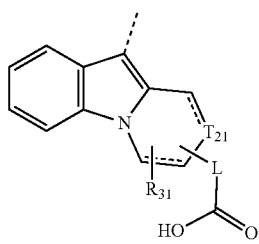

is selected from the group consisting of:

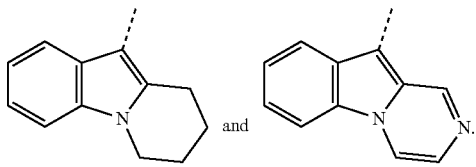

In some embodiments of the present application, in the compound represented by formula (V), the structural unit

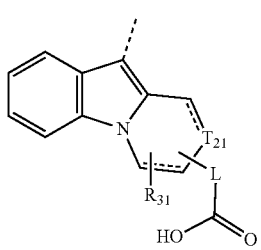

is selected from the group consisting of:

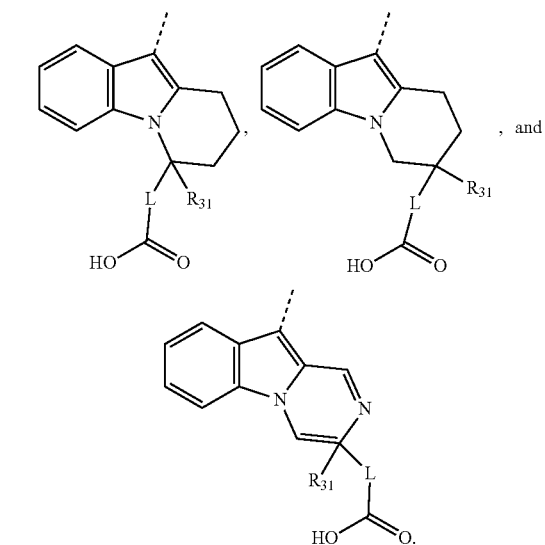

In some embodiments of the present application, in the compound represented by formula (V), the structural unit

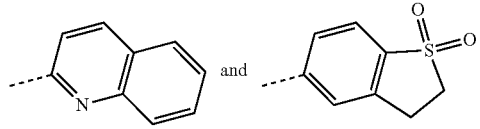

is selected from the group consisting of:

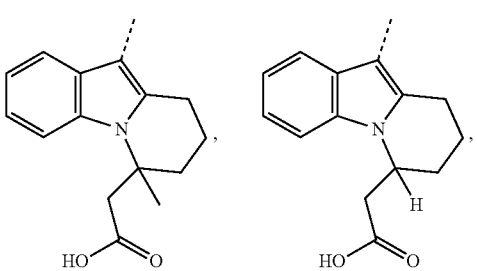

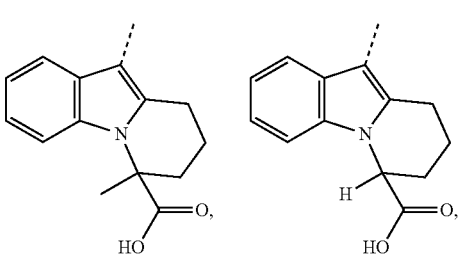

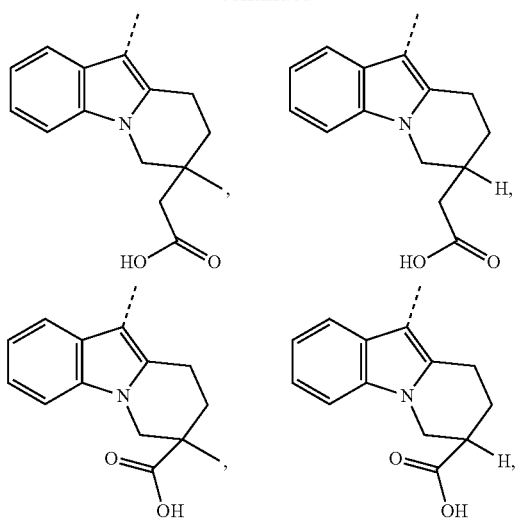
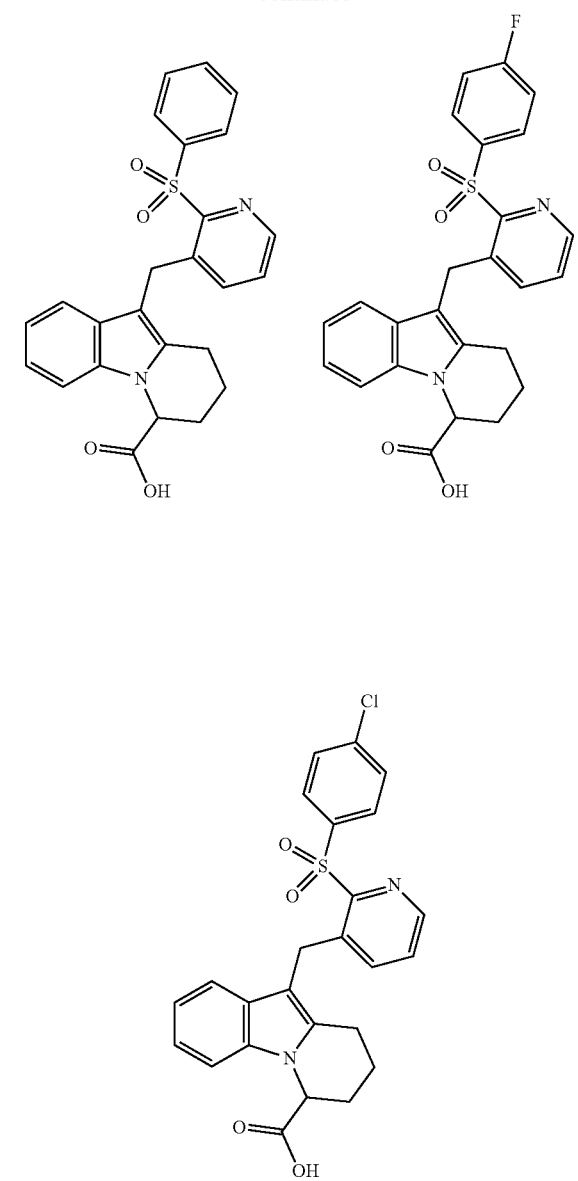
In some embodiments of the present application, the compound represented by formula (I) is selected from the group consisting of:
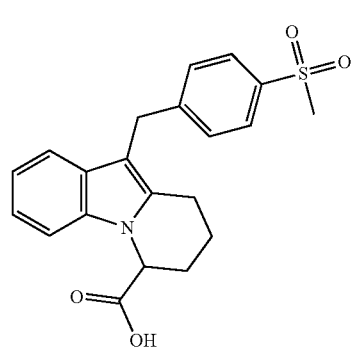
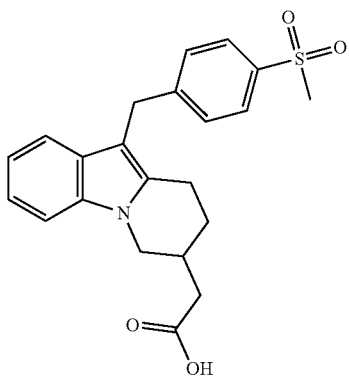

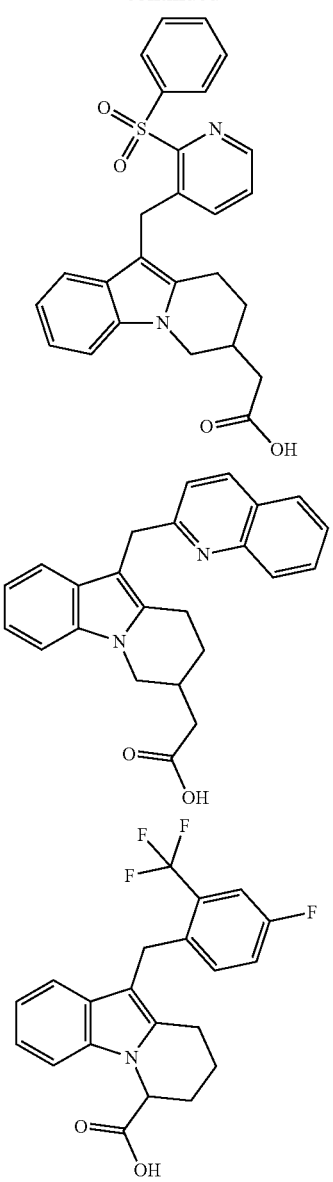
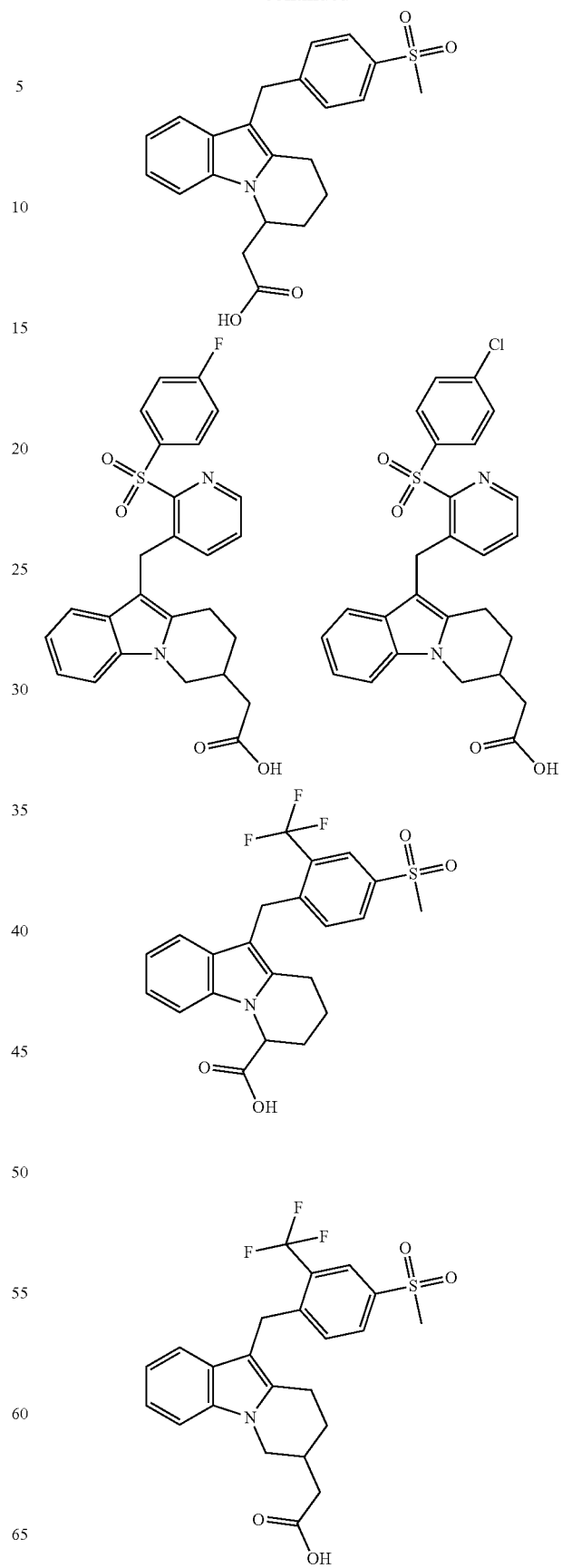

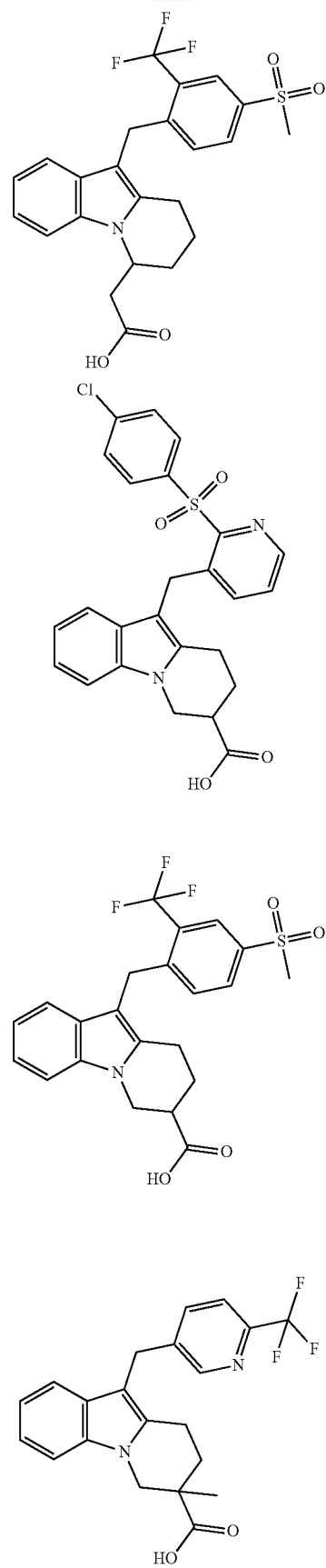
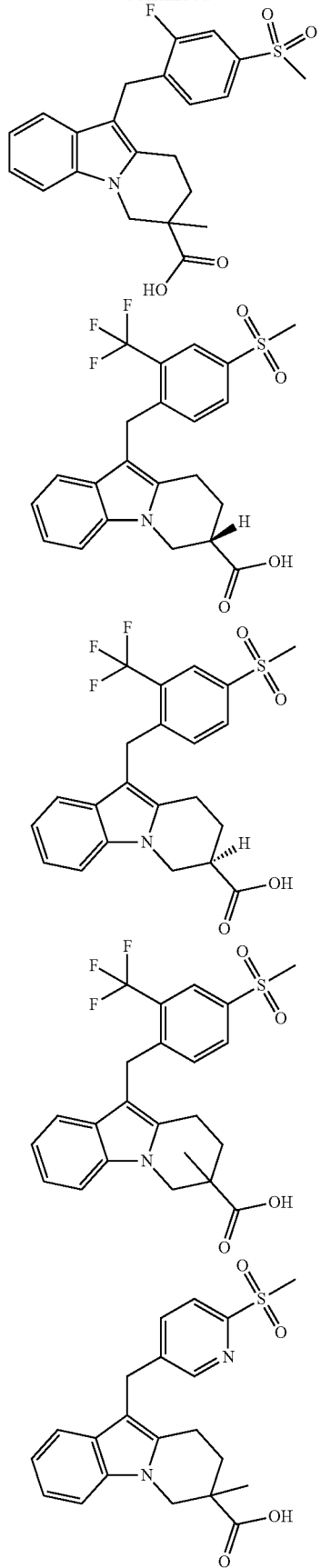

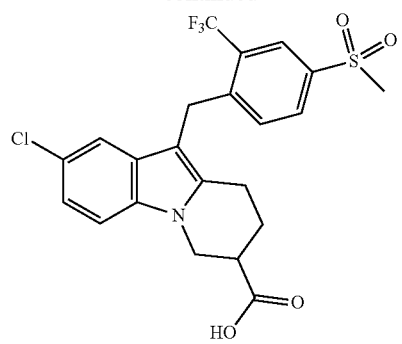
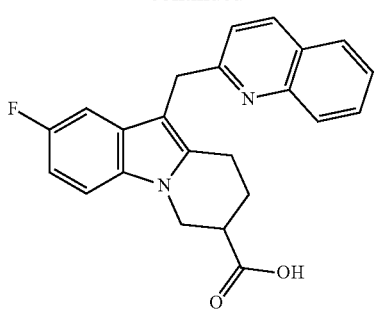
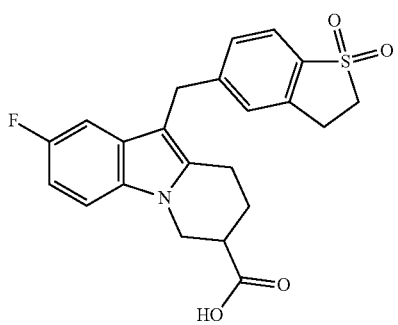
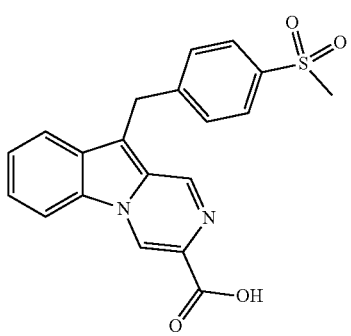
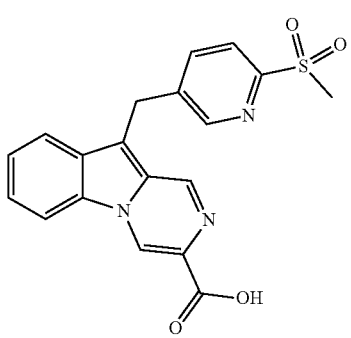
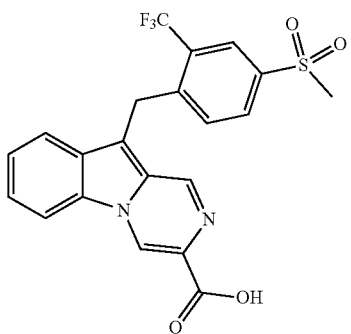

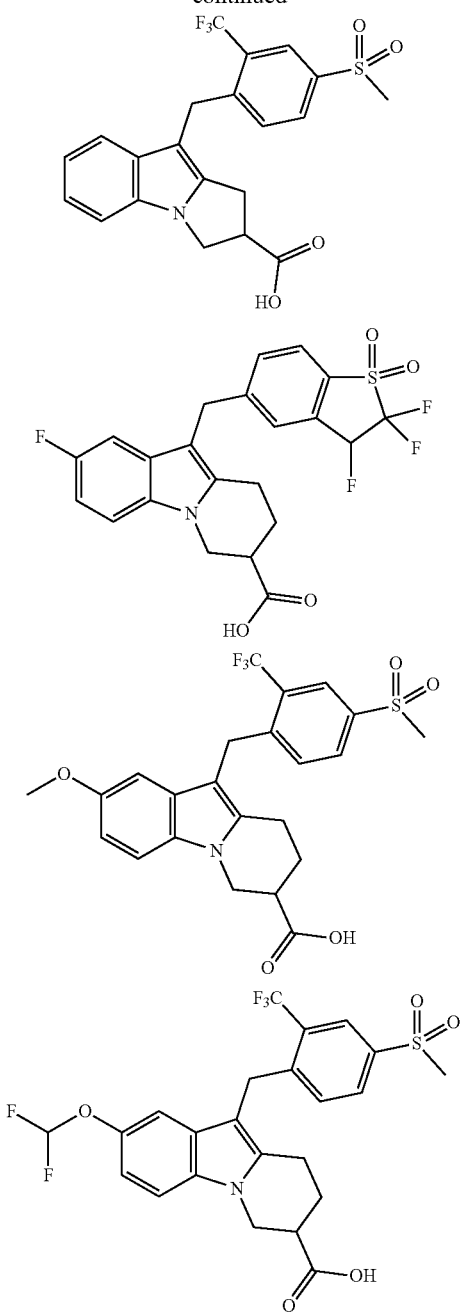
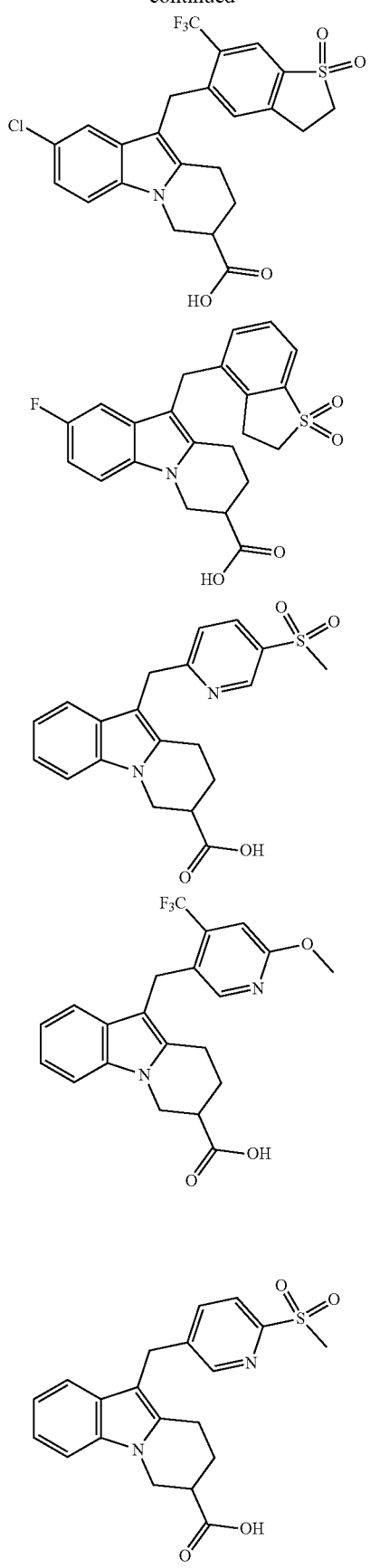

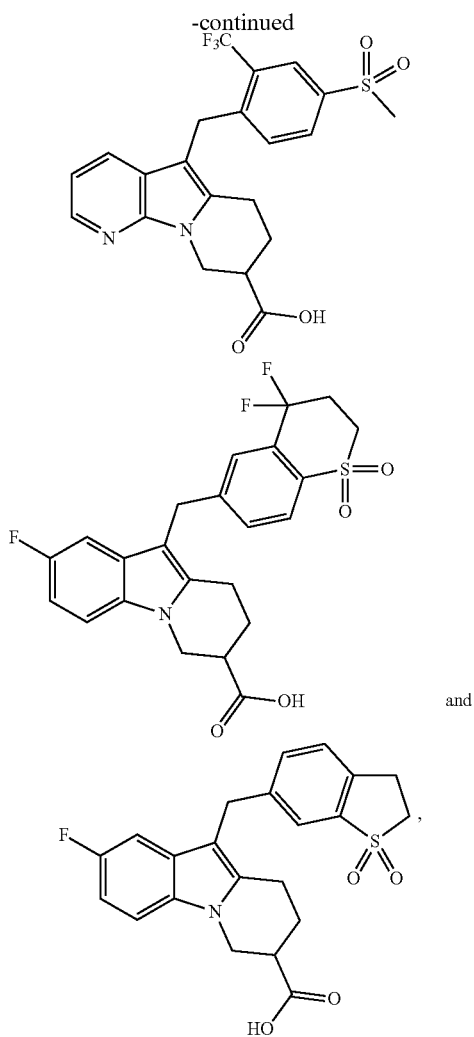

or a pharmaceutically acceptable salt thereof, or a tautomer thereof, or a stereoisomer thereof, or a solvate thereof.

In another aspect, the present application provides a pharmaceutical composition, comprising a compound represented by formula (I) of the present application, or a pharmaceutically acceptable salt thereof, or a tautomer thereof, or a stereoisomer thereof, or a solvate thereof. In some embodiments, the pharmaceutical composition of the present application further comprises a pharmaceutically acceptable adjuvant.

In another aspect, the present application provides a method for treating a disease mediated by a CRTH2 receptor in a mammal, comprising administering to a mammal, preferably a human, in need thereof a therapeutically effective amount of a compound represented by formula (I), or a pharmaceutically acceptable salt thereof, or a tautomer thereof, or a stereoisomer thereof, or a solvate thereof, or a pharmaceutical composition thereof.

In still another aspect, the present application relates to use of a compound represented by formula (I), or a pharmaceutically acceptable salt thereof, or a tautomer thereof, or a stereoisomer thereof, or a solvate thereof, or a pharmaceutical composition thereof in the preparation of a medicament for preventing or treating a disease mediated by a CRTH2 receptor.

In yet another aspect, the present application relates to a compound represented by formula (I), or a pharmaceutically acceptable salt thereof, or a tautomer thereof, or a stereoisomer thereof, or a solvate thereof, or a pharmaceutical composition thereof for use in preventing or treating a disease mediated by a CRTH2 receptor.

In some embodiments of the present application, the disease associated with a CRTH2 receptor is preferably an allergic disease, e.g., asthma and allergic rhinitis.

Definitions and Description

Unless otherwise indicated, the following terms and phrases as used herein are intended to have the following meanings. A particular term or phrase without a particular definition should not be regarded as being indefinite or unclear, but should be understood in its ordinary sense. When a tradename is used herein, it is intended to refer to the corresponding commodity or its active ingredient.

The term "pharmaceutically acceptable" means those compounds, materials, compositions and/or dosage forms, within the scope of reliable medical judgment, are suitable for use in contact with the tissues of humans and animals without excessive toxicity, irritation, allergic reactions or other problems or complications, while being commensurate with a reasonable benefit/risk ratio.

The term "pharmaceutically acceptable salt" refers to the salt of the compound of the present application, which is prepared from the compound with specific substituents discovered by the present application and a relatively non-toxic acid or base. When the compound of the present application contains a relatively acidic functional group, a base addition salt can be obtained by contacting the compound with a sufficient amount of a base. The pharmaceutically acceptable base addition salt includes the salt of sodium, potassium, calcium, ammonium, organic ammonium or magnesium or the like. When the compound of the present application contains a relatively alkaline functional group, an acid addition salt can be obtained by contacting the compound in neutral form with a sufficient amount of an acid. Examples of the pharmaceutically acceptable acid addition salt include an inorganic acid salt, wherein the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid, etc.; and an organic acid salt, wherein the organic acid includes such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluene sulfonic acid, citric acid, tartaric acid, methylsulfonic acid and the like; and also includes a salt of an amino acid (e.g. arginine), and a salt of an organic acid such as glucuronic acid and the like (see Berge et al., "Pharmaceutical Salts", *Journal of Pharmaceutical Science* 66: 1-19 (1977)). Some specific compounds of the present application contain alkaline and acidic functional groups so as to be able to be converted to any base addition salts or acid addition salts.

Preferably, the parent form of a compound is regenerated by contacting a salt with a base or an acid in a conventional manner and then separating the parent compound. The differences between the parent form of a compound and the various salt forms thereof lie in some physical properties. For example, the solubilities in a polar solvent are different.

The "pharmaceutically acceptable salt" as used herein belongs to the derivatives of the compound of the present application, wherein the parent compound is modified by being salified with an acid or base. Examples of the pharmaceutically acceptable salt include but not limited to: an inorganic or organic acid salt of a base (such as amine), an alkali metal or organic salt of an acid (such as carboxylic acid), and so on. The pharmaceutically acceptable salt includes common non-toxic salts or quaternary ammonium salts of the parent compound, such as a salt formed by a non-toxic inorganic or organic acid. The common non-toxic salts include but not limited to those salts derived from inorganic acids and organic acids, wherein the inorganic acids or organic acids are selected from 2-acetoxybenzoic acid, 2-isethionic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxynaphthoic acid, isethionic acid, lactic acid, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, subacetic acid, succinic acid, aminosulfonic acid, sulfanilic acid, sulphuric acid, tannic acid, tartaric acid and p-toluene sulfonic acid.

The pharmaceutically acceptable salt of the present application can be synthesized with a parent compound containing an acidic or alkaline group by a conventional chemical method. Generally, the preparation method of the salt comprises: reacting these compounds in the forms of free acids or bases with a stoichiometric amount of proper bases or acids in water or an organic solvent or a water-organic solvent mixture. In general, a non-aqueous media such as ether, ethyl acetate, ethanol, isopropanol or acetonitrile is preferable.

Some compounds of the present application may exist in non-solvate or solvate forms, including hydrate forms. In general, the solvate form is similar to the non-solvate form, both of which are included within the scope of the present application.

The compound of the present application may exist in the form of a specific stereoisomer, such as a geometrical isomer, enantiomer, diastereoisomer, conformational isomer and the like. The present application envisages all of these compounds, including tautomers, cis- and trans-isomers, (−)- and (+)-enantiomers, (R)- and (S)-enantiomers, diastereomers, (D)-isomers, (L)-isomers, as well as racemic mixtures and other mixtures, such as enantiomer- or diastereoisomer-enriched mixtures, all of these isomers and mixtures are included within the scope of the present application. Other asymmetric carbon atoms may exist in substituents such as alkyl. All of these isomers and their mixtures are included within the scope of the present application.

Optically active (R)- and (S)-isomers and (D)- and (L)-isomers can be prepared by asymmetric synthesis or chiral reagents or other conventional techniques. An enantiomer of a compound of the present application can be prepared by asymmetric synthesis or the derivatization action with chiral auxiliaries, in which the resulting diastereomer mixtures are isolated, and the auxiliary groups are cleaved to provide the desired pure enantiomer. Alternatively, when a molecule contains an alkaline functional group (such as amino) or an acidic functional group (such as carboxyl), the molecule is reacted with an appropriate optical active acid or base to form a diastereomer salt, the diastereomer is resoluted by well-known conventional methods in the art, and then pure enantiomers can be obtained. In addition, the separation of enantiomers and diastereomers is usually realized by chromatography, which employs a chiral stationary phase, and optionally is combined with the chemical derivatization method (e.g. a carbamate is generated from an amine).

The compound of the present application may comprise unnatural proportion of atomic isotopes at one or more atoms that constitute the compound. For example, the compound can be labeled by a radioactive isotope, such as tritium ($^3$H), iodine-125 ($^{125}$I) or C-14 ($^{14}$C). All the variants composed by isotopes of the compound disclosed in the present application, whether radioactive or not, are included within the scope of the present application.

The term "a pharmaceutically acceptable carrier" refers to any formulation or carrier medium which is capable of delivering an effective amount of the active substance disclosed in the present application, does not interfere with the biological activity of the active substance, and has no toxic side-effects on a host or patient. Representative carriers include water, oil and minerals, cream base, lotion matrix, ointment matrix, etc. These matrixes include suspensions, suspending agent, viscosity increasers, transdermal enhancers, etc. Other information about the carrier can refer to *Remington: The Science and Practice of Pharmacy*, 21st Ed., Lippincott, Williams & Wilkins (2005), the content of which is incorporated herein by reference.

The term "adjuvant" usually refers to a carrier, diluent and/or medium required for the preparation of an effective pharmaceutical composition.

For a drug or pharmacological active agent, the term "effective amount" or "therapeutically effective amount" refers to a sufficient amount of a drug or formulation that can achieve desired effects but is non-toxic. The determination of an effective amount varies from person to person, depending on the age and the general condition of a subject, and also depending on the specific active substance. An appropriate effective amount in individual cases can be determined by the person skilled in the art according to conventional tests.

The term "active ingredient", "therapeutic agent", "active substance" or "active agent" refers to a chemical entity, which can effectively treat a target disorder, disease or condition.

"Optional" or "optionally" means that the subsequently described event or circumstance may but does not have to occur, and that the description includes instances where the event or circumstance occurs and instances where it does not.

The term "substituted" refers to one or more hydrogen atoms on a specific atom are substituted by a substituent, including deuterium and variants of hydrogen, as long as the valence state of the specific atom is normal and the compound obtained after substitution is stable. The term "optionally substituted" means that it may be substituted or not be substituted, and unless otherwise specified, the type and number of substituents can be arbitrary under the premise that it can be achieved in chemistry.

When any variable (e.g. R) occurs more than one time in the composition or structure of a compound, the definition in each occurrence is independent. Therefore, for example, if a group is substituted by 0-2 R, the group may optionally be substituted by at most two R, and R in each case has an independent option. In addition, the combination of substituents and/or their variants is allowed only if such a combination will lead to a stable compound.

When the number of a linking group is 0, e.g., —(CRR)$_0$—, it means that the linking group is a single bond.

When one of the variables is a single bond, it means that the two groups connected thereto are directly connected to each other. For example, when L in A-L-Z represents a single bond, it means that the structure is actually A-Z.

When a substituent is absent, it means that the substituent is not present. For example, when X in A-X is absent, it means that the structure is actually A. When the bonds of a substituent are cross-connected to two atoms on a ring, the substituent can be bonded with any atom on the ring. When the atom, through which an enumerated substituent is connected to a compound that is included in the general formula of a chemical structure but is not specifically mentioned, is not designated, the substituent can be bonded with any atom thereof. The combination of substituents and/or their variants is allowed only if such a combination will lead to a stable compound. For example, a structural unit

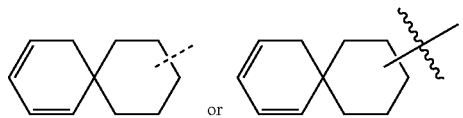

means that it may be substituted at any position on cyclohexyl or cyclohexadiene.

Unless otherwise specified, the term "hetero" represents a heteroatom or a heteroatom group (i.e. a group containing a heteroatom), including atoms except for carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" includes a single ring, a linked ring, a spiro ring, a fused ring or a bridged ring. The number of the atoms in the ring is usually defined as the number of the members forming the ring, for example, "5- to 7-membered ring" refers to a ring formed by 5 to 7 atoms. Unless otherwise specified, the ring optionally contains 1-3 heteroatoms. Therefore, "5- to 7-membered ring" includes, for example, phenyl, pyridinyl and piperidinyl; on the other hand, the term "5- to 7-membered heterocyclyl" includes pyridyl and piperidinyl, but does not include phenyl. The term "ring" also includes a ring system containing at least one ring, wherein each "ring" independently meets the above definition.

Unless otherwise specified, the term "heterocycle" or "heterocyclyl" refers to a stable monocyclic, bicyclic or tricyclic ring containing a heteroatom or a heteroatom group, they may be saturated, partially unsaturated or unsaturated (aromatic), and they contain carbon atoms and 1, 2, 3 or 4 heteroatoms which are independently selected from the group consisting of N, O and S, wherein any of the above-mentioned heterocycle may be fused to a benzene ring to form a bicyclic ring. Nitrogen atoms and sulfur atoms may be optionally oxidized (i.e., NO and S(O)$_p$, p is 1 or 2). The nitrogen atoms may be substituted or unsubstituted (i.e. N or NR, wherein R is H or other substituents that have been defined herein). The heterocycle may be attached to the side group of any heteroatoms or carbon atoms to form a stable structure. If the formed compound is stable, the heterocycle described herein may be substituted on its carbon or nitrogen atoms. The nitrogen atoms in the heterocycle are optionally quaternized. A preferred embodiment is, when the total number of S and O atoms in the heterocycle is more than 1, these heteroatoms are not adjacent to each other. Another preferred embodiment is the total number of S and O atoms in the heterocycle is not more than 1. As used herein, the term "aromatic heterocyclic group" or "heteroaryl" refers to a stable 5-, 6-, 7-membered monocyclic or bicyclic or 7-, 8-, 9- or 10-membered bicyclic aromatic heterocyclyl, which contains carbon atoms and 1, 2, 3 or 4 heteroatoms which are independently selected from the group consisting of N, O and S. The nitrogen atoms may be substituted or unsubstituted (i.e. N or NR, wherein R is H or other substituents that have been defined herein). Nitrogen atoms and sulfur atoms may be optionally oxidized (i.e., NO and S(O)$_p$, p is 1 or 2). It is worth noting that, the total number of S and O atoms in the aromatic heterocycle is not more than 1. Bridged rings are also included in the definition of the heterocycle. When one or more atoms (i.e. C, O, N, or S) are connected to two nonadjacent carbon atoms or nitrogen atoms, a bridged ring is formed. It is worth noting that, a bridge always converts a monocyclic ring into a tricyclic ring. In the bridged ring, the substituent in the ring may also locate on the bridge.

Examples of heterocyclyl include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl, decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazinyl, phenothiazinyl, benzoxanthinyl, phenoxazinyl, phthalazinyl, piperazinyl, piperidyl, piperidonyl, 4-piperidonyl, piperonyl, pteridyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused-ring and spiro-ring compounds are also included.

Unless otherwise specified, the term "hydrocarbyl" or its specific terms (such as alkyl, alkenyl, alkynyl, aryl and so on) themself or as a part of another substituent represent a linear, branched or cyclic hydrocarbon group or a combination thereof, which may be completely saturated (such as alkyl), or mono- or poly-unsaturated (such as alkenyl, alkynyl and aryl), may be monosubstituted or multisubstituted, may be monovalent (e.g., methyl), divalent (e.g., methylene) or multivalent (e.g., methine), may include bivalent or multivalent atomic groups, and have a specified number of carbon atoms (for example, $C_1$-$C_{12}$ represents 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, and $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes but not limited to aliphatic hydrocarbyl and aromatic hydrocarbyl. The aliphatic hydrocarbyl includes linear and cyclic aliphatic hydrocarbyl, and specifically includes but not limited to alkyl, alkenyl and alkynyl. The aromatic hydrocarbyl includes but not limited to 6- to 12-membered aromatic hydrocarbyl, such as phenyl, naphthyl and the like. In some embodiments, the term "hydrocarbyl" represents a linear or branched atomic group or a combination thereof, which may be completely saturated, or mono- or poly-unsaturated, and may include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, cyclohexyl, (cyclohexyl)methyl, cyclopropyl methyl, and n-amyl, n-hexyl, n-heptyl, n-octyl and the like. Unsaturated hydrocarbyl has one or more double bonds or triple bonds, and its examples include but not limited to vinyl, 2-propenyl, butenyl, crotyl, 2-isopentenyl, 2-butadienyl, 2,4-pentadienyl, 3-(1,4-pentadienyl), acetenyl, 1-propinyl and 3-propinyl, 3-butynyl, and the like.

Unless otherwise specified, the term "heterohydrocarbyl" or its specific terms (such as heteroalkyl, heteroalkenyl, heteroalkynyl, heteroaryl and the like) themself or combining with another term represents a stable linear, branched or cyclic hydrocarbon group or a combination thereof, which consists of a certain number of carbon atoms and at least one heteroatom. In some embodiments, the term "heteroalkyl" itself or combining with another term represents a stable linear, or branched hydrocarbon group or a combination thereof, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atoms are optionally quaternized. Heteroatoms or heteroatom groups may be located in any internal positions of the heterohydrocarbyl, including the position where the hydrocarbyl is attached to the rest part of the molecule. However, the terms "alkoxy", "alkylamino" and "alkylthio" (or thioalkoxy) belong to customary expressions, and refer to those alkyl groups which are attached to the rest of a molecular via an oxygen atom, an amino group or a sulfur atom, respectively. Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—O$CH_3$ and —CH=CH—N($CH_3$)—$CH_3$. At most two heteroatoms may be adjacent, such as —$CH_2$—NH—O$CH_3$.

Unless otherwise specified, the terms "cyclohydrocarbyl", "heterocyclohydrocarbyl" or specific terms thereof (such as aryl, heteroaryl, cycloalkyl, heterocycloalkyl, cycloalkenyl, heterocycloalkenyl, cycloalkynyl, heterocycloalkynyl and the like) themself or combining with other terms respectively represent a cyclic "hydrocarbyl" or "heterohydrocarbyl". In addition, in terms of heterohydrocarbyl or heterocyclohydrocarbyl (such as heteroalkyl and heterocycloalkyl), heteroatoms may occupy the position where the heterocyclic ring is attached to the rest part of the molecule. Examples of cyclohydrocarbyl include but not limited to cyclopentyl, cyclohexyl, 1-cyclohexenyl, 3-cyclohexenyl, cycloheptyl, etc. Non-limited examples of heterocyclohydrocarbyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophen-2-yl, tetrahydrothiophen-3-yl, 1-piperazinyl and 2-piperazinyl.

Unless otherwise specified, the term "alkyl" refers to a straight or branched saturated hydrocarbyl, which may be monosubstituted (e.g., —$CH_2$F) or multisubstituted (e.g., —$CF_3$), and may be monovalent (e.g., methyl), divalent (e.g., methylene) or multivalent (e.g., methine). Examples of alkyl include methyl (Me), ethyl (Et), propyl (e.g., n-propyl and isopropyl), butyl (e.g., n-butyl, isobutyl, s-butyl, and t-butyl), pentyl (e.g., n-pentyl, isopentyl, and neopentyl), and the like.

Unless otherwise specified, cycloalkyl includes any stable monocyclic or polycyclic hydrocarbyl, in which any carbon atom is saturated. Cycloalkyl may be monosubstituted or multisubstituted, and may be monovalent, divalent or multivalent. Examples of cycloalkyl include, but are not limited to, cyclopropyl, norbornanyl, [2.2.2]dicyclooctane, [4.4.0] dicyclodecane, and the like.

Unless otherwise specified, the term "halo" or "halogen", by itself or as part of another substituent, represents a fluorine, chlorine, bromine or iodine atom.

The term "alkoxy" represents oxo-bridged alkyl having the number of carbon atoms designated. Unless otherwise specified, $C_{1-6}$ alkoxy includes $C_1$, $C_2$, $C_3$, $C_4$, $C_5$, and $C_6$ alkoxy. Examples of alkoxy include, but are not limited to: methoxy, ethoxy, n-propoxy, isopropoxy, n-butoxy, s-butoxy, t-butoxy, n-pentyloxy, and S-pentyloxy.

Unless otherwise specified, the term "aryl" represents a polyunsaturated aromatic hydrocarbon substituent, which may be monosubstituted or multisubstituted, and may be monovalent, divalent or multivalent. It may be monocyclic or polycyclic (for example, 1-3 rings; wherein at least one ring is aromatic). They are fused together or connected covalently.

The term "heteroaryl" refers to an aryl containing 1 to 4 heteroatoms. In an exemplary embodiment, the heteroatom is selected from the group consisting of B, N, O, and S, in which the nitrogen and sulfur atoms are optionally oxidized, and the nitrogen atoms are optionally quaternized. The heteroaryl may be connected to the rest part of the molecule via a heteroatom. Non-limited examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl.

The compound of the present application can be prepared through many synthetic methods which are well-known to the person skilled in the art, including the following specific embodiments, embodiments obtained by combining the specific embodiments with other chemical synthetic methods and the equivalent alternative methods which are well-known to the person skilled in the art. The preferred embodiments include but not limited to the examples of the present application.

The solvents used in the present application are commercially available. The following abbreviations are used in the present application: aq represents water; HATU represents 0-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amino protecting group;

BOC represents tert-butoxycarbonyl, which is an amino protecting group; HOAc represents acetic acid; NaCNBH₃ represents sodium cyanoborohydride; r.t. represents room temperature; O/N represents overnight; THF represents tetrahydrofuran; Boc₂O represents di-tert-butyl dicarbonate; TFA represents trifluoroacetic acid; DIPEA represents diisopropylethylamine; SOCl₂ represents thionyl chloride; CS₂ represents carbon disulfide; TsOH represents p-toluenesulfonic acid; NFSI represents N-fluoro-N-(phenyl sulfonyl) benzenesulfonamide; NCS represents 1-chloropyrrolidine-2,5-dione; n-Bu₄NF represents tetrabutylammonium fluoride; iPrOH represents 2-propanol; mp represents melting point; and LDA represents lithium diisopropylamide.

The compounds are named artificially or named by ChemDraw® software, and vendor directory names are used for the commercially available compounds.

EXAMPLES

The present application is illustrated in detail hereinafter in conjunction with the examples, which are not intended to limit the present application in any way. The present application has been described in detail herein, and the specific examples thereof are also disclosed. It will be apparent for those skilled in the art to make various changes and improvements of the examples of present application without departing from the spirit and scope of the present application.

Example 1

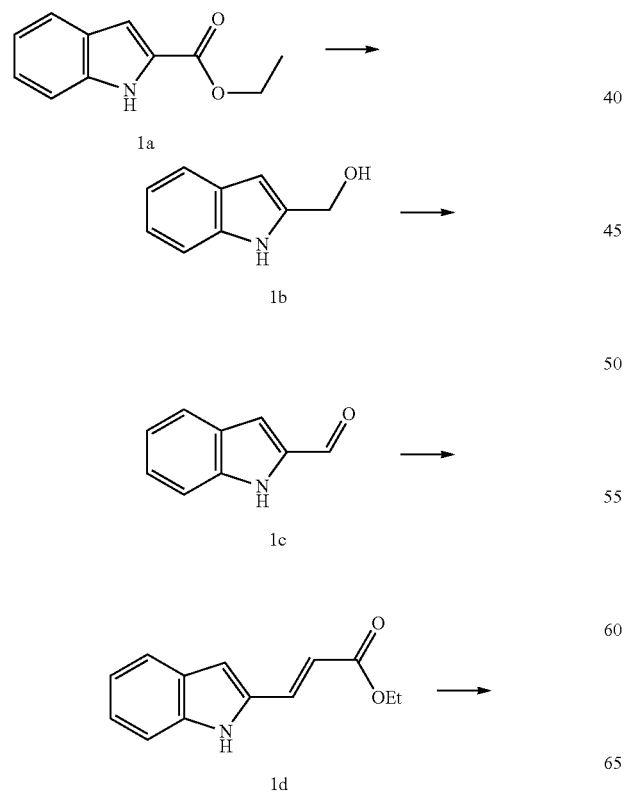

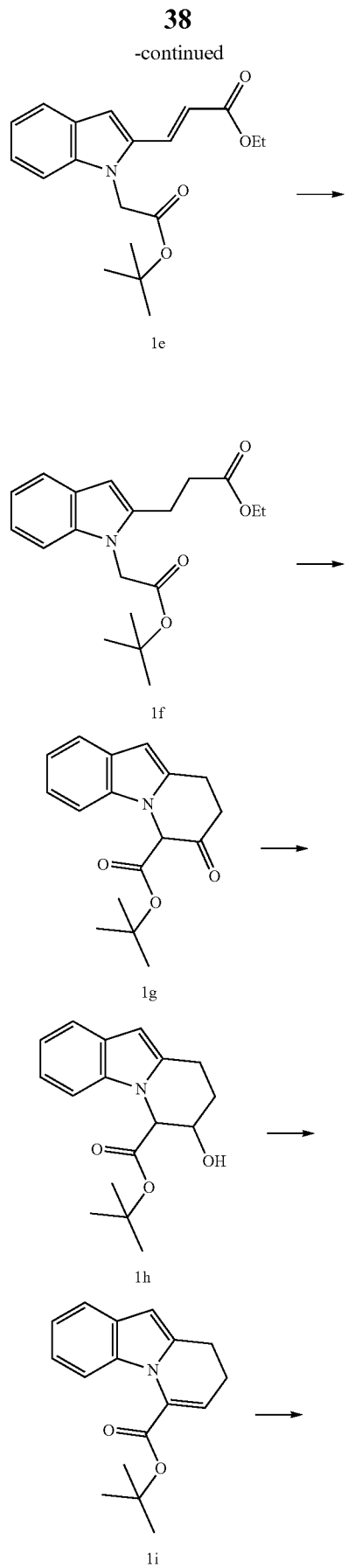

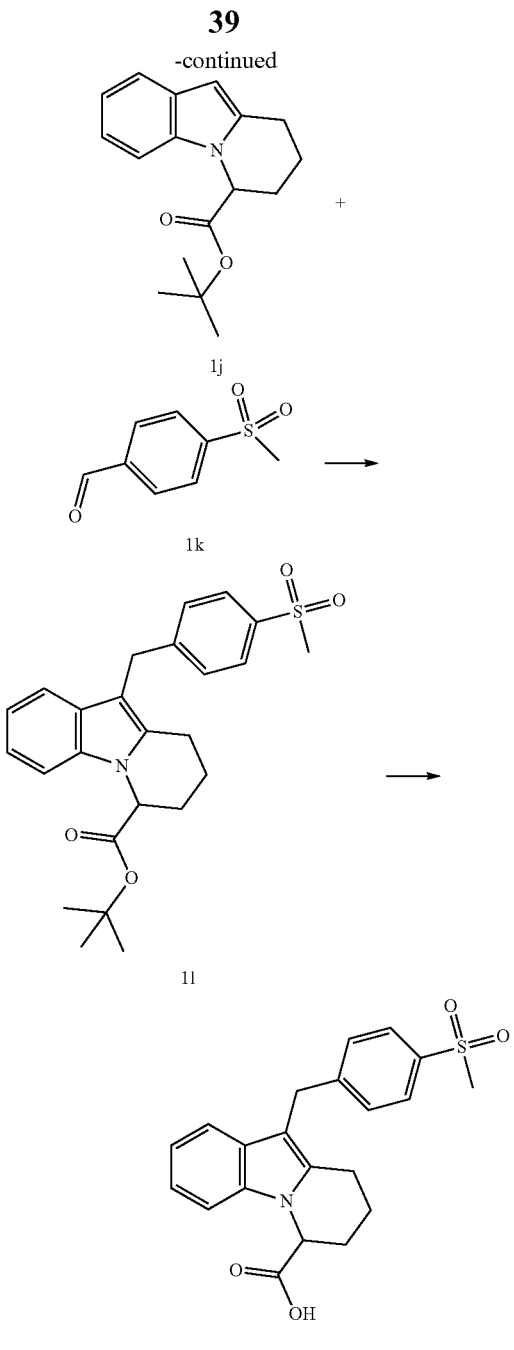

Step I

Compound 1a (100.00 g, 528.51 mmol) was dissolved in tetrahydrofuran (1000 mL), and lithium aluminum hydride (24.07 g, 634.21 mmol) was slowly added in batch at 0° C. The reaction mixture was stirred at this temperature for 1.5 hr, and then water (24 mL), 10% sodium hydroxide solution (24 mL), and water (72 mL) were successively added dropwise. The resulting mixture was dried over anhydrous sodium sulfate, filtered and concentrated under reduced pressure to dryness to obtain an oil crude product. The oil crude product was then slurried in a mixed solvent of ethyl acetate and petroleum ether (300 mL, v/v=50/1) to give Compound 1b (59.00 g, yield: 75%). $^1$H NMR (400 MHz, CDCl$_3$) δ8.37 (br. s., 1H), 7.59 (d, J=7.6 Hz, 1H), 7.34 (d, J=8.0 Hz, 1H), 7.22-7.16 (m, 1H), 7.15-7.07 (m, 1H), 6.41-6.40 (m, 1H), 4.81 (s, 2H), 1.97 (br. s., 1H). MS-ESI calculated value [M+H]$^+$ 148, measured value 148.

Step II

Compound 1b (58.00 g, 394.10 mmol) was dissolved in dichloromethane (800 mL), and manganese dioxide (239.84 g, 2.76 mol) was slowly added in batch at 0° C. The reaction mixture was stirred for 16 hr at 25-30° C. The reaction mixture was filtered, and the filter cake was washed with dichloromethane (200 mL×2). The combined filtrate was concentrated under reduced pressure to dryness, and separated and purified by silica gel column chromatography (petroleum ether/ethyl acetate 100-60%) to give Compound 1c (34.00 g, yield: 57%). $^1$H NMR (400 MHz, CDCl$_3$) δ9.86 (s, 1H), 9.19 (br. s., 1H), 7.76 (d, J=8.0 Hz, 1H), 7.49-7.44 (m, 1H), 7.43-7.36 (m, 1H), 7.30-7.29 (m, 1H), 7.21-7.15 (m, 1H). MS-ESI calculated value [M+H]$^+$ 146, measured value 146.

Step III

Compound 1c (40.00 g, 275.56 mmol) was dissolved in dichloromethane (1000 mL), and ethyl (triphenylphosphoranylidene)acetate (100.80 g, 289.34 mmol) was added in batch. The reaction mixture was stirred for 16 hr at 25-30° C., concentrated under reduced pressure to dryness, and then purified by silica gel column chromatography (petroleum ether/ethyl acetate 100-90%), to give Compound 1d (26.80 g, yellowish solid, yield: 43%). $^1$H NMR (400 MHz, CDCl$_3$) δ8.55 (br. s., 1H), 7.69 (d, J=16.2 Hz, 1H), 7.62 (d, J=8.0 Hz, 1H), 7.39-7.33 (m, 1H), 7.30-7.25 (m, 1H), 7.15-7.08 (m, 1H), 6.82 (d, J=1.6 Hz, 1H), 6.26 (d, J=16.0 Hz, 1H), 4.29 (q, J=7.2 Hz, 2H), 1.35 (t, J=7.2 Hz, 3H). MS-ESI calculated value [M+H]$^+$ 216, measured value 216.

Step IV

Compound 1d (26.80 g, 124.51 mmol) was dissolved in dimethylformamide (300 mL), and cesium carbonate (87.22 g, 267.70 mmol) and t-butyl bromoacetate (40.07 g, 205.44 mmol) were added. The reaction mixture was stirred for 16 hr at 60° C., cooled to the room temperature, poured into water (1.5 L) to quench the reaction, and then extracted with ethyl acetate (500 mL×2). The organic phase was concentrated under reduced pressure to dryness, and then purified by silica gel column chromatography (petroleum ether/ethyl acetate 100-90%), to give Compound 1e (40.00 g, red oil, yield: 90%). $^1$H NMR (400 MHz, CDCl$_3$) δ7.66 (d, J=15.6 Hz, 1H), 7.62 (d, J=8.0 Hz, 1H), 7.29-7.25 (m, 1H), 7.25 (d, J=1.2 Hz, 1H), 7.16-7.10 (m, 1H), 7.00 (s, 1H), 6.47 (d, J=15.6 Hz, 1H), 4.85 (s, 2H), 4.27 (q, J=7.2 Hz, 2H), 1.44 (s, 9H), 1.34 (t, J=7.2 Hz, 3H). MS-ESI calculated value [M+H]$^+$ 330, measured value 330.

Step V

Compound 1e (40.00 g, 121.44 mmol) was dissolved in ethyl acetate (360 mL), and wet palladium on carbon (4.00 g, 10%, moisture content: 50%) was added. The reaction mixture was stirred under a hydrogen (50 psi) atmosphere for 16 hr at 25-30° C., filtered through celite, and concentrated, to give Compound 1f (40.50 g, yellow oil, yield: 93%). $^1$H NMR (400 MHz, CDCl$_3$) δ7.53 (d, J=7.6 Hz, 1H), 7.21-7.13 (m, 2H), 7.11-7.05 (m, 1H), 6.29 (s, 1H), 4.72 (s, 2H), 4.20-4.14 (m, 2H), 3.08-2.97 (m, 2H), 2.84-2.75 (m, 2H), 1.43 (s, 9H), 1.30-1.26 (m, 3H). MS-ESI calculated value [M+H]$^+$ 332, measured value 332.

Step VI

Compound 1f (20.00 g, 60.35 mmol) was dissolved in tetrahydrofuran (100 mL), and the resulting solution was cooled to −10° C., and a solution of potassium t-butoxide (16.93 g, 150.88 mmol) in tetrahydrofuran (400 mL) was slowly added dropwise. The reaction mixture was warmed to 25-30° C. and stirring for 2.5 hr, and then 1 N hydrochloric acid (150 mL) was added to quench the reaction. Tetrahydrofuran was evaporated to dryness, and the resulting mixture was extracted with ethyl acetate (250 mL×2). The organic phase was concentrated under reduced pressure to dryness, and purified by flash silica gel column chromatography (petroleum ether/ethyl acetate 100-90%), to give Compound 1g (8.00 g, yellow oil, yield: 46%). $^1$H NMR (400 Hz, CDCl$_3$) δ7.58 (d, J=7.6 Hz, 1H), 7.25-7.11 (m, 3H), 6.38 (s, 1H), 5.40 (s, 1H), 3.37-3.25 (m, 2H), 2.99-2.89 (m, 1H), 2.73-2.63 (m, 1H), 1.39 (s, 9H). MS-ESI calculated value [M+H]$^+$ 286, measured value 286.

Step VII

Compound 1g (4.00 g, 14.02 mmol) was dissolved in tetrahydrofuran (100 mL), and the resulting solution was cooled to 0° C., and sodium borohydride (530.31 mg, 14.02 mmol) was added in batch. The reaction mixture was warmed to 25-30° C. and stirring for 1 hr, and then 1 N hydrochloric acid was added to adjust the pH to 6-7. Tetrahydrofuran was evaporated to dryness, and the resulting mixture was extracted with ethyl acetate (50 mL×2). The organic phase was concentrated under reduced pressure to dryness to give Compound 1h (4.00 g, yellow solid, yield: 85%). MS-ESI calculated value [M+H]$^+$ 288, measured value 288.

Step VIII

Compound 1h (4.00 g, 13.92 mmol) and triethylamine (2.82 g, 27.84 mmol) were dissolved in dichloromethane (100 mL), and methanesulfonyl chloride (2.46 g, 21.48 mmol) was added. The reaction mixture was stirred for 1 hr at 25-30° C., directly concentrated to dryness, dissolved in dimethylformamide (100 mL), and diazabicyclo (6.36 g, 41.76 mmol) was added. The resulting reaction mixture was heated to 100° C., and stirred for 16 hr. The reaction mixture was cooled to the room temperature, poured into water (500 mL), and then extracted with ethyl acetate (75 mL×2). The organic phase was washed with saturated brine (200 mL), dried over anhydrous sodium sulfate, filtered, concentrated under reduced pressure to dryness, and purified by flash silica gel column chromatography (petroleum ether/ethyl acetate 100-95%), to give Compound 1i (1.80 g, yellow oil, yield: 48%). MS-ESI calculated value [M+H]$^+$ 270, measured value 270.

Step IX

Compound 1i (1.80 g, 6.68 mmol) was dissolved in ethyl acetate (50 mL), and wet palladium on carbon (0.20 g, 10%, moisture content: 50%) was added. The reaction mixture was stirred under a hydrogen (50 psi) atmosphere for 16 hr at 25-30° C., filtered through celite, and concentrated to give Compound 1j (1.75 g, yellowish solid, yield: 94%). $^1$H NMR (400 MHz, CDCl$_3$) δ7.54-7.48 (m, 1H), 7.13-7.04 (m, 3H), 6.22 (s, 1H), 4.96-4.86 (m, 1H), 3.16-2.82 (m, 2H), 2.40-2.21 (m, 2H), 1.93-1.84 (m, 2H), 1.37 (s, 9H). MS-ESI calculated value [M+H]$^+$ 272, measured value 272.

Step X

Compound 1j (30 mg, 0.11 mmol) and Compound 1k (22 mg, 0.12 mmol) were dissolved in 1,2-dichloroethane (3 mL), and triethylsilane (64 mg, 0.55 mmol) and trifluoroacetic acid (38 mg, 0.33 mmol) were added at 0° C. The reaction mixture was stirred for 16 hr at 25° C., and then water (5 mL) was added to quench the reaction. The resulting mixture was adjusted with a saturated solution of sodium bicarbonate to pH 7, and extracted with ethyl acetate (10 ml×2). The organic phases were combined, dried over anhydrous sodium sulfate, filtered, concentrated under reduced pressure to dryness, and purified by chromatography on silica gel plates (petroleum ether/ethyl acetate=1/1) to give Compound 1l (36 mg, yellow oil, yield: 74%). MS-ESI calculated value [M+H]$^+$ 440, measured value 440.

Step XI

Compound 1l (36 mg, 0.082 mmol) was dissolved in ethyl acetate (5 mL), and hydrochloric acid/ethyl acetate (4 M, 2 mL) was added. The reaction mixture was stirred for 16 hr at 25° C., directly concentrated under reduced pressure to dryness, and separated and purified by high performance liquid chromatography to give Compound 1 (8 mg, yield: 26%). $^1$H NMR (400 MHz, CD$_3$OD) δ7.80-7.78 (m, 2H), 7.47-7.45 (m, 2H), 7.33-7.30 (m, 1H), 7.17-7.11 (m, 1H), 7.08-7.05 (m, 1H), 7.01-6.94 (m, 1H), 5.14-5.04 (m, 1H), 4.29-4.08 (m, 2H), 3.05 (s, 3H), 3.04-2.99 (m, 1H), 2.84-2.74 (m, 1H), 2.46-2.26 (m, 2H), 2.00-1.82 (m, 2H). MS-ESI calculated value [M+H]$^+$ 384, measured value 384.

Example 2

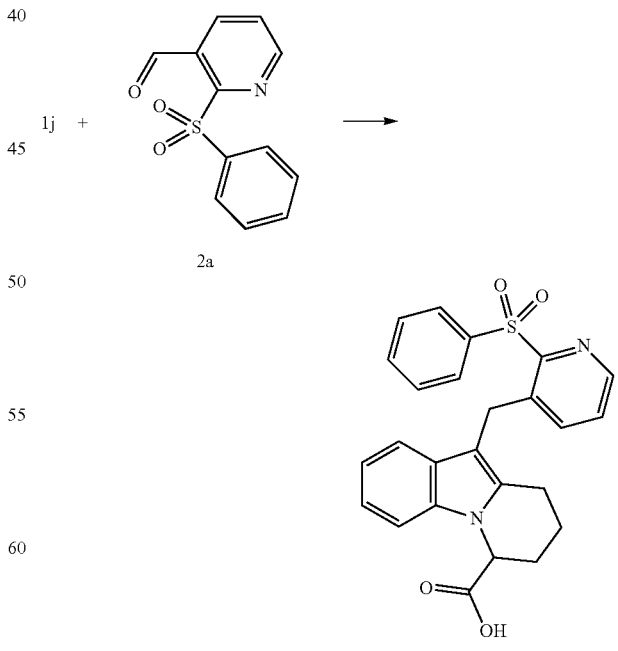

Compound 1j reacted with Compound 2a according to the synthesis method in Example 1 to give Compound 2 (8 mg, yield: 24%). $^1$H NMR (400 MHz, CD$_3$OD) δ8.35-8.34 (m, 1H), 8.03-8.01 (m, 2H), 7.77-7.69 (m, 1H), 7.67-7.59 (m, 2H), 7.51-7.49 (m, 1H), 7.34 (m, 1H), 7.16-7.14 (m, 1H), 7.07-7.04 (m, 1H), 7.00-6.95 (m, 1H), 6.93-6.87 (m, 1H), 5.16-5.06 (m, 1H), 4.52 (s, 2H), 2.87-2.77 (m, 1H), 2.69-2.59 (m, 1H), 2.46-0.25 (m, 2H), 1.95-1.76 (m, 2H). MS-ESI calculated value [M+H]$^+$ 447, measured value 447.

Example 3

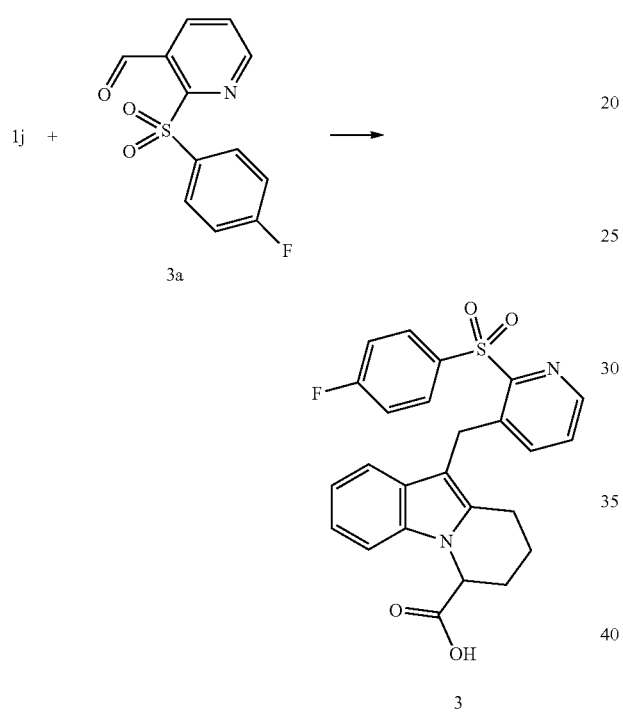

Compound 1j reacted with Compound 3a according to the synthesis method in Example 1 to give Compound 3 (13 mg, yield: 41%). $^1$H NMR (400 MHz, CD$_3$OD) δ8.33-8.32 (m, 1H), 8.07-7.99 (m, 2H), 7.56-7.54 (m, 1H), 7.39-7.29 (m, 3H), 7.18-7.12 (m, 1H), 7.08-6.99 (m, 2H), 6.94-6.87 (m, 1H), 5.16-5.08 (m, 1H), 4.56 (s, 2H), 2.94-2.84 (m, 1H), 2.75-2.65 (m, 1H), 2.47-2.25 (m, 2H), 1.98-1.79 (m, 2H). MS-ESI calculated value [M+H]$^+$ 465, measured value 465.

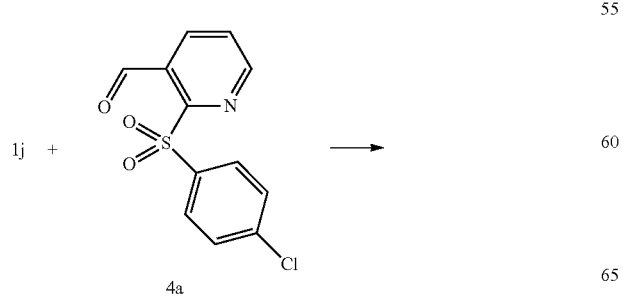

-continued

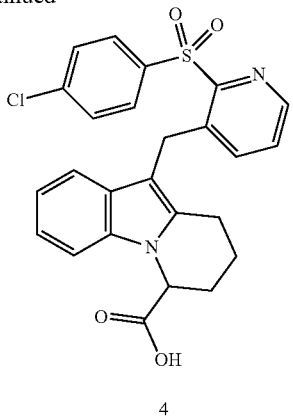

Example 4

Compound 1j reacted with Compound 4a according to the synthesis method in Example 1 to give Compound 4 (14 mg, yield: 40%). $^1$H NMR (400 MHz, CD$_3$OD) δ8.35-8.34 (m, 1H), 7.97-7.94 (m, 2H), 7.64-7.62 (m, 2H), 7.58-7.56 (m, 1H), 7.41-7.33 (m, 1H), 7.18-7.13 (m, 1H), 7.09-6.99 (m, 2H), 6.94-6.88 (m, 1H), 5.16-5.08 (m, 1H), 4.56 (s, 2H), 2.93-2.85 (m, 1H), 2.74-2.64 (m, 1H), 2.42-2.41 (m, 1H), 2.36-2.27 (m, 1H), 1.95-1.83 (m, 2H). MS-ESI calculated value [M+H]$^+$ 481, measured value 481.

Example 5

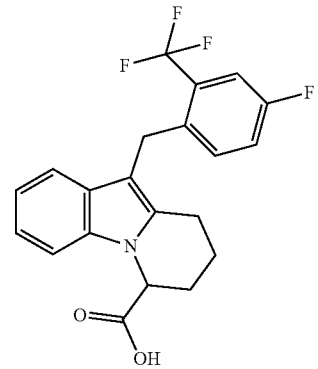

Compound 1j reacted with Compound 5a according to the synthesis method in Example 1 to give Compound 5 (3 mg, yield: 8%). $^1$H NMR (400 MHz, CD$_3$OD) δ: 7.44 (d, J=9.2 Hz, 1H), 7.22-7.13 (m, 2H), 7.12-7.03 (m, 3H), 6.99-6.92 (m, 1H), 5.08 (br. s., 1H), 4.19 (s, 2H), 2.97-2.88 (m, 1H), 2.79-2.71 (m, 1H), 2.47-2.29 (m, 2H), 1.93 (d, J=9.2 Hz, 2H). MS-ESI calculated value [M+H]+ 392, measured value 392.

Example 6

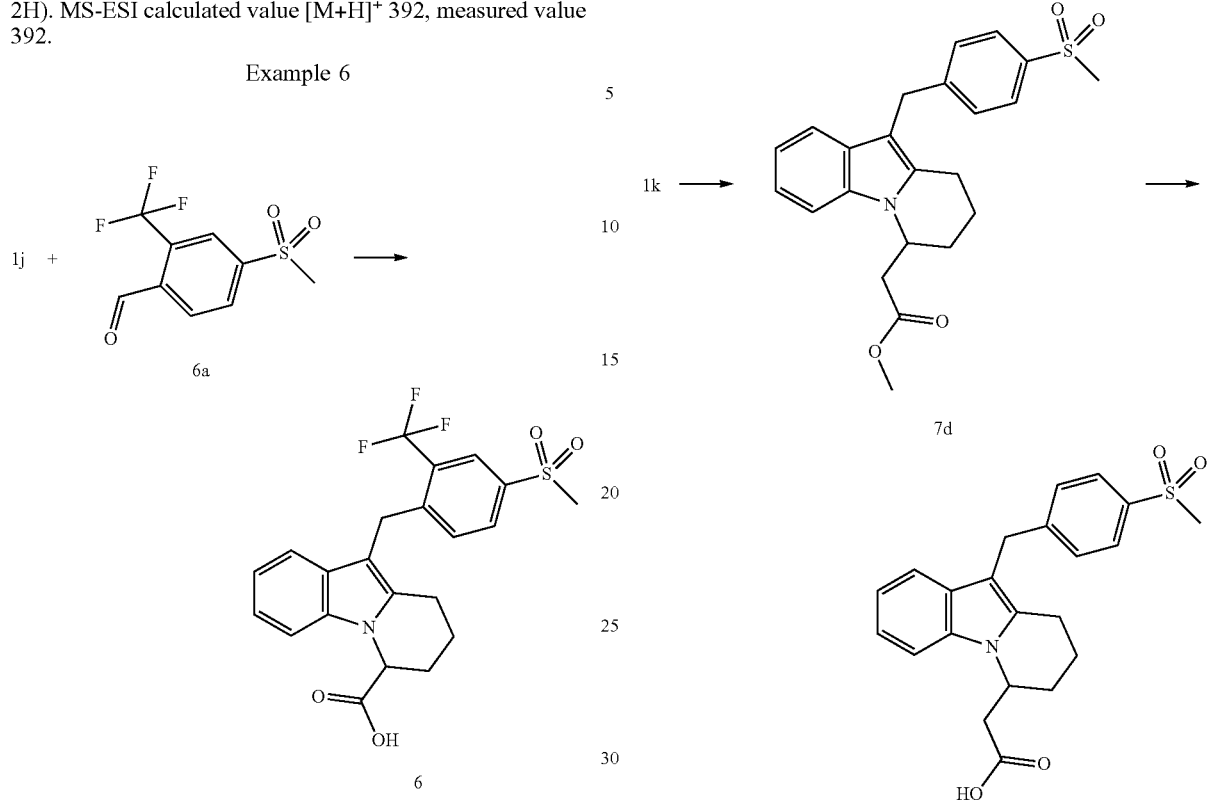

Compound 1j reacted with Compound 6a according to the synthesis method in Example 1 to give Compound 6 (29 mg, yield: 41%). ¹H NMR (400 MHz, CD₃OD) δ8.25-8.24 (m, 1H), 7.94-7.92 (m, 1H), 7.37-7.34 (m, 1H), 7.22-7.14 (m, 2H), 7.12-7.04 (m, 1H), 7.01-6.94 (m, 1H), 5.18-5.08 (m, 1H), 4.33 (s, 2H), 3.13 (s, 3H), 2.98-2.90 (m, 1H), 2.82-2.72 (m, 1H), 2.48-2.30 (m, 2H), 1.97-1.89 (m, 2H). MS-ESI calculated value [M+H]+ 452, measured value 452.

Example 7

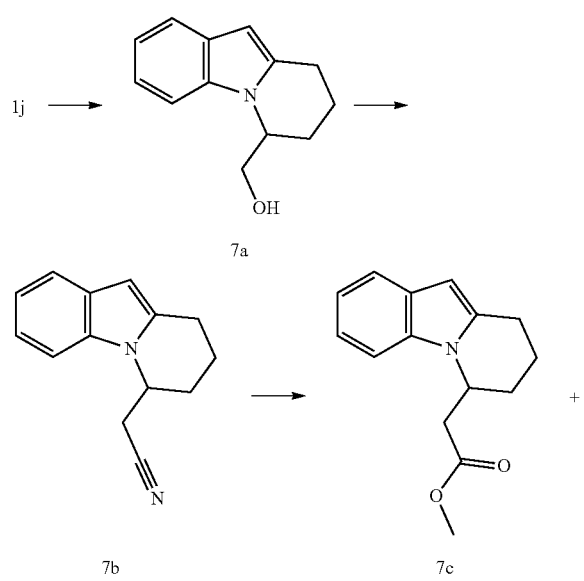

Step I

Compound 1j (2.40 g, 8.84 mmol) was dissolved in tetrahydrofuran (60 mL), and lithium aluminum hydride (336 mg, 8.84 mmol) was slowly added in batch at 0° C. The reaction mixture was warmed to 25° C., and stirring for 1 hr, and then water (0.4 mL), 15% sodium hydroxide solution (1.2 mL), and water (0.4 mL) were successively added dropwise. The resulting mixture was dried over anhydrous sodium sulfate, filtered, and concentrated, to give Compound 7a (1.75 g, yellow oil, yield: 92%). MS-ESI calculated value [M+H]+ 202, measured value 202.

Step II

Compound 7a (1.75 g, 8.70 mmol) and triethylamine (1.76 g, 17.40 mmol) were dissolved in dichloromethane (50 mL), and methanesulfonyl chloride (1.20 g, 10.44 mmol) was added at 0° C. The reaction mixture was stirred for 2 hr at 0-25° C., and then directly concentrated under reduced pressure to dryness. The residue was dissolved in N,N-dimethylformamide (50 mL), and sodium cyanide (2.81 g, 57.34 mmol) was added. The reaction mixture was heated to 60° C. and stirred for 16 hr, poured into water (500 mL), and then extracted with ethyl acetate (100 mL×2). The organic phases were combined, dried over anhydrous sodium sulfate, filtered, concentrated, and purified by flash silica gel column chromatography (petroleum ether/ethyl acetate 100-80%) to give Compound 7b (1.58 g, yellow solid, yield: 74%). ¹H NMR (400 MHz, CDCl₃) δ7.53 (d, J=7.6 Hz, 1H), 7.25-7.21 (m, 1H), 7.19-7.15 (m, 1H), 7.14-7.08 (m, 1H), 6.21 (s, 1H), 4.92-4.79 (m, 1H), 3.13-2.99 (m, 2H), 2.97-2.85 (m, 1H), 2.71-2.63 (m, 1H), 2.42-2.33 (m, 1H), 2.32-2.21 (m, 1H), 2.06-1.84 (m, 2H). MS-ESI calculated value [M+H]$^+$ 211, measured value 211.

Step III

Compound 7b (1.58 g, 6.36 mmol) was dissolved in methanol (50 mL), and hydrochloric acid/methanol solution (4 M, 42 mL) was added. The reaction mixture was stirred for 16 hr at 25-30° C., directly concentrated under reduced pressure to dryness, and then separated and purified by flash silica gel column chromatography (petroleum ether/ethyl acetate 100-90%), to give Compound 7c (1.19 g, orange solid, yield: 73%). $^1$H NMR (400 MHz, CDCl$_3$) δ7.52 (d, J=7.6 Hz, 1H), 7.31 (d, J=8.0 Hz, 1H), 7.18-7.05 (m, 2H), 6.17 (s, 1H), 5.03-4.93 (m, 1H), 3.74 (s, 3H), 3.10-2.95 (m, 2H), 2.94-2.84 (m, 1H), 2.70-2.62 (m, 1H), 2.21-2.05 (m, 2H), 1.96-1.86 (m, 2H). MS-ESI calculated value [M+H]$^+$ 244, measured value 244.

Step IV

Compound 7c (50 mg, 0.21 mmol) and Compound 1k (45 mg, 0.25 mmol) were dissolved in 1,2-dichloroethane (5 mL), and triethylsilane (119 mg, 1.03 mmol) and trifluoroacetic acid (70 mg, 0.62 mmol) were added at 0° C. The reaction mixture was stirred for 16 hr at 25° C., and water (5 mL) was added to quench the reaction. The resulting mixture was adjusted with a saturated solution of sodium bicarbonate to pH 7, and extracted with dichloromethane (10 ml×2). The organic phases were combined, dried over anhydrous sodium sulfate, filtered, and concentrated under reduced pressure to dryness to give Compound 7d (50 mg, yellow oil, yield: 59%). MS-ESI calculated value [M+H]$^+$ 412, measured value 412.

Step V

Compound 7d (50 mg, 0.12 mmol) was dissolved in methanol (5 mL), and a solution of sodium hydroxide (49 mg, 1.21 mmol) in water (5 mL) was added. The reaction mixture was heated to 80° C. and stirred for 2 hr, and then neutralized to pH 5-6 by adding 1N hydrochloric acid dropwise. Most methanol was evaporated to dryness, and the resulting mixture was extracted with ethyl acetate (25 mL×2). The organic phase was dried over anhydrous sodium sulfate, filtered, and concentrated, to give a solid crude product. The crude product was washed with ethyl acetate (5 mL×2) to give Compound 7 (30 mg, yield: 59%). $^1$H NMR (400 MHz, CD$_3$OD) δ7.81-7.79 (m, 2H), 7.46-7.43 (m, 2H), 7.35-7.31 (m, 2H), 7.11-7.08 (m, 1H), 7.01-6.95 (m, 1H), 5.00-4.92 (m, 1H), 4.20-4.09 (m, 2H), 3.06 (s, 4H), 2.92-2.84 (m, 1H), 2.80-2.70 (m, 1H), 2.70-2.61 (m, 1H), 2.20-2.13 (m, 2H), 2.00-1.91 (m, 2H). MS-ESI calculated value [M+H]$^+$ 398, measured value 398.

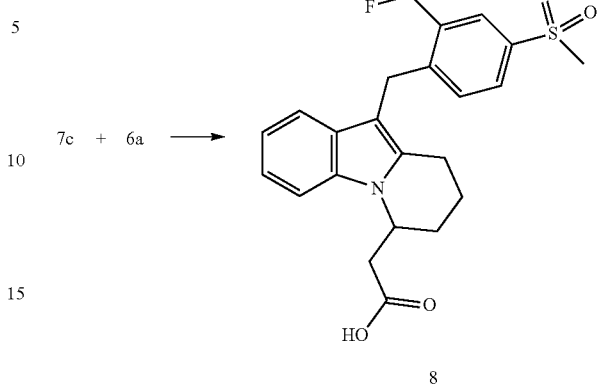

7c + 6a →

8

Example 8

Compound 8 was synthesized from Compound 7c and Compound 6a according to the method in Example 7 (67 mg, yield: 69%). $^1$H NMR (400 MHz, CD$_3$OD) δ8.24-8.23 (m, 1H), 7.96-7.90 (m, 1H), 7.38-7.36 (m, 1H), 7.27-7.25 (m, 1H), 7.19-7.17 (m, 1H), 7.14-7.10 (m, 1H), 7.00-6.95 (m, 1H), 5.04-4.96 (m, 1H), 4.32-4.31 (m, 2H), 3.13 (s, 3H), 3.01-2.86 (m, 2H), 2.77-2.64 (m, 2H), 2.23-2.13 (m, 2H), 2.08-1.89 (m, 2H). MS-ESI calculated value [M+H]$^+$ 466, measured value 466.

Example 9

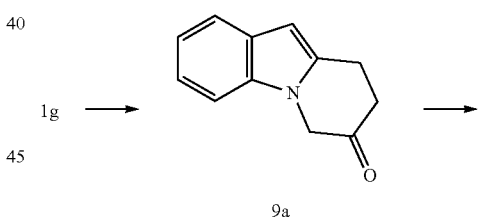

1g → 9a →

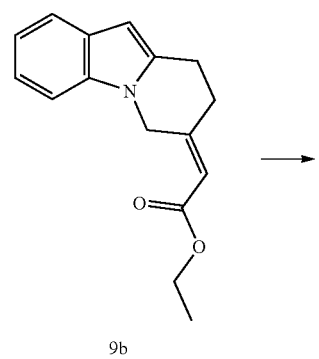

9b →

-continued

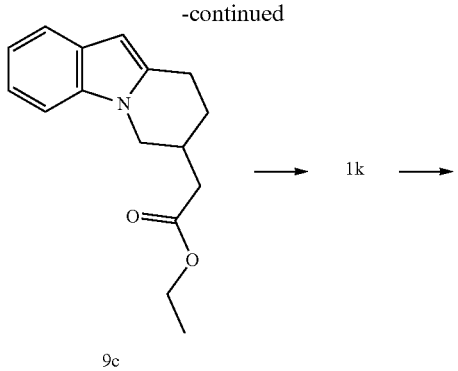

9c

→ 1k →

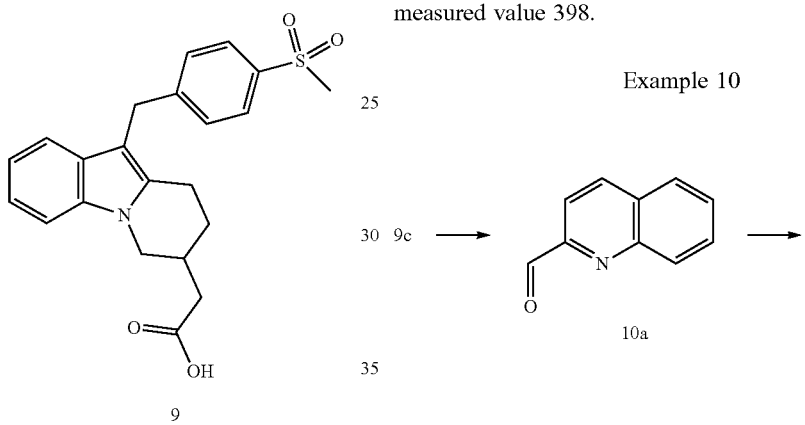

9

Step I

Compound 1g (6.00 g, 21.03 mmol) was dissolved in toluene (200 mL), and silica gel powder (30.04 g, 500.04 mmol) was added. The resulting mixture was heated to 115-120° C., and stirred for 5 hr. The reaction mixture was directly concentrated under reduced pressure to dryness, and then separated and purified by flash silica gel column chromatography (petroleum ether/ethyl acetate 100-80%), to give Compound 9a (2.56 g, yellowish solid, yield: 64%). MS-ESI calculated value [M+H]$^+$ 186, measured value 186.

Step II

Compound 9a (1.80 g, 9.72 mmol) and ethyl (triphenylphosphoranylidene)acetate (4.58 g, 13.13 mmol) were dissolved in toluene (50 mL). The reaction mixture was heated to 100° C. and stirred for 16 hr, directly concentrated, and then separated and purified by flash silica gel column chromatography (petroleum ether/ethyl acetate 100-90%), to give Compound 9b (1.32 g, yellow oil, yield: 52%). MS-ESI calculated value [M+H]$^+$ 256, measured value 256.

Step III

Compound 9b (1.32 g, 5.17 mmol) was dissolved in ethyl acetate (25 mL), and wet palladium on carbon (130 mg, 10%, moisture content: 50%) was added. The reaction mixture was stirred under a hydrogen (50 psi) atmosphere for 16 hr at 25-30° C., and filtered through celite. The filtrate was concentrated to dryness, and then separated and purified by flash silica gel column chromatography (petroleum ether/ethyl acetate 100-90%), to give Compound 9c (1.27 g, yellowish solid, yield: 93%). MS-ESI calculated value [M+H]$^+$ 258, measured value 258.

Step IV

Compound 9 was synthesized from Compound 9c and Compound 1k according to the method in Example 7 (20 mg, yield: 27%). $^1$H NMR (400 MHz, CD$_3$OD) δ7.81-7.79 (m, 2H), 7.46-7.44 (m, 2H), 7.34-7.32 (m, 1H), 7.28-7.26 (m, 1H), 7.10-7.06 (m, 1H), 7.00-6.93 (m, 1H), 4.40-4.32 (m, 1H), 4.22-4.08 (m, 2H), 3.60-3.52 (m, 1H), 3.06 (s, 4H), 2.86-2.78 (m, 1H), 2.58-2.45 (m, 3H), 2.16-7.12 (m, 1H), 1.63-1.61 (m, 1H). MS-ESI calculated value [M+H]$^+$ 398, measured value 398.

Example 10

9c →

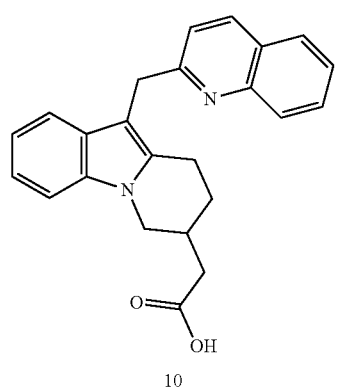

10a

→

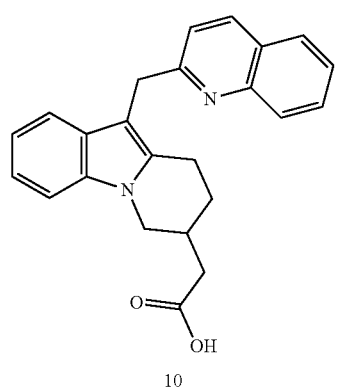

10

Compound 10 was synthesized from Compound 9c and Compound 10a according to the method in Example 7 (7 mg, yield: 10%). $^1$H NMR (400 MHz, CD$_3$OD) δ8.93-8.90 (m, 1H), 8.29-8.22 (m, 2H), 8.20-8.13 (m, 1H), 7.98-7.90 (m, 1H), 7.68-7.66 (m, 1H), 7.37-7.33 (m, 2H), 7.18-7.10 (m, 1H), 7.06-6.99 (m, 1H), 4.76-4.63 (m, 3H), 4.46-4.40 (m, 1H), 3.69-3.61 (m, 1H), 3.21-3.11 (m, 1H), 2.9-2.87 (m, 1H), 2.56-2.54 (m, 2H), 2.20-2.17 (m, 1H), 1.74-1.62 (m, 1H). MS-ESI calculated value [M+H]$^+$ 371, measured value 371.

Example 11

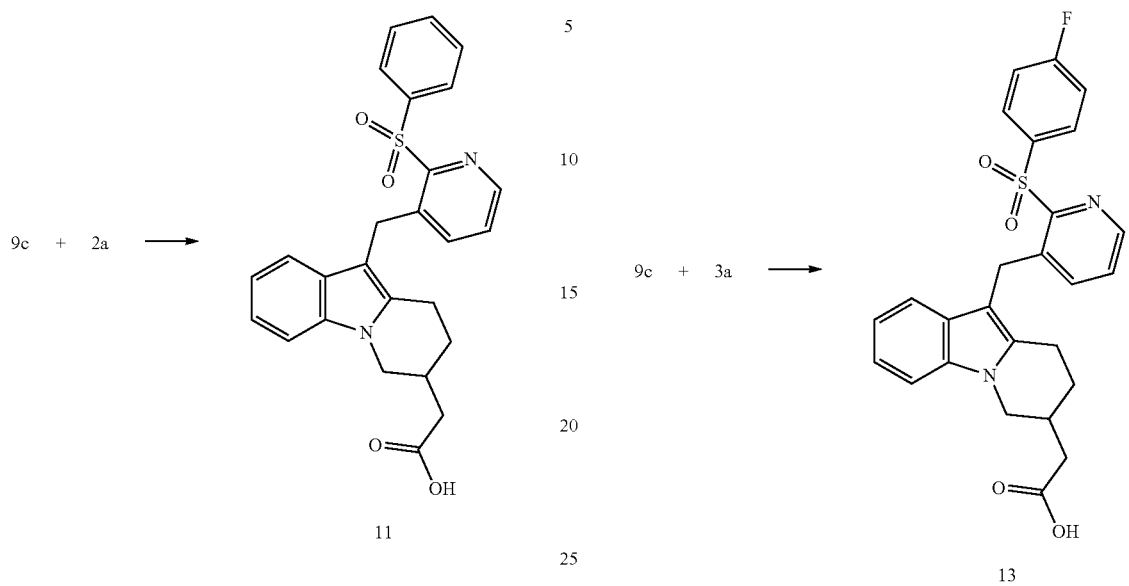

Compound 10 was synthesized from Compound 9c and Compound 2a according to the method in Example 7 (29 mg, yield: 42%). $^1$H NMR (400 MHz, CDCl$_3$) δ:8.36-8.35 (m, 1H), 8.09-8.07 (m, 2H), 7.71-7.65 (m, 1H), 7.63-7.55 (m, 2H), 7.42-7.40 (m, 1H), 7.30-7.28 (m, 1H), 7.21-7.12 (m, 3H), 7.05-6.99 (m, 1H), 4.61 (s, 2H), 4.40-4.36 (m, 1H), 3.68-3.62 (m, 1H), 2.97-2.90 (m, 1H), 2.75-2.71 (m, 1H), 2.58 (s, 3H), 2.11-2.09 (m, 1H), 1.67-1.60 (m, 1H). MS-ESI calculated value [M+H]$^+$ 461, measured value 461.

Example 12

Compound 12 was synthesized from Compound 9c and Compound 5a according to the method in Example 7 (21 mg, yield: 27%). $^1$H NMR (400 MHz, CD$_3$OD) δ7.45-7.39 (m, 1H), 7.26-7.24 (d, J=8.0 Hz, 1H), 7.16-7.14 (m, 1H), 7.09-6.96 (m, 3H), 6.95-6.90 (m, 1H), 4.35-4.27 (m, 1H), 4.14 (br. s., 2H), 3.55-3.44 (m, 1H), 2.96-2.83 (m, 1H), 2.72-2.64 (m, 1H), 2.52-2.39 (m, 3H), 2.11-2.02 (m, 1H), 1.62-1.44 (m, 1H). MS-ESI calculated value [M+H]$^+$ 406, measured value 406.

Example 13

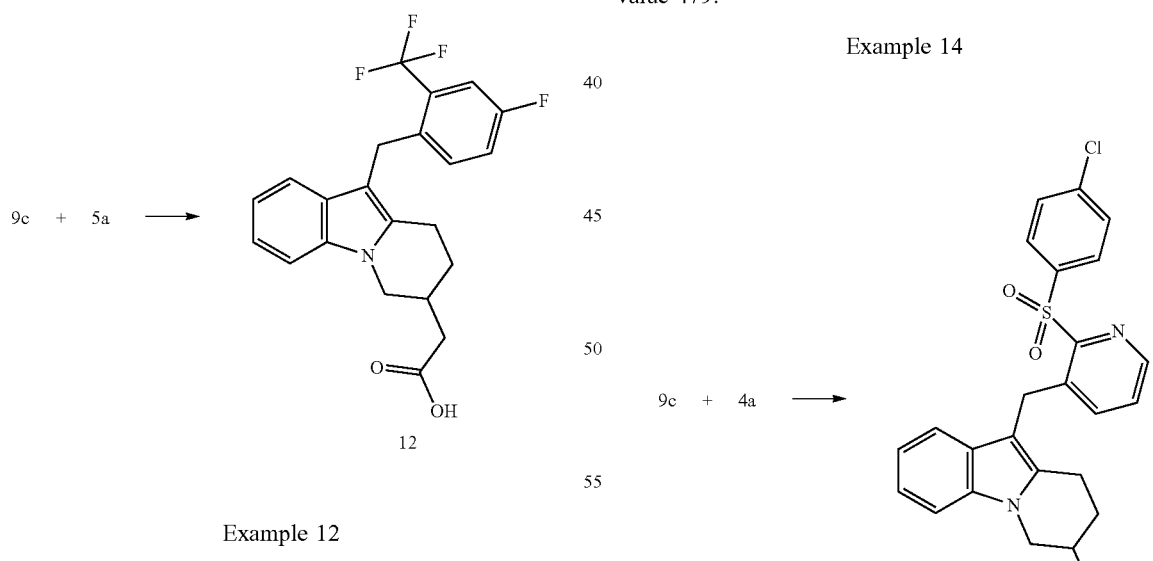

Compound 13 was synthesized from Compound 9c and Compound 3a according to the method in Example 7 (39 mg, yield: 69%). $^1$H NMR (400 MHz, CD$_3$OD) δ8.34-8.32 (m, 1H), 8.06-8.02 (m, 2H), 7.54-7.46 (m, 3H), 7.45-7.40 (m, 1H), 7.32-7.30 (m, 1H), 7.14-7.12 (m, 1H), 7.06-7.02 (m, 1H), 6.94-6.87 (m, 1H), 4.58-4.46 (m, 2H), 4.35-4.27 (m, 1H), 3.59-3.57 (m, 1H), 2.98-2.90 (m, 1H), 2.76-2.67 (m, 1H), 2.45-2.30 (m, 3H), 2.02-1.99 (m, 1H), 1.56-1.54 (m, 1H). MS-ESI calculated value [M+H]$^+$ 479, measured value 479.

Example 14

Compound 14 was synthesized from Compound 9c and Compound 4a according to the method in Example 7 (39 mg, yield: 69%). ¹H NMR (400 MHz, CDCl₃) δ8.33-8.30 (m, 1H), 8.01-7.98 (m, 2H), 7.56-7.53 (m, 2H), 7.47-4.43 (m, 1H), 7.31-7.29 (m, 1H), 7.23-7.13 (m, 3H), 7.08-7.01 (m, 1H), 4.64 (s, 2H), 4.43-4.34 (m, 1H), 3.68-3.63 (m, 1H), 2.99-2.95 (m, 1H), 2.79-2.71 (m, 1H), 2.65-2.47 (m, 3H), 2.18-2.06 (m, 1H), 1.65-1.63 (m, 1H). MS-ESI calculated value [M+H]⁺ 495, measured value 495.

Example 15

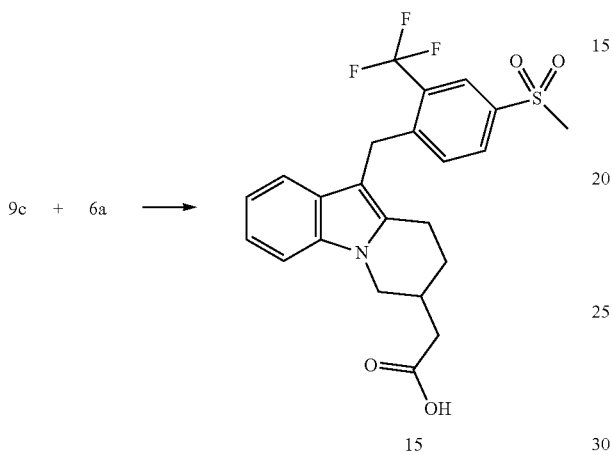

15

Compound 15 was synthesized from Compound 9c and Compound 6a according to the method in Example 7 (67 mg, yield: 73%). ¹H NMR (400 MHz, CD₃OD) δ8.25-8.24 (m, 1H), 7.94-7.88 (m, 1H), 7.35-7.25 (m, 2H), 7.17-7.14 (m, 1H), 7.13-7.05 (m, 1H), 6.99-6.93 (m, 1H), 4.42-4.38 (m, 1H), 4.37-4.26 (m, 2H), 3.63-3.57 (m, 1H), 3.13 (s, 3H), 2.99-2.95 (m, 1H), 2.80-2.74 (m, 1H), 2.60-2.46 (m, 3H), 2.18-2.06 (m, 1H), 1.70-1.56 (m, 1H). MS-ESI calculated value [M+H]⁺ 466, measured value 466.

Example 16

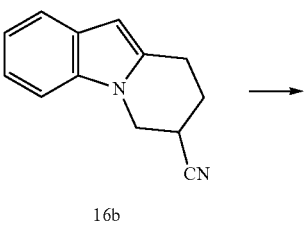

16a

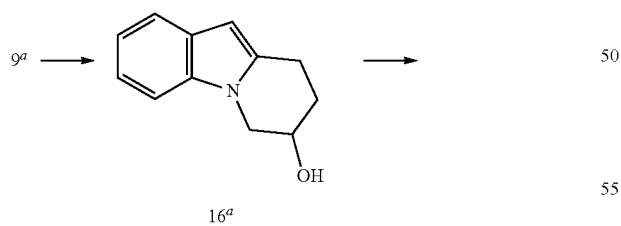

16b

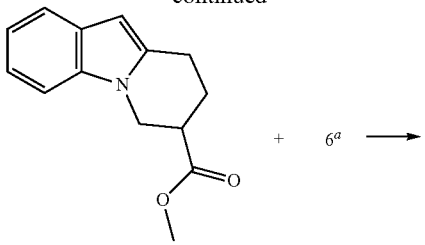

16c

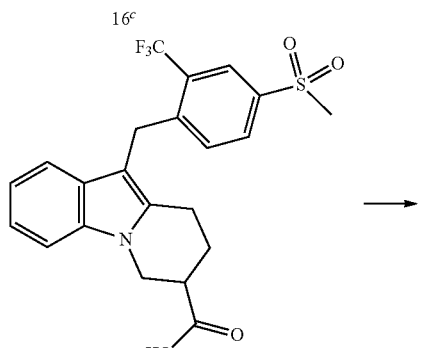

16

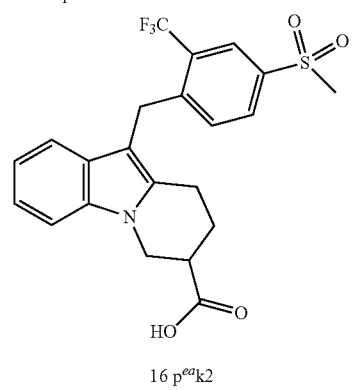

16 peak1

16 peak2

Step I

Compound 9a (2.20 g, 11.88 mmol) was dissolved in tetrahydrofuran (50 mL), and sodium borohydride (449 mg, 11.88 mmol) was added in batch at 0° C. The reaction mixture was warmed to 25-30° C. and stirred for 0.5 hr, and then 1 N hydrochloric acid solution was added dropwise to quench the reaction and adjust the pH to 6-7. Most tetrahydrofuran was evaporated, and the resulting mixture was extracted with ethyl acetate (100 mL×2). The organic phases were combined, dried over anhydrous sodium sulfate, filtered, and concentrated to give Compound 16a (2.20 g, yellow oil, crude produce). MS-ESI calculated value [M+H]$^+$ 188, measured value 188.

Step II

Compound 16b was obtained from Compound 16a according to the synthesis method of Compound 7b (380 mg, yellow solid, yield: 15%). MS-ESI calculated value [M+H]$^+$ 197, measured value 197.

Step III

Compound 16c was obtained from Compound 16b according to the synthesis method of Compound 7c (440 mg, red crude product). MS-ESI calculated value [M+H]$^+$ 230, measured value 230.

Step IV

Compound 16 was synthesized from Compound 16c and Compound 6a according to the synthesis method of Compound 7 (45 mg, yield: 46%). $^1$H NMR (400 MHz, CD$_3$OD) δ8.24 (s, 1H), 7.96-7.88 (m, 1H), 7.38-7.36 (m, 1H), 7.29-7.27 (m, 1H), 7.18-7.16 (m, 1H), 7.13-7.11 (m, 1H), 7.01-6.94 (m, 1H), 4.46-4.38 (m, 1H), 4.32 (s, 2H), 4.18-4.10 (m, 1H), 3.13 (s, 4H), 3.04-2.92 (m, 1H), 2.89-2.81 (m, 1H), 2.42-2.29 (m, 1H), 2.11-1.97 (m, 1H). MS-ESI calculated value [M+H]$^+$ 452, measured value 452.

Step V

Enantiomer compounds were obtained by chiral resolution of Compound 16.

SFC chiral resolution conditions:

Column: ChiralCel OJ-H 150×4.6 mm I.D. 5 μm

Mobile phase: A: Carbon dioxide, B: Methanol (0.05% diethylamine)

Gradient: Mobile phase B was improved from 5% to 40% in 5.5 min, maintained at 40% for 3 min, and then maintained at 5% for 1.5 min.

Flow rate: 2.5 mL/min

Column temperature: 40° C.

Relative retention time of 16 peak1: 5.086 min. $^1$H NMR (400 MHz, CD$_3$OD) δ8.23 (s, 1H), 7.91 (d, J=8.4 Hz, 1H), 7.35 (d, J=8.4 Hz, 1H), 7.28 (d, J=8.4 Hz, 1H), 7.16 (d, J=7.6 Hz, 1H), 7.09 (d, J=7.6 Hz, 1H), 6.97 (d, J=7.6 Hz, 1H), 4.43-4.39 (m, 1H), 4.31 (s, 2H), 4.14-4.08 (m, 1H), 3.12 (s, 3H), 3.01-2.79 (m, 2H), 2.31 (brs, 1H), 2.03-1.99 (m, 2H). MS-ESI calculated value [M+H]$^+$ 452, measured value 452.

Relative retention time of 16 peak2: 5.342 min. $^1$H NMR (400 MHz, CD$_3$OD) δ8.24 (s, 1H), 7.92 (d, J=8.0 Hz, 1H), 7.36 (d, J=8.4 Hz, 1H), 7.29 (d, J=8.0 Hz, 1H), 7.16 (d, J=8.0 Hz, 1H), 7.09 (d, J=7.2 Hz, 1H), 6.98 (d, J=7.2 Hz, 1H), 4.43-4.39 (m, 1H), 4.32 (s, 2H), 4.14-4.09 (m, 1H), 3.13 (s, 3H), 3.01-2.80 (m, 2H), 2.32 (brs, 1H), 2.03-1.93 (m, 2H). MS-ESI calculated value [M+H]$^+$ 452, measured value 452.

Example 17

16$^c$ + 4$^a$ ⟶

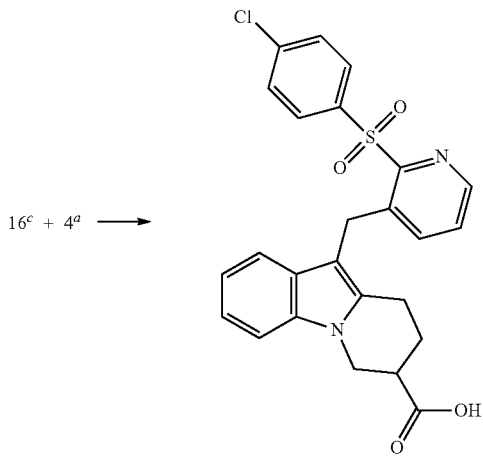

17

Compound 17 was synthesized from Compound 16c and Compound 4a according to the synthesis method of Compound 7 (52 mg, yield: 54%). $^1$H NMR (400 MHz, CD$_3$OD) δ8.36-8.34 (m, 1H), 7.91-7.88 (m, 2H), 7.61-7.59 (m, 2H), 7.56-7.53 (m, 1H), 7.42-7.34 (m, 1H), 7.33-7.31 (m, 1H), 7.11-7.08 (m, 1H), 7.03-7.01 (m, 1H), 6.96-6.88 (m, 1H), 4.55-7.54 (m, 2H), 4.41-4.33 (m, 1H), 4.15-4.06 (m, 1H), 3.07 (br. s., 1H), 2.98-2.87 (m, 1H), 2.82-2.68 (m, 1H), 2.32-2.29 (m, 1H), 2.04-1.98 (m, 1H). MS-ESI calculated value [M+H]$^+$ 481, measured value 481.

Example 18

16$^c$ ⟶ 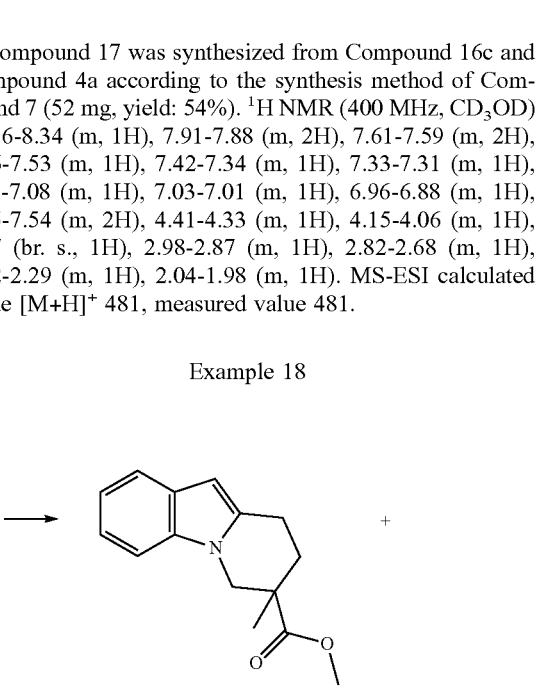

6$^a$ ⟶ 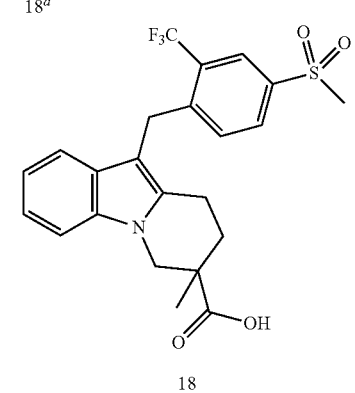

18

Step I

Compound 16c (237 mg, 1.03 mmol) was dissolved in tetrahydrofuran (10 mL), and then the reaction mixture was cooled to −78° C., and lithium diisopropylamide (1.55 mmol, 0.77 mL) was slowly added dropwise. After completion of the addition, the resulting mixture was stirred for 0.5 hr at −78° C., and then iodomethane (0.4 mL, 6.34 mmol) was slowly added dropwise. After completion of the addition, the resulting mixture was stirred for 50 min at −78° C., then slowly warmed to the room temperature, and stirred for 2 hr. 1 mL of water was slowly added to the reaction system to quench the reaction. The resulting mixture was adjusted with a saturated solution of ammonium chloride to pH 7, and extracted with ethyl acetate (50 mL×2). The organic phases were combined, dried over anhydrous sodium sulfate, filtered, concentrated under reduced pressure to dryness, and purified by chromatography on silica gel plates (petroleum ether/ethyl acetate=4/1) to give Compound 18a (180 mg, yellow solid, yield: 72%). $^1$H NMR (400 MHz, CDCl$_3$) δ7.54-7.52 (m, 1H), 7.33-7.31 (m, 1H), 7.19-7.07 (m, 2H), 6.23-6.22 (m, 1H), 4.56-4.53 (m, 1H), 3.79-3.77 (m, 1H), 3.72 (s, 3H), 3.08-2.96 (m, 2H), 2.38-2.29 (m, 1H), 1.90 (m, 1H), 1.42 (s, 3H). MS-ESI calculated value [M+H]$^+$ 244, measured value 244.

Step II

Compound 18 was synthesized from Compound 18a and Compound 6a according to the synthesis method of Compound 7 (10 mg, yield: 11%). $^1$H NMR (400 MHz, DMSO-d$_6$) δ8.19 (s, 1H), 8.01-7.99 (m, 1H), 7.44-7.42 (m, 1H), 7.21-7.18 (m, 2H), 7.09-7.07 (m, 1H), 6.99-6.93 (m, 1H), 4.54-4.51 (m, 1H), 4.25 (s, 2H), 3.78-3.75 (m, 1H), 3.27 (s, 3H), 2.95-2.86 (m, 1H), 2.80-2.66 (m, 1H), 2.25-2.18 (m, 1H), 1.91-1.82 (m, 1H), 1.35 (s, 3H). MS-ESI calculated value [M+H]$^+$ 466, measured value 466.

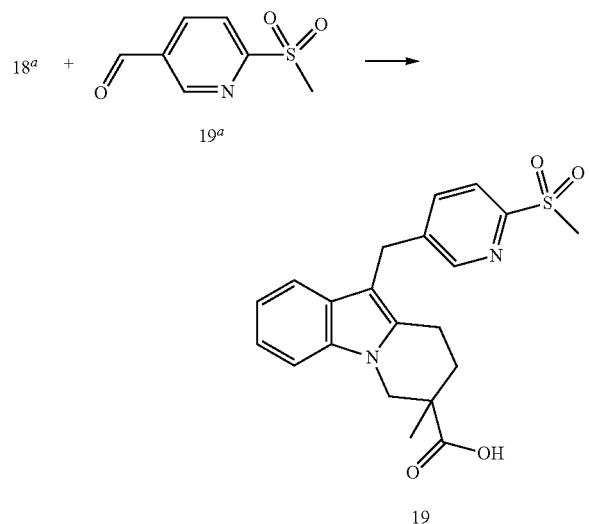

Example 19

Compound 19 was synthesized from Compound 18a and Compound 19a according to the synthesis method of Compound 7 (130 mg, yield: 15%). $^1$H NMR (400 MHz, DMSO-d$_6$) δ8.67 (s, 1H), 7.95-7.84 (m, 2H), 7.47-7.33 (m, 2H), 7.10-6.95 (m, 2H), 4.50-4.47 (m, 1H), 4.13 (s, 2H), 3.72-3.69 (m, 1H), 3.21 (s, 3H), 3.08-3.06 (m, 1H), 2.88-2.79 (m, 1H), 2.28-2.20 (m, 1H), 1.90-1.81 (m, 1H), 1.34 (s, 3H). MS-ESI calculated value [M+H]$^+$ 399, measured value 399.

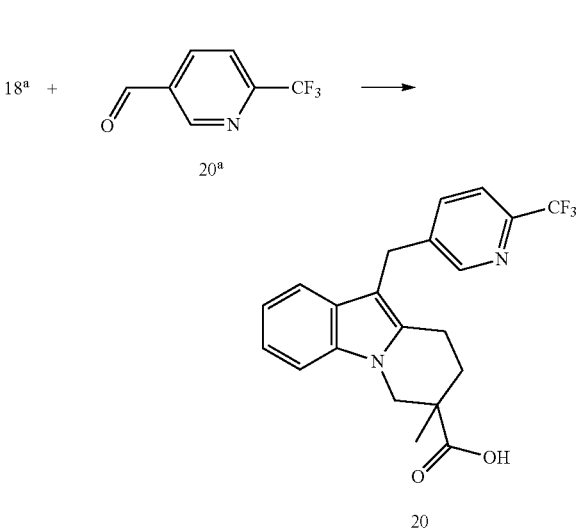

Example 20

Compound 20 was synthesized from Compound 18a and Compound 20a according to the synthesis method of Compound 7 (24 mg, yield: 55%). $^1$H NMR (400 MHz, CD$_3$OD) δ8.55 (s, 1H), 7.77-7.75 (m, 1H), 7.66-7.64 (m, 1H), 7.34-7.31 (m, 2H), 7.11-7.08 (m, 1H), 7.02-6.99 (m, 1H), 4.60-4.56 (m, 1H), 4.16 (s, 2H), 3.73-3.70 (m, 1H), 3.05-2.91 (m, 2H), 2.38-2.35 (m, 1H), 1.92-1.88 (m, 1H), 1.42 (s, 3H). MS-ESI calculated value [M+H]$^+$ 389, measured value 389.

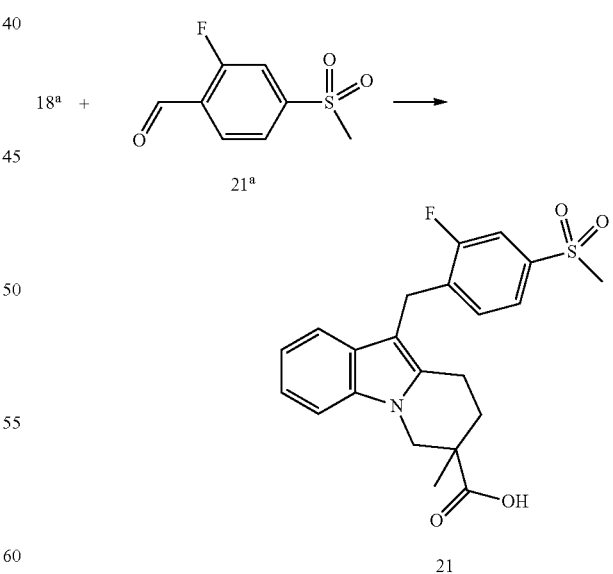

Example 21

Compound 21 was synthesized from Compound 18a and Compound 21a according to the synthesis method of Compound 7 (30 mg, yield: 66%). $^1$H NMR (400 MHz, CD$_3$OD) δ7.66-7.63 (m, 1H), 7.59-7.56 (m, 1H), 7.34-7.31 (m, 3H), 7.09-7.07 (m, 1H), 7.00-6.97 (m, 1H), 4.59-4.55 (m, 1H), 4.13 (s, 2H), 3.73-3.69 (m, 1H), 3.01 (s, 3H), 2.95-2.91 (m, 2H), 2.38-2.35 (m, 1H), 1.90-1.87 (m, 1H), 1.42 (s, 3H). MS-ESI calculated value [M+H]$^+$ 416, measured value 416.

Example 22

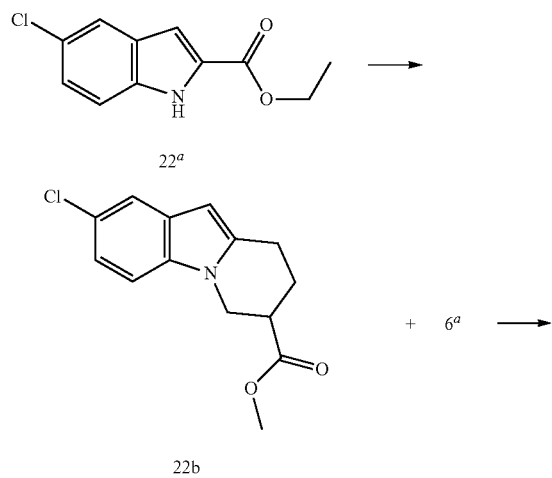

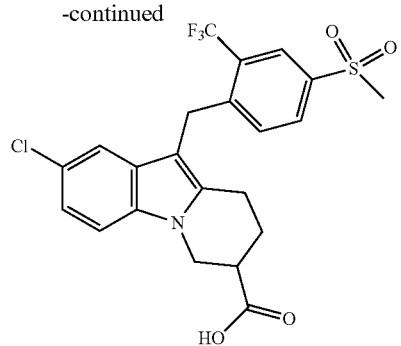

Step I

Compound 22b was obtained from Compound 22a via a multi-step reaction according to the methods in Example 1, Example 9, and Example 16 (405 mg, yellow solid, yield: 89%). MS-ESI calculated value [M+H]$^+$ 264, measured value 264.

Step II

Compound 22 was synthesized from Compound 22b and Compound 6a according to the synthesis method of Compound 7 (17 mg, yield: 21%). $^1$H NMR (400 MHz, CD$_3$OD) δ8.26 (s, 1H), 7.99-7.93 (m, 1H), 7.37-7.35 (m, 1H), 7.27-7.25 (m, 1H), 7.13-7.12 (m, 1H), 7.09-7.07 (m, 1H), 4.42-4.38 (m, 1H), 4.30 (s, 2H), 4.19-4.14 (m, 1H), 3.23-3.15 (m, 1H), 3.14 (s, 3H), 3.03-2.93 (m, 1H), 2.89-2.77 (m, 1H), 2.40-2.28 (m, 1H), 2.14-1.99 (m, 1H). MS-ESI calculated value [M+H]$^+$ 486, measured value 486.

Step III

Enantiomer compounds were obtained by chiral resolution of Compound 22.

SFC chiral resolution conditions:

Column: (R,R)Whelk-01 100×4.6 mm 3 μm

Gradient: 40% ethanol containing 0.05% diethylamine and carbon dioxide

Flow rate: 2.5 mL/min

Column temperature: 40° C.

Retention time of 22 peak1: 5.930 min; $^1$H NMR (400 MHz, DMSO-d$_6$) δ8.19 (s, 1H), 8.01 (d, J=8.0 Hz, 1H), 7.47 (d, J=8.4 Hz, 1H), 7.25-7.23 (m, 2H), 7.10-7.08 (m, 1H), 4.38-4.35 (m, 1H), 4.24 (s, 2H), 4.12-4.05 (m, 1H), 3.27 (s, 3H), 3.10-3.07 (m, 1H), 2.86-2.77 (m, 2H), 2.22-2.19 (m, 1H), 1.93-1.91 (m, 1H). MS-ESI calculated value [M+H]$^+$ 486, measured value 486.

Retention time of 22 peak2: 3.659; $^1$H NMR (400 MHz, CD$_3$OD) δ8.25 (s, 1H), 7.96-7.93 (m, 1H), 7.36-7.34 (m, 1H), 7.28-7.26 (m, 1H), 7.13-7.07 (m, 2H), 4.42-4.37 (m, 1H), 4.29 (s, 2H), 4.18-4.13 (m, 1H), 3.18-3.17 (m, 1H), 3.14 (s, 3H), 2.99-2.83 (m, 2H), 2.33-2.31 (m, 1H), 2.05-2.03 (m, 1H). MS-ESI calculated value [M+H]$^+$ 486, measured value 486.

Example 23

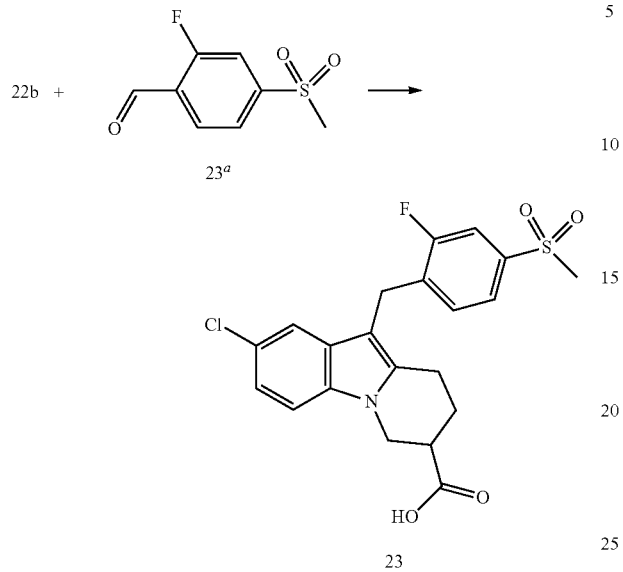

Compound 23 was synthesized from Compound 22b and Compound 23a according to the synthesis method of Compound 7 (25 mg, yield: 42%). ¹H NMR (400 MHz, CD₃OD) δ7.72-7.70 (m, 1H), 7.65-7.63 (m, 1H), 7.52-7.45 (m, 2H), 7.43-7.41 (m, 1H), 7.07-7.05 (m, 1H), 4.33-4.28 (m, 1H), 4.14-3.98 (m, 3H), 3.21 (s, 3H), 3.14-3.05 (m, 1H), 3.05-2.95 (m, 1H), 2.92-2.79 (m, 1H), 2.27-2.16 (m, 1H), 1.94-1.92 (m, 1H). MS-ESI calculated value [M+H]⁺ 436, measured value 436.

Example 24

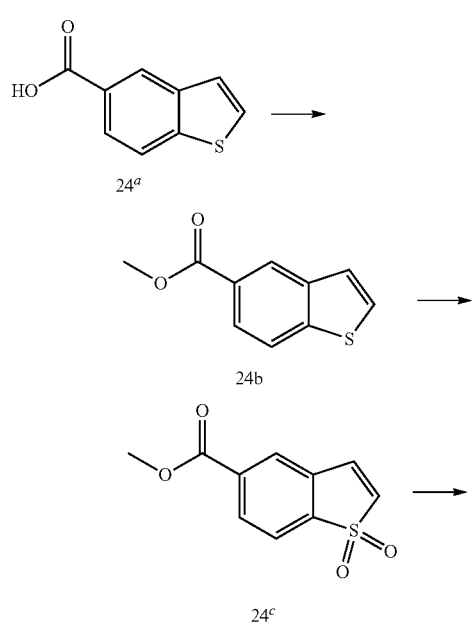

Step I

Compound 24a (1.32 g, 7.41 mmol) was dissolved in methanol (35 mL), and sulfoxide chloride (1.32 g, 11.12 mmol) was added in batch. The reaction mixture was heated to 60° C. and stirred for 4 hr, and directly concentrated to dryness, to give Compound 24b (1.40 g, white solid, yield: 97%). ¹H NMR (400 MHz, CDCl₃) δ8.54 (d, J=1.2 Hz, 1H), 8.03-7.98 (m, 1H), 7.95-7.90 (m, 1H), 7.52 (d, J=5.6 Hz, 1H), 7.43 (d, J=5.6 Hz, 1H), 3.96 (s, 3H).

Step II

Compound 24b (1.40 g, 7.28 mmol) was dissolved in dichloromethane (50 mL), and m-chloroperoxybenzoic acid (4.43 g, 21.84 mmol, 80%) was added at 0° C. The reaction mixture was stirred for 16 hr at 30° C., and then a saturated solution of sodium thiosulfate (20 mL) was added to quench the reaction. The pH of the resulting mixture was adjusted with a sodium carbonate solution to 7-8. The organic phase was washed with a saturated aqueous solution of sodium bicarbonate (50 mL), dried over anhydrous sodium sulfate, filtered, and concentrated under reduced pressure to dryness, to give Compound 24c (1.73 g, white solid, yield: 89%). ¹H NMR (400 MHz, CDCl₃) δ8.26-8.18 (m, 1H), 8.03 (s, 1H), 7.80 (d, J=7.6 Hz, 1H), 7.28 (d, J=7.2 Hz, 1H), 6.80 (d, J=6.8 Hz, 1H), 3.97 (s, 3H).

Step III

Compound 24c (200 mg, 0.89 mmol) was dissolved in methanol (20 mL), and wet palladium on carbon (20 mg, 10%, moisture content: 50%) was added. The reaction mixture was stirred under a hydrogen (15 psi) atmosphere for 16 hr at the room temperature, and then filtered. The filtrate was concentrated under reduced pressure to dryness, to give Compound 24d (200 mg, white solid, yield: 99%). $^1$H NMR (400 MHz, CD$_3$OD) δ8.16-8.11 (m, 2H), 7.80 (d, J=8.4 Hz, 1H), 3.95 (s, 3H), 3.62-3.56 (m, 2H), 3.48-3.43 (m, 2H).

Step IV

Compound 24d (150 mg, 0.66 mmol) was dissolved in tetrahydrofuran (5 mL), and a solution of diisobutyl aluminum hydride in toluene (or dichloromethane) (2.65 mmol, 1 M, 2.65 mL) was slowly added dropwise at 5-15° C. The reaction mixture was stirred at this temperature for 4 hr, and then water (10 mL) and 1 N hydrochloric acid (5 mL) were successively added. The resulting mixture was extracted with ethyl acetate (20 mL×2). The organic phases were combined, dried over anhydrous sodium sulfate, filtered, concentrated under reduced pressure to dryness, and separated and purified by thin-layer silica gel chromatoplates (petroleum ether/ethyl acetate=1/1) to give Compound 24e (80 mg, white solid, yield: 60%). $^1$H NMR (400 MHz, CD$_3$OD) δ7.66 (d, J=7.6 Hz, 1H), 7.52-7.46 (m, 2H), 4.70 (s, 2H), 3.58-3.50 (m, 2H), 3.43-3.36 (m, 2H).

Step V

Compound 24e (80.00 mg, 403.55 mmol) was dissolved in dichloromethane (10 mL), and manganese dioxide (281 mg, 3.23 mmol) was added. The reaction mixture was stirred for 3 hr at the room temperature, and then filtered. The filtrate was directly concentrated to dryness to give Compound 24f (71 mg, white solid, yield: 89%). $^1$H NMR (400 MHz, CDCl$_3$) δ10.10 (s, 1H), 8.02-7.96 (m, 1H), 7.95-7.89 (m, 2H), 3.62-3.45 (m, 4H).

Step VI

Compound 24 was synthesized from Compound 24f and Compound 22b according to the method in Example 7 (34 mg, yield: 56%). $^1$H NMR (400 MHz, CD$_3$OD) δ7.63-7.61 (m, 1H), 7.47-7.46 (m, 1H), 7.43-7.40 (m, 1H), 7.37-7.34 (m, 1H), 7.32 (s, 1H), 7.06-7.04 (m, 1H), 4.34-4.30 (m, 1H), 4.13-3.97 (m, 3H), 3.57-3.48 (m, 2H), 3.29-3.23 (m, 2H), 3.14-3.06 (m, 1H), 3.04-2.98 (m, 1H), 2.93-2.81 (m, 1H), 2.28-2.17 (m, 1H), 1.99-1.85 (m, 1H). MS-ESI calculated value [M+H]$^+$ 430, measured value 430.

Example 25

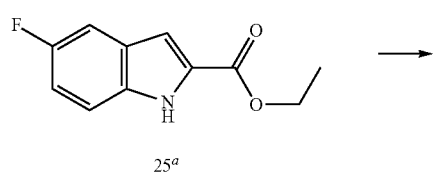

25$^a$

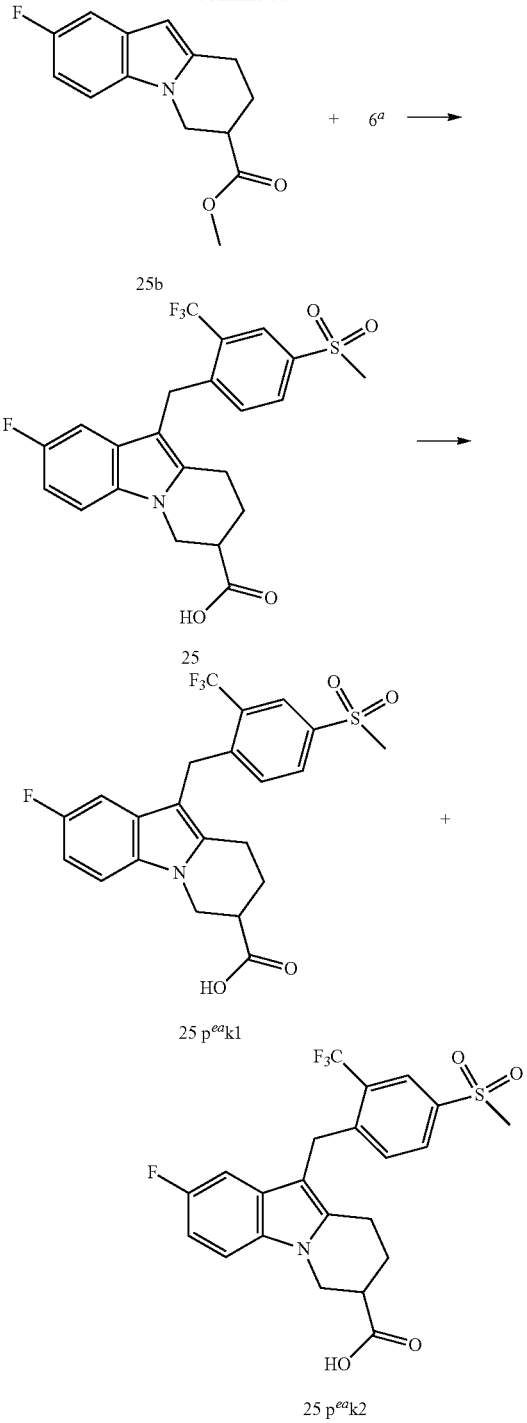

Step I

Compound 25b was obtained from Compound 25a via a multi-step reaction according to the methods in Example 1, Example 9, and Example 16 (950 mg, white solid, yield: 69%). $^1$H NMR (400 MHz, CDCl$_3$) δ7.27-7.16 (m, 2H), 6.91-6.89 (m, 1H), 6.18 (s, 1H), 4.41-4.36 (m, 1H), 4.10-4.05 (m, 1H), 3.79 (s, 3H), 3.15-3.07 (m, 3H), 2.35-2.33 (m, 1H), 2.01-1.97 (m, 1H). MS-ESI calculated value [M+H]$^+$ 248, measured value 248.

Step II

Compound 25 was synthesized from Compound 25b and Compound 6a according to the synthesis method of Compound 7 (64 mg, yield: 56%). $^1$H NMR (400 MHz, CD$_3$OD) δ8.27-8.26 (m, 1H), 7.97-7.95 (m, 1H), 7.37-7.34 (m, 1H), 7.31-7.29 (m, 1H), 6.88-6.82 (m, 2H), 4.44-4.40 (m, 1H), 4.31 (s, 2H), 6.19-4.14 (m, 1H), 3.16-3.13 (m, 4H), 3.01-2.95 (m, 1H), 2.87-2.84 (m, 1H), 2.34-2.33 (m, 1H), 2.07-2.05 (m, 1H). MS-ESI calculated value [M+H]$^+$ 470, measured value 470.

Step III

Compounds were obtained by chiral resolution of Compound 25.

SFC chiral resolution conditions:
Column: (R,R)Whelk-01 100×4.6 mm 3 μm
Gradient: 40% ethanol containing 0.05% diethylamine and carbon dioxide
Flow rate: 2.5 mL/min
Column temperature: 40° C.

Retention time of 25 peak1: 2.731 min; $^1$H NMR (400 MHz, CD$_3$OD) δ8.25 (s, 1H), 7.95 (d, J=8.4 Hz, 1H), 7.36-7.32 (m, 1H), 7.28 (d, J=8.4 Hz, 1H), 6.87-6.81 (m, 2H), 4.42-4.38 (m, 1H), 4.29 (s, 2H), 4.17-4.12 (m, 1H), 3.14-3.12 (m, 4H), 2.99-2.83 (m, 2H), 2.32-2.31 (m, 1H), 2.06-2.02 (m, 1H). MS-ESI calculated value [M+H]$^+$ 470, measured value 470.

Retention time of 25 peak2: 4.038 min; $^1$H NMR (400 MHz, CD$_3$OD) δ8.27 (s, 1H), 7.95 (d, J=8.4 Hz, 1H), 7.37-7.34 (m, 1H), 7.30 (d, J=8.4 Hz, 1H), 6.89-6.83 (m, 2H), 4.44-4.40 (m, 1H), 4.31 (s, 2H), 4.19-4.14 (m, 1H), 3.16-3.14 (m, 4H), 3.01-2.84 (m, 2H), 2.36-2.33 (m, 1H), 2.08-2.04 (m, 1H). MS-ESI calculated value [M+H]$^+$ 470, measured value 470.

Example 26

25b + 23$^a$ ⟶

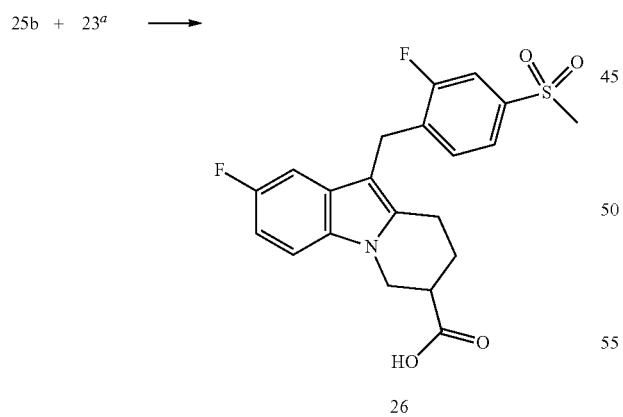

26

Compound 26 was synthesized from Compound 25b and Compound 23a according to the synthesis method of Compound 7 (43 mg, yield: 73%). $^1$H NMR (400 MHz, CD$_3$OD) δ7.67-7.65 (m, 1H), 7.63-7.60 (m, 1H), 7.38-7.33 (m, 1H), 7.30-7.27 (m, 1H), 7.04-7.00 (m, 1H), 6.87-6.82 (m, 1H), 4.38-4.33 (m, 1H), 4.15-4.06 (m, 3H), 3.16-3.04 (m, 5H), 2.94-2.84 (m, 1H), 2.39-2.30 (m, 1H), 2.10-1.98 (m, 1H). MS-ESI calculated value [M+H]$^+$ 420, measured value 420.

Example 27

25b + 10$^a$ ⟶

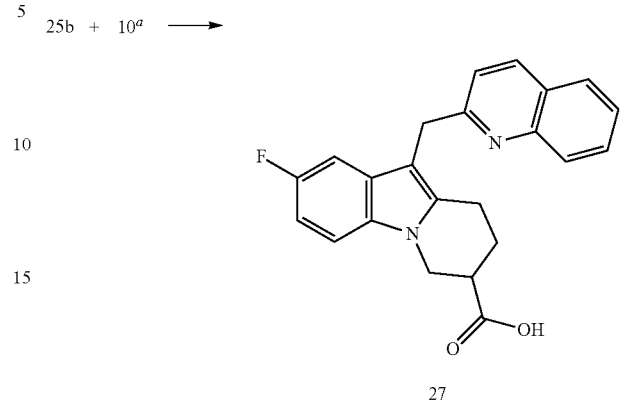

27

Compound 27 was synthesized from Compound 25b and Compound 10a according to the method in Example 7 (12 mg, yield: 46%). $^1$H NMR (400 MHz, CD$_3$OD) δ:8.89-8.87 (m, 1H), 8.31-8.29 (m, 1H), 8.24-8.22 (m, 1H), 8.16-8.12 (m, 1H), 7.95-7.87 (m, 1H), 7.62-7.60 (m, 1H), 7.38-7.34 (m, 1H), 7.10-7.07 (m, 1H), 6.92-6.87 (m, 1H), 4.67 (s, 2H), 4.40-4.36 (m, 1H), 4.19-4.14 (m, 1H), 3.20-3.06 (m, 2H), 3.00-2.89 (m, 1H), 2.40-2.31 (m, 1H), 2.15-2.01 (m, 1H). MS-ESI calculated value [M+H]$^+$ 375, measured value 375.

25b + 24f ⟶

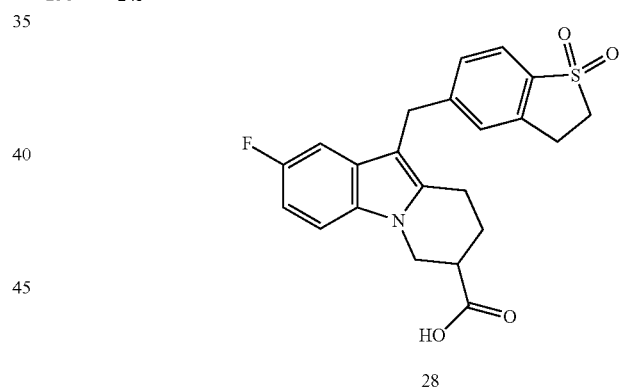

28

Example 28

Compound 28 was synthesized from Compound 25b and Compound 24f according to the method in Example 7 (62 mg, yield: 80%). $^1$H NMR (400 MHz, CD$_3$OD) δ7.59-7.56 (m, 1H), 7.36-7.36 (m, 1H), 7.33-7.26 (m, 1H), 7.02-6.98 (m, 1H), 6.89-6.83 (m, 1H), 4.40-4.35 (m, 1H), 4.17-4.07 (m, 3H), 3.52-3.48 (m, 2H), 3.32-3.30 (m, 2H), 3.18-3.03 (m, 2H), 2.92-2.84 (m, 1H), 2.41-2.30 (m, 1H), 2.09-2.01 (m, 1H). MS-ESI calculated value [M+H]$^+$ 414, measured value 414.

Example 29

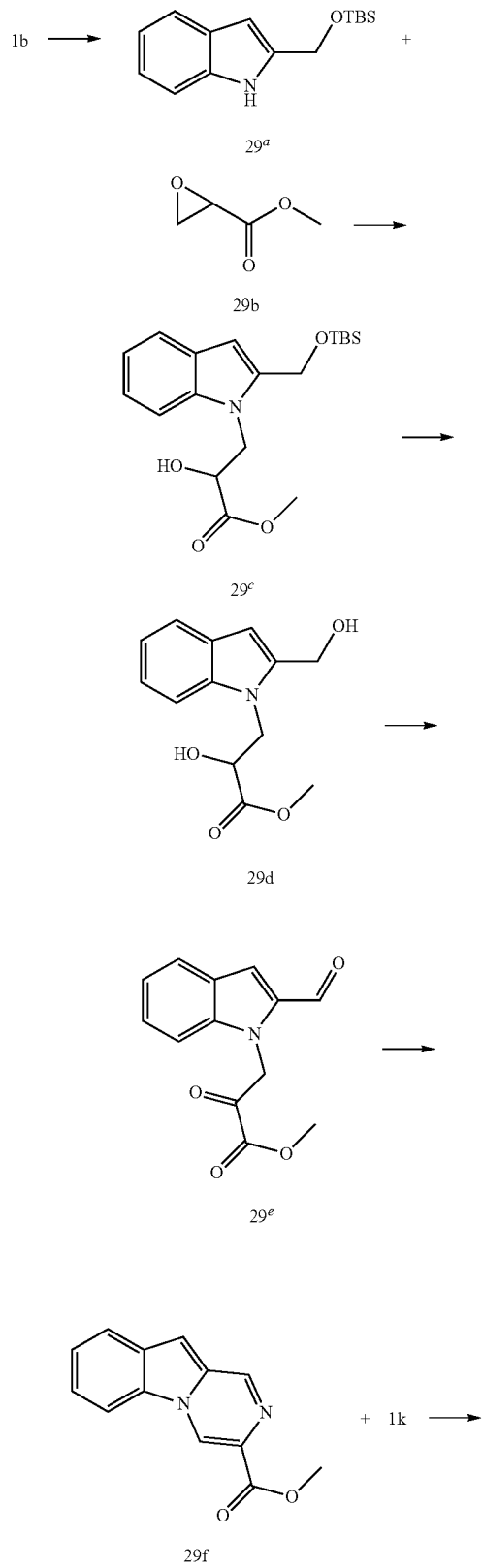

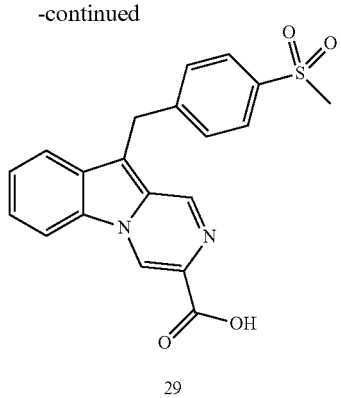

Step I

At 0° C., N,N-diisopropylethylamine (84.30 g, 652.30 mmol) was added to a solution of Compound 1b (64.00 g, 434.87 mmol) in N,N-dimethylformamide (600 mL), and t-butyldimethylsilyl chloride (78.65 g, 521.84 mmol) was slowly added in batch. The resulting mixture was stirred for 1 hr at 0° C. Water (600 mL) was added to the reaction mixture to quench the reaction, and the resulting mixture was extracted with ethyl acetate (300 mL×3). The organic phase was washed with saturated brine (100 mL×3), dried over anhydrous sodium sulfate, filtered, and concentrated under reduced pressure to give a crude product. The crude product was purified by silica gel column chromatography (ethyl acetate/petroleum ether, 95%-90%) to give Compound 29a (109.00 g, yellowish solid, 96%). $^1$H NMR (400 MHz, CDCl$_3$) δ8.29 (br. s., 1H), 7.58-7.56 (m, 1H), 7.39-7.37 (m, 1H), 7.18-7.15 (m, 1H), 7.09 (m, 1H), 6.32 (s, 1H), 4.89 (s, 2H), 0.95 (s, 9H), 0.12 (s, 6H).

Step II

At 0° C., sodium hydride (1.99 g, 49.70 mmol, 60%) was added to a solution of Compound 29a (10.00 g, 38.2 mmol) in N,N-dimethylformamide (40 mL). The resulting mixture was stirred for 5 min, and then a solution of methyl glycidate 29b (7.81 g, 76.50 mmol) in N,N-dimethylformamide (10 mL) was added. The resulting mixture was stirred for 3 hr at 0° C. The reaction mixture was diluted with ethyl acetate (200 mL), washed successively with a saturated aqueous solution of ammonium chloride (100 mL×2) and saturated brine (100 mL×2), dried over anhydrous sodium sulfate, and filtered to remove the drying agent. The solvent was removed from the filtrate under reduced pressure. The residue was purified by silica gel column chromatography (petroleum ether/ethyl acetate 100-50%) to give Compound 29c (4.50 g, brown oil, yield: 32%). $^1$H NMR (400 MHz, CDCl$_3$) δ7.60-7.58 (m, 1H), 7.38-7.36 (m, 1H), 7.24-7.21 (m, 1H), 7.13-7.10 (m, 1H), 6.44 (s, 1H), 4.92-4.88 (m, 2H), 4.67-4.62 (m, 2H), 4.49-4.47 (m, 1H), 3.77 (m, 3H), 0.94 (s, 9H), 0.15 (s, 6H).

Step III

Tetrabutylammonium fluoride (13.00 mmol, 13 mL, 1 M) was added to a solution of Compound 29c (4.50 g, 12.40 mmol) in tetrahydrofuran (20 mL), and the resulting mixture was stirred for 1 hr at 20° C. The reaction mixture was diluted with ethyl acetate (40 mL), washed with saturated brine (40 mL×3), and dried over anhydrous sodium sulfate. The drying agent was removed by filtration, and the solvent was removed from the filtrate under reduced pressure. The residue was purified by silica gel column chromatography (petroleum ether/ethyl acetate 100-30%) to give Compound 29d as yellowish solid (1.70 g, yellowish solid, yield: 55%). ¹H NMR (400 MHz, CDCl₃) δ7.63-7.61 (m, 1H), 7.38-7.36 (m, 1H), 7.28-7.24 (m, 1H), 7.17-7.13 (m, 1H), 6.53 (s, 1H), 4.81 (s, 2H), 4.69-4.62 (m, 2H), 4.48-4.46 (m, 1H), 3.84 (s, 3H).

Step IV

At 0° C., Dess-Martin periodinane (6.36 g, 15.00 mmol) was added to a solution of Compound 29d (1.70 g, 6.82 mmol) in dichloromethane (100 mL). The resulting mixture was stirred for 1 h at 0° C., warmed to 20° C., and then further stirred for 1 hr. The reaction mixture was diluted with dichloromethane (50 mL), washed successively with a saturated aqueous solution of sodium thiosulfate (50 mL×2), a saturated aqueous solution of sodium bicarbonate (50 mL×2), and saturated brine (50 mL×3), and dried over anhydrous sodium sulfate. The drying agent was removed by filtration, and the solvent was removed from the filtrate under reduced pressure. The residue was purified by silica gel column chromatography (petroleum ether/ethyl acetate 100-50%), to give Compound 29e as brown solid (750 mg, brown solid, yield: 45%). ¹H NMR (400 MHz, CDCl₃) δ9.81 (s, 1H), 7.79-7.77 (m, 1H), 7.46-7.41 (m, 1H), 7.38 (s, 1H), 7.2-7.22 (m, 2H), 5.80 (s, 2H), 3.97 (s, 3H).

Step V

Ammonium acetate (1.15 g, 14.90 mmol) was added to a solution of Compound 29e (730 mg, 2.98 mmol) in acetic acid (30 mL), warmed to 60° C., and stirred for 2 hr. The solvent was removed from the reaction mixture under reduced pressure, and the resulting mixture was diluted with ethyl acetate (100 mL), washed successively with a saturated aqueous solution of sodium bicarbonate (100 mL×3) and saturated brine (100 mL×2), and dried over anhydrous sodium sulfate. The drying agent was removed by filtration, and the solvent was removed from the filtrate under reduced pressure. The residue was purified by silica gel column chromatography (petroleum ether/ethyl acetate 100-50%), to give Compound 29f (420 mg, yellow solid, yield: 62%). ¹H NMR (400 MHz, CDCl₃) δ9.15 (s, 1H), 9.03 (s, 1H), 8.07-8.04 (m, 1H), 7.95-7.93 (m, 1H), 7.54-7.52 (m, 2H), 7.11 (s, 1H), 4.04 (s, 3H).

Step VI

Compound 29 was synthesized from Compound 29f and Compound 1k according to the synthesis method of Compound 7 (2 mg, yield: 7%). ¹H NMR (400 MHz, CD₃OD) δ9.53 (s, 1H), 9.23 (s, 1H), 8.39-8.37 (m, 1H), 7.93-7.86 (m, 3H), 7.66-7.57 (m, 4H), 4.77 (s, 2H), 3.08 (s, 3H). MS-ESI calculated value [M+H]⁺ 381, measured value 381.

29f + 19a ⟶

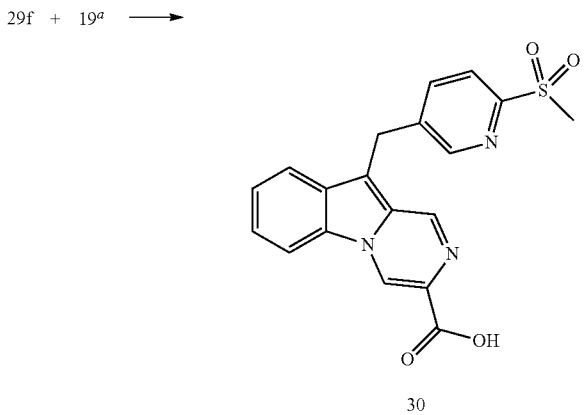

Example 30

Compound 30 was synthesized from Compound 29f and Compound 19a according to the synthesis method of Compound 7 (2 mg, yield: 8%). ¹H NMR (400 MHz, CD₃OD) δ9.56 (s, 1H), 9.32 (s, 1H), 8.78 (s, 1H), 8.41-8.39 (m, 1H), 7.98-7.97 (s, 2H), 7.94-7.92 (m, 1H), 7.68-7.64 (m, 1H), 7.61-7.57 (m, 1H), 4.82 (s, 2H), 3.20 (s, 3H). MS-ESI calculated value [M+H]⁺ 382, measured value 382.

29f + 6a ⟶

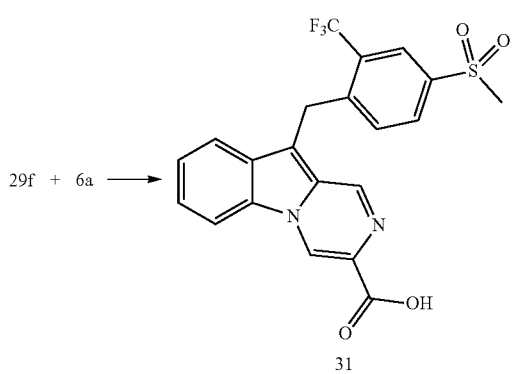 [SMILES: CS(=O)(=O)c1ccc(Cc2c3ccccc3n3cc(C(=O)O)ncc23)c(C(F)(F)F)c1]

Example 31

Compound 31 was synthesized from Compound 29f and Compound 6a according to the synthesis method of Compound 7 (8 mg, yield: 49%). ¹H NMR (400 MHz, DMSO-d₆) δ9.58 (s, 1H), 9.17 (s, 1H), 9.63-9.61 (m, 1H), 8.25 (s, 1H), 7.97-7.95 (m, 1H), 7.57-7.55 (m, 1H), 7.51-7.43 (m, 2H), 7.29-7.27 (m, 1H), 4.81 (s, 2H), 3.27 (s, 3H). MS-ESI calculated value [M+H]⁺ 449, measured value 449.

Example 32

1c + 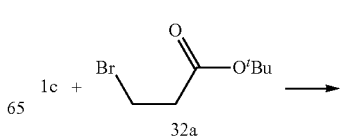 ⟶

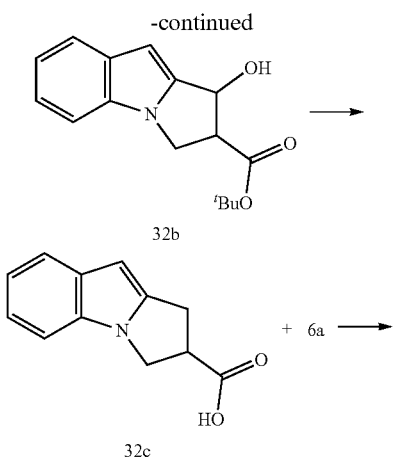

32b

32c

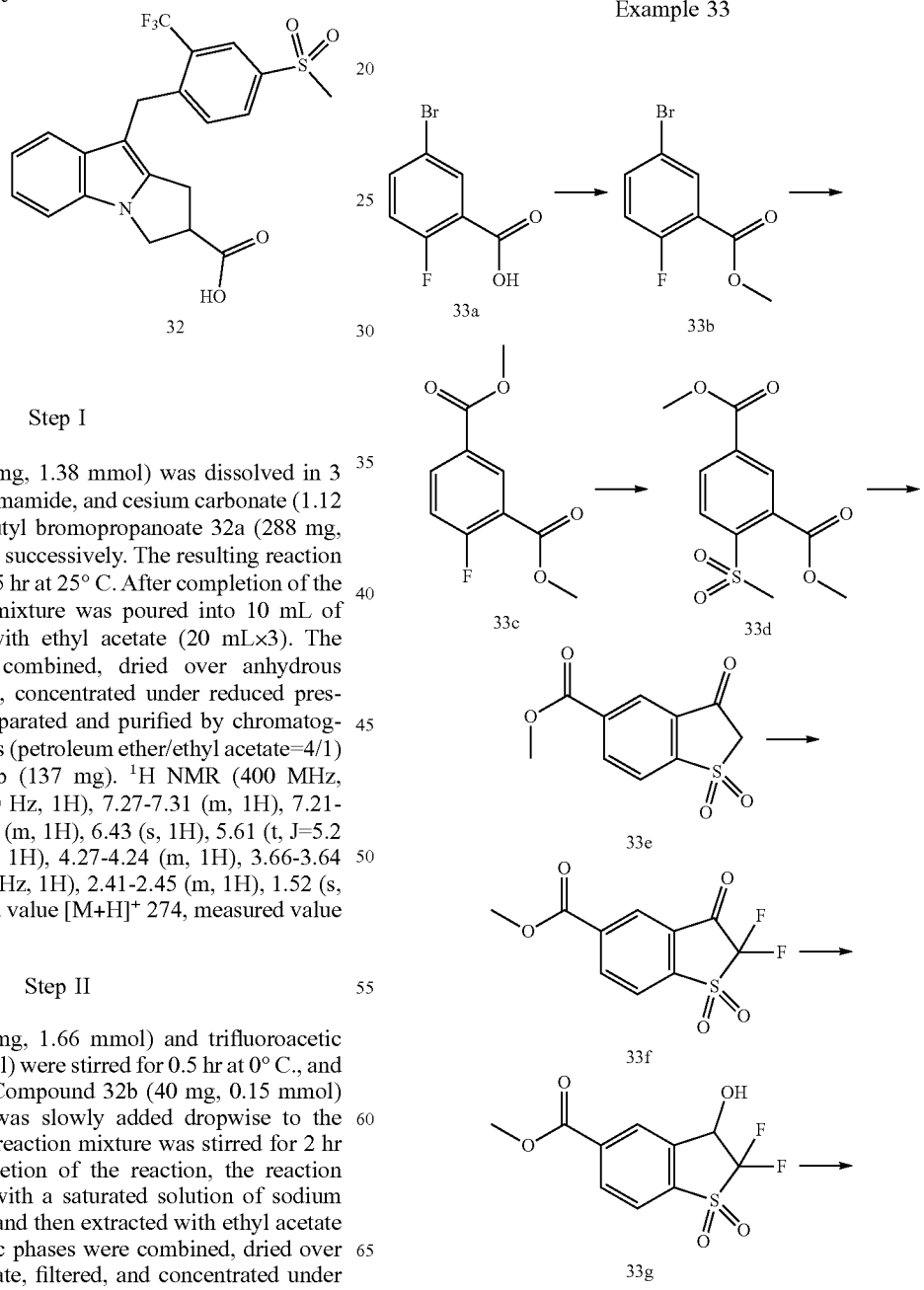

The product was directly used in the next step without purification. MS-ESI calculated value [M+H]+ 202, measured value 202.

Step III

Compound 32c reacted with Compound 6a according to the synthesis method in Example 1 to give Compound 32 (12 mg). $^1$H NMR (400 MHz, DMSO-d$_6$) δ8.20 (s, 1H), 8.06 (d, J=8.0 Hz, 1H), 7.39-7.46 (m, 1H), 7.34 (d, J=8.0 Hz, 1H) 7.27 (d, J=8.0 Hz, 1H) 7.07 (t, J=7.6 Hz, 1H), 6.93-6.99 (m, 1H), 4.52 (s, 2H), 3.92-4.01 (m, 1H), 3.83-3.91 (m, 1H), 3.29 (s, 3H), 2.90-3.07 (m, 2H), 2.33 (brs, 1H). MS-ESI calculated value [M+H]+ 438, measured value 438.

Example 33

Step I

Compound 1c (200 mg, 1.38 mmol) was dissolved in 3 mL of N,N-dimethylformamide, and cesium carbonate (1.12 g, 3.45 mmol) and t-butyl bromopropanoate 32a (288 mg, 1.38 mmol) were added successively. The resulting reaction mixture was stirred for 5 hr at 25° C. After completion of the reaction, the reaction mixture was poured into 10 mL of water, and extracted with ethyl acetate (20 mL×3). The organic phases were combined, dried over anhydrous sodium sulfate, filtered, concentrated under reduced pressure to dryness, and separated and purified by chromatography on silica gel plates (petroleum ether/ethyl acetate=4/1) to give Compound 32b (137 mg). $^1$H NMR (400 MHz, CDCl$_3$) δ7.61 (d, J=8.0 Hz, 1H), 7.27-7.31 (m, 1H), 7.21-7.19 (m, 1H), 7.08-7.13 (m, 1H), 6.43 (s, 1H), 5.61 (t, J=5.2 Hz, 1H), 4.49-4.46 (m, 1H), 4.27-4.24 (m, 1H), 3.66-3.64 (m, 1H), 2.43 (d, J=5.6 Hz, 1H), 2.41-2.45 (m, 1H), 1.52 (s, 9H). MS-ESI calculated value [M+H]+ 274, measured value 274.

Step II

Triethylsilane (193 mg, 1.66 mmol) and trifluoroacetic acid (118 mg, 1.04 mmol) were stirred for 0.5 hr at 0° C., and 5 mL of a solution of Compound 32b (40 mg, 0.15 mmol) in 1,2-dichloroethane was slowly added dropwise to the solution. The resulting reaction mixture was stirred for 2 hr at 25° C. After completion of the reaction, the reaction mixture was adjusted with a saturated solution of sodium bicarbonate to pH 4-5, and then extracted with ethyl acetate (10 mL×2). The organic phases were combined, dried over anhydrous sodium sulfate, filtered, and concentrated under reduced pressure to dryness, to give Compound 32c (29 mg).

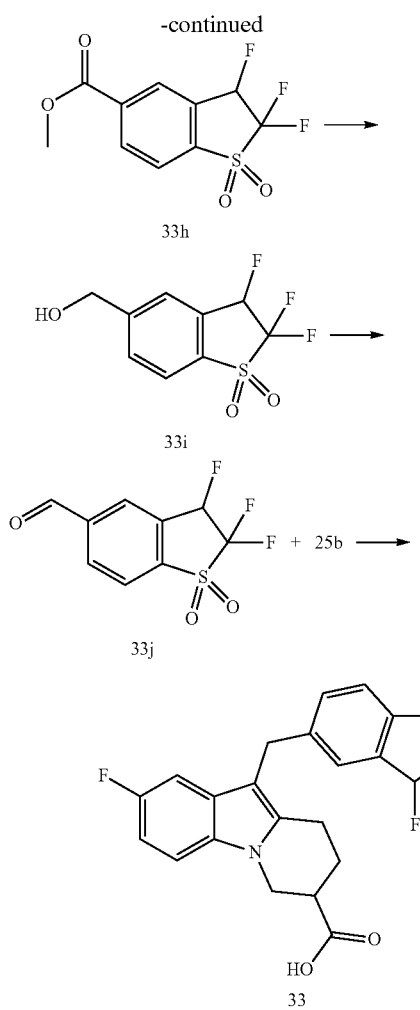

added successively. The reaction mixture was stirred under a carbon monoxide atmosphere (50 psi) for 16 hr at 80° C., filtered, concentrated under reduced pressure to dryness, diluted with 100 mL of water, and extracted with ethyl acetate (500 mL×2). The organic phases were combined, dried over anhydrous sodium sulfate, filtered, concentrated under reduced pressure to dryness, and purified by silica gel column chromatography (petroleum ether/ethyl acetate=100-0%) to give Compound 33c (11.00 g). $^1$H NMR (400 MHz, CDCl$_3$) δ3.95 (s, 3H), 3.97 (s, 3H), 7.20-7.24 (m, 1H), 8.21-8.23 (m, 1H), 8.63-8.65 (m, 1H). MS-ESI calculated value [M+H]$^+$ 213, measured value 213.

Step III

Compound 33c (11.00 g, 51.85 mmol) was dissolved in dimethyl sulfoxide (50 mL), and sodium methylsulfinate (5.82 g, 57.04 mmol) was added. The reaction mixture was stirred for 16 hr at 90° C., poured into ice water (300 mL), and then extracted with ethyl acetate (400 mL×2). The organic phases were combined, dried over anhydrous sodium sulfate, filtered, concentrated under reduced pressure to dryness, and separated and purified by silica gel column chromatography (petroleum ether/ethyl acetate=100-0%) to give Compound 33d (11.00 g). $^1$H NMR (400 MHz, CDCl$_3$) δ3.93 (s, 3H), 3.93 (s, 3H), 3.97 (s, 3H), 8.21-8.29 (m, 1H), 8.30-8.36 (m, 1H), 8.37 (s, 1H). MS-ESI calculated value [M+H]$^+$ 273, measured value 273.

Step IV

Compound 33d (10.00 g, 36.73 mmol) was dissolved in tetrahydrofuran (300 mL), and lithium bis(trimethylsilyl) amide (7.99 g, 47.75 mmol) was slowly added dropwise at −78° C. The reaction mixture was stirred for 3 hr at −78° C., and then a saturated solution of ammonium chloride was added to quench the reaction and adjust the pH to 7. Most tetrahydrofuran was removed by concentration under reduced pressure, and the resulting mixture was extracted with ethyl acetate (500 mL×2). The organic phases were combined, dried over anhydrous sodium sulfate, filtered, and concentrated under reduced pressure to dryness to give Compound 33e (8.00 g). $^1$H NMR (400 MHz, CDCl$_3$) δ4.02 (s, 3H), 4.17 (s, 2H), 3.97 (s, 3H), 8.09 (d, J=8.0 Hz, 1H), 8.59-8.61 (m, 1H), 8.66 (s, 1H). MS-ESI calculated value [M+H]$^+$ 241, measured value 241.

Step V

Compound 33e (4.00 g, 16.65 mmol) was dissolved in acetonitrile (50 mL), and anhydrous sodium carbonate (5.29 g, 49.95 mmol) was added. After completion of the addition, the resulting mixture was stirred for 0.5 hr at 20° C., and 1-chloromethyl-4-fluoro-1,4-diazoniabicyclo[2,2,2]octane ditetrafluoroborate (12.98 g, 36.63 mmol) was added. The reaction mixture was stirred for 0.5 hr at 20° C. A saturated solution of ammonium chloride was added to quench the reaction and adjust the pH to 7. The reaction mixture was extracted with ethyl acetate (50 mL×2). The organic phases were combined, dried over anhydrous sodium sulfate, filtered, concentrated under reduced pressure to dryness, and separated and purified by silica gel column chromatography (petroleum ether/ethyl acetate=100-0%) to give Compound 33f (3.40 g). $^1$H NMR (400 MHz, CDCl$_3$) δ4.05 (s, 3H), 8.18 (d, J=8.0 Hz, 1H), 8.73 (d, J=8.4 Hz, 1H), 8.77 (s, 1H). MS-ESI calculated value [M+H]$^+$ 277, measured value 277.

Step I

Compound 33a (25.00 g, 114.15 mmol) was dissolved in methanol (250 mL), and concentrated sulfuric acid (5.60 g, 57.08 mmol) was slowly added dropwise. After completion of the addition, the resulting mixture was stirred under reflux for 5 hr at 70° C. After completion of the reaction, a saturated solution of sodium bicarbonate was added to the reaction system to adjust the pH to 7. A large amount of methanol was removed by concentration under reduced pressure, and then the resulting mixture was extracted with ethyl acetate (250 mL×2). The organic phases were combined, dried over anhydrous sodium sulfate, filtered, concentrated under reduced pressure to dryness, and purified by silica gel column chromatography (petroleum ether/ethyl acetate=100-0%) to give Compound 33b (25.00 g). $^1$H NMR (400 MHz, CDCl$_3$) δ3.93 (s, 3H) 7.04 (t, J=8.8 Hz, 1H) 7.59-7.62 (m, 1H), 8.04-8.07 (m, 1H). MS-ESI calculated value [M+H]$^+$ 234, measured value 234.

Step II

Compound 33b (24.00 g, 102.99 mmol) was dissolved in methanol (300 mL), and N,N-dimethylformamide (100 mL), triethylamine (100 mL), and [1,1-bis(diphenylphosphino)ferrocene]dichloropalladium (12.62 g, 15.45 mmol) were

Step VI

Compound 33f (1.50 g, 5.43 mmol) was dissolved in tetrahydrofuran (30 mL), and sodium borohydride (230 mg, 6.08 mmol) was slowly added at 0° C. The reaction mixture was stirred for 2 hr at 0° C., and then 1N hydrochloric acid was added to quench the reaction and adjust the pH to 7. Most tetrahydrofuran was removed by concentration under reduced pressure, and the resulting mixture was extracted with ethyl acetate (50 mL×2). The organic phases were combined, dried over anhydrous sodium sulfate, filtered, concentrated under reduced pressure to dryness, and separated and purified by silica gel column chromatography (petroleum ether/ethyl acetate=100-0%) to give Compound 33g (1.20 g). $^1$H NMR (400 MHz, CDCl$_3$) δ3.93 (s, 3H), 5.72 (m, 1H), 8.24-8.25 (m, 3H). MS-ESI calculated value [M+H]$^+$ 279, measured value 279.

Step VII

Compound 33g (1.20 g, 4.31 mmol) was dissolved in dichloromethane (20 mL), and diethylaminosulfur trifluoride (1.39 g, 8.62 mmol) was slowly added dropwise at 0° C. After the reaction mixture was stirred for 16 hr at 20° C., a saturated solution of sodium bicarbonate was added to quench the reaction and adjust the pH to 7. The resulting mixture was extracted with dichloromethane (10 mL×2). The organic phases were combined, dried over anhydrous sodium sulfate, filtered, concentrated under reduced pressure to dryness, and separated and purified by silica gel column chromatography (petroleum ether/ethyl acetate=100-0%) to give Compound 33h (180 mg). $^1$H NMR (400 MHz, CDCl$_3$) δ4.02 (s, 3H), 5.95-6.13 (m, 1H), 8.01-7.99 (m, 1H), 8.40-8.46 (m, 2H). MS-ESI calculated value [M+H]$^+$ 277, measured value 277.

Step VIII

Compound 33h (480 mg, 1.71 mmol) was dissolved in tetrahydrofuran (10 mL), and diisobutyl aluminum hydride (603.67 mg, 4.28 mmol) was slowly added dropwise at 0° C. Then, the reaction mixture was stirred for 5 hr at 20° C. 1N hydrochloric acid was added to quench the reaction and adjust the pH to 7. The resulting mixture was extracted with ethyl acetate (60 mL×2). The organic phases were combined, dried over anhydrous sodium sulfate, filtered, concentrated under reduced pressure to dryness, and separated and purified by chromatography on silica gel plates (petroleum ether/ethyl acetate=2/1) to give Compound 33i (180 mg). $^1$H NMR (400 MHz, CDCl$_3$) δ7.88 (d, J=8.0 Hz, 1H), 7.80 (s, 1H), 7.75 (d, J=8.0 Hz, 1H), 5.89-6.08 (m, 1H), 4.90 (s, 2H). MS-ESI calculated value [M+H]$^+$ 253, measured value 253.

Step IX

Compound 33i (180 mg, 0.71 mmol) was dissolved in dichloromethane (10 mL), and manganese dioxide (496 mg, 5.71 mmol) was added. The reaction mixture was stirred for 2 hr at 20° C., filtered, and concentrated under reduced pressure to dryness, to give Compound 33j (160 mg). $^1$H NMR (400 MHz, CDCl$_3$) δ10.17 (s, 1H), 8.24-8.33 (m, 2H), 8.11 (d, J=8.0 Hz, 1H), 5.99-6.18 (m, 1H). MS-ESI calculated value [M+H]$^+$ 251, measured value 251.

Step X

Compound 33j reacted with Compound 25b according to the synthesis method in Example 7 to give Compound 33 (5 mg). $^1$H NMR (400 MHz, CD$_3$OD) δ7.85 (d, J=8.0 Hz, 1H), 7.63-7.75 (m, 2H), 7.31 (dd, J=8.8 Hz, J=4.4 Hz, 1H), 7.02 (d, J=10.0 Hz, 1H), 6.82-6.93 (m, 1H), 6.11-6.36 (m, 1H), 4.37 (dd, J=12.0 Hz, J=4.8 Hz, 1H), 4.20 (s, 2H), 4.09-4.16 (m, 1H), 2.98-3.18 (m, 2H), 2.81-2.93 (m, 1H), 2.31 (s, 1H), 1.98-2.08 (m, 1H). MS-ESI calculated value [M+H]$^+$ 469, measured value 469.

Example 34

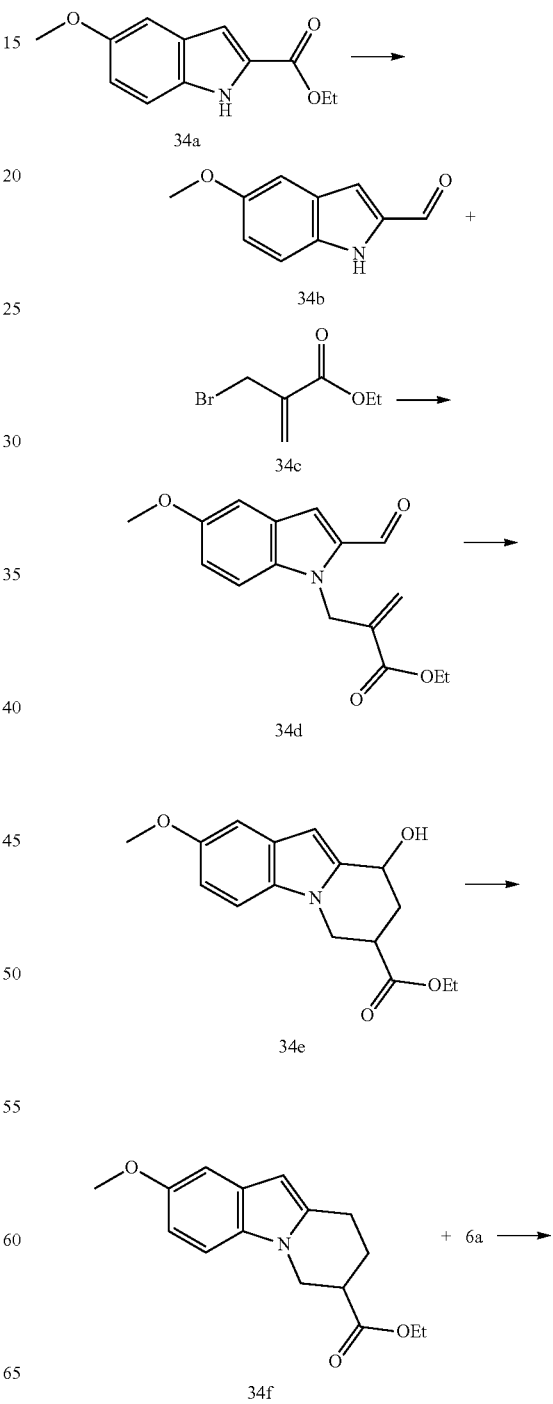

-continued

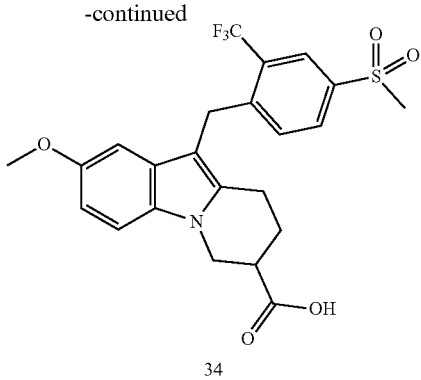

34

Step I

Compound 34b (2.00 g) was obtained from Compound 34a according to the synthesis method in Example 1. $^1$H NMR (400 MHz, CDCl$_3$) δ9.82 (s, 1H), 9.14 (s, 1H), 7.37 (d, J=9.2 Hz, 1H), 7.21 (d, J=1.2 Hz, 1H), 7.06-7.13 (m, 2H), 3.87 (s, 3H). MS-ESI calculated value [M+H]$^+$ 176, measured value 176.

Step II

Compound 34b reacted with Compound 34c according to the synthesis method in Example 1 to give Compound 34d (3.20 g). $^1$H NMR (400 MHz, CDCl$_3$) δ9.85 (s, 1H), 7.26-7.29 (m, 1H), 7.25 (s, 1H), 7.07-7.16 (m, 2H), 6.17 (s, 1H), 5.40-5.49 (m, 2H), 4.84 (s, 1H), 4.29 (q, J=7.2 Hz, 2H), 3.88 (s, 3H), 1.35 (t, J=7.2 Hz, 3H). MS-ESI calculated value [M+H]$^+$ 288, measured value 288.

Step III

Under the protection of nitrogen, a tetrahydrofuran solution of samarium diiodide (174 mL, 174 mmol, 1 M) and hexamethylphosphoric triamide (20 mL) were successively added to a three-necked flask. A solution of Compound 34d (2.00 g, 6.96 mmol) in t-butanol (1 mL) and tetrahydrofuran (60 mL) was slowly added dropwise to the above solution in 2 hr at −10-0° C. After completion of the dropwise addition, the resulting reaction mixture was stirred for 14 hr at 20° C. After completion of the reaction, a saturated solution of sodium bicarbonate (200 mL) was added to quench the reaction. The resulting mixture was extracted with ethyl acetate (100 mL×3). The organic phases were combined, dried over anhydrous sodium sulfate, filtered, and concentrated under reduced pressure. The resulting crude product was separated and purified by silica gel column chromatography (petroleum ether/ethyl acetate=100-0%), to give Compound 34e (290 mg). $^1$H NMR (400 MHz, CDCl$_3$) δ7.25 (d, J=9.2 Hz, 1H), 7.07 (d, J=2.4 Hz, 1H), 6.92-6.90 (m, 1H), 6.44 (s, 1H), 5.19 (t, J=3.2 Hz, 1H), 4.49-4.46 (m, 1H), 4.22-4.29 (m, 2H), 3.93 (t, J=11.6 Hz, 1H), 3.57-3.54 (m, 1H), 2.54-2.51 (m, 1H), 2.06-2.13 (m, 1H), 2.03-2.06 (m, 1H), 1.31-1.36 (m, 3H). MS-ESI calculated value [M+H]$^+$ 290, measured value 290.

Step IV

Compound 34f (50 mg) was obtained from Compound 34e according to the synthesis method in Example 32. The product was directly used in the next step without purification. MS-ESI calculated value [M+H]$^+$ 274, measured value 274.

Step V

Compound 34f reacted with Compound 6a according to the synthesis method in Example 6 to give Compound 34 (13 mg). $^1$H NMR (400 MHz, CD$_3$OD) δ8.24 (s, 1H), 7.94 (d, J=8.0 Hz, 1H), 7.31-7.27 (m, 2H), 6.77 (d, J=8.8 Hz, 1H), 6.68 (s, 1H), 4.39-4.36 (m, 1H), 4.29 (s, 2H) 4.06-4.16 (m, 1H), 3.70 (s, 3H), 3.14 (brs, 4H), 2.98-2.93 (m, 1H), 2.84-2.80 (m, 1H), 2.31 (brs, 1H), 2.03 (brs, 1H). MS-ESI calculated value [M+H]$^+$ 482, measured value 482.

Example 35

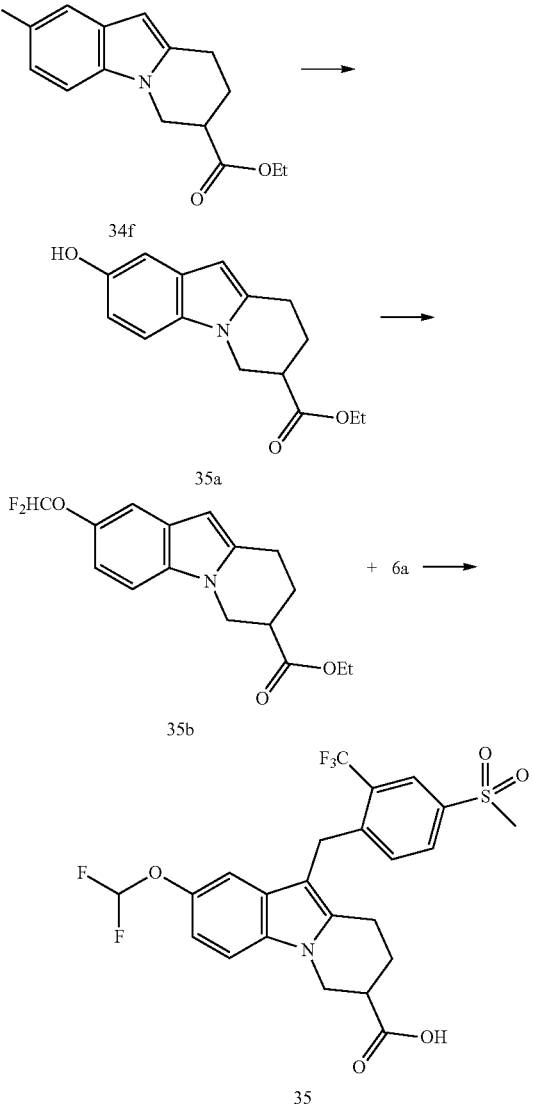

35

Step I

Compound 34f (290 mg, 1.06 mmol) was dissolved in 3 mL of dichloromethane, and boron tribromide (797 mg, 3.18 mmol) was slowly added dropwise at 0° C. The resulting reaction mixture was stirred for 16 hr at 20° C. After completion of the reaction, methanol (20 mL) was added to quench the reaction. The pH was adjusted with a saturated solution of sodium bicarbonate to 6-7. Most methanol was removed by concentration under reduced pressure, and then the resulting mixture was extracted with ethyl acetate (10 mL×3). The organic phases were combined, dried over anhydrous sodium sulfate, filtered, concentrated under reduced pressure to dryness, and separated and purified by chromatography on silica gel plates (petroleum ether/ethyl acetate=2/1) to give Compound 35a (24 mg). $^1$H NMR (400 MHz, CDCl$_3$) δ7.15 (d, J=8.4 Hz, 1H), 6.95 (d, J=2.4 Hz, 1H), 6.73-6.71 (m, 1H), 6.10 (s, 1H), 4.52 (s, 1H), 4.37-3.34 (m, 1H), 4.21-4.29 (m, 2H), 4.05-4.02 (m, 1H), 2.90-3.17 (m, 3H), 2.30-2.39 (m, 1H), 1.98-1.94 (m, 1H), 1.33-1.31 (m, 3H). MS-ESI calculated value [M+H]$^+$ 260, measured value 260.

Step II

Compound 35a (40 mg, 0.15 mmol) was dissolved in N,N-dimethylformamide (2 mL), and sodium hydride (12 mg, 0.31 mmol) was slowly added at 0° C. The resulting reaction mixture was stirred for 0.5 hr at 0° C., and the gas of monochlorodifluoromethane was continuously introduced. The reaction mixture was further reacted under the gas for 1.5 hr at 20° C. After completion of the reaction, the reaction mixture was slowly poured into ice water (10 mL), and the resulting mixture was extracted with ethyl acetate (10 mL×3). The organic phases were combined, dried over anhydrous sodium sulfate, filtered, concentrated under reduced pressure to dryness, and separated and purified by chromatography on silica gel plates (petroleum ether/ethyl acetate=2/1) to give Compound 35b (10 mg). $^1$H NMR (400 MHz, CDCl$_3$) δ7.29 (d, J=2.0 Hz, 1H), 7.24 (s, 1H), 6.97-6.95 (m, 1H), 6.28-6.68 (m, 1H), 6.21 (s, 1H), 4.40-4.37 (m, 1H), 4.21-4.29 (m, 2H), 4.10-4.07 (m, 1H), 2.88-3.19 (m, 3H), 2.30-2.42 (m, 1H), 1.93-2.08 (m, 1H), 1.29-1.35 (m, 3H). MS-ESI calculated value [M+H]$^+$ 310, measured value 310.

Step III

Compound 35b reacted with Compound 6a according to the synthesis method in Example 6 to give Compound 35 (9 mg). $^1$H NMR (400 MHz, DMSO-d$_6$) δ8.19 (s, 1H), 8.03-8.01 (m, 1H), 7.21 (brs, 1H), 7.02-7.00 (m, 1H), 6.93-6.83 (m, 3H), 4.32-4.09 (m, 4H), 3.27 (s, 3H), 2.67 (s, 2H), 2.33 (s, 2H), 2.02 (s, 1H). MS-ESI calculated value [M+H]$^+$518, measured value 518.

Example 36

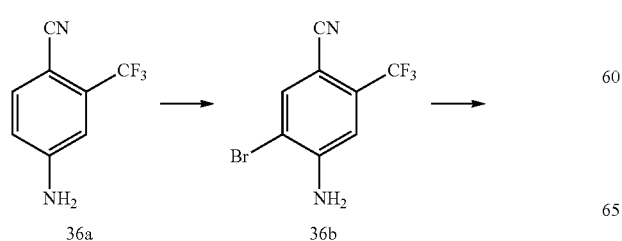

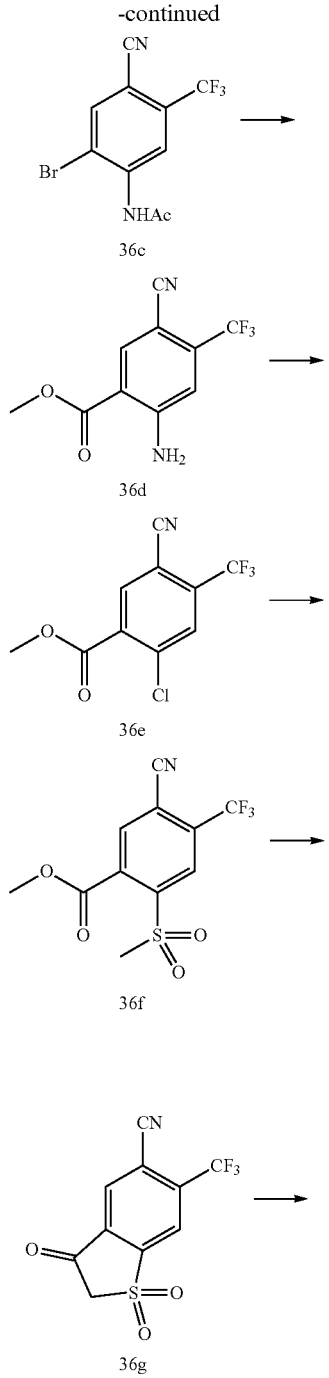

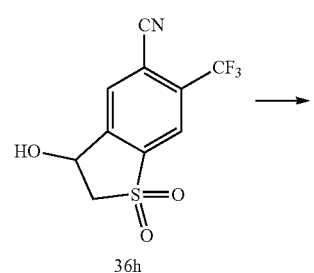

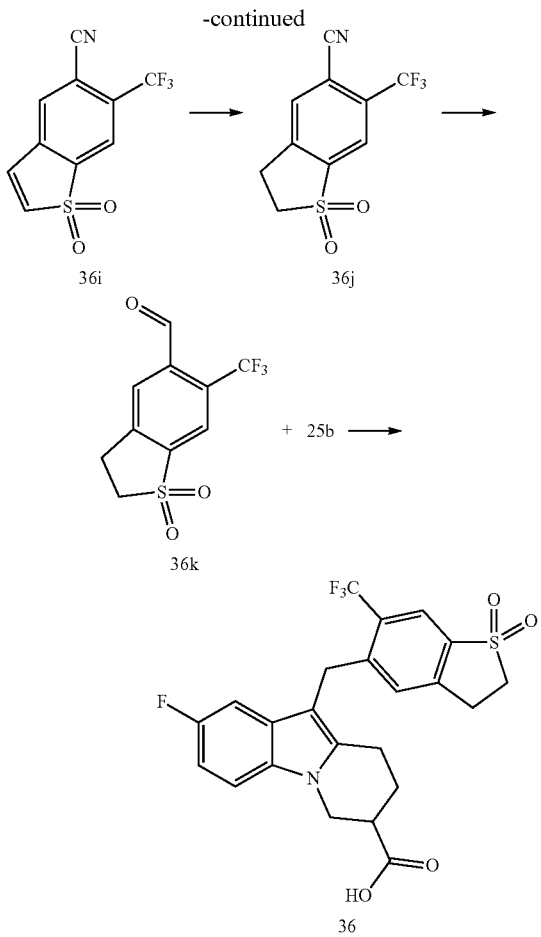

Step I

At 0° C., liquid bromine (21.68 g, 135.66 mmol) was slowly added dropwise to a solution of Compound 36a (25.00 g, 134.31 mmol) in methanol (200 mL). After the resulting reaction mixture was further stirred for 0.5 hr, a saturated solution of sodium thiosulfate (200 mL) was added to the reaction system at 0° C. to quench the reaction. The resulting mixture was diluted with water (1000 mL), and filtered. The filter cake was washed with water (200 mL×3), and dried under reduced pressure to give Compound 36b (34.30 g). $^1$H NMR (400 MHz, DMSO-d$_6$) δ8.14 (s, 1H), 7.20 (s, 1H), 6.90 (brs, 2H).

Step II

At 0° C., diisopropylethylamine (2.54 g, 19.62 mmol) and trifluoroacetic anhydride (3.49 g, 16.60 mmol) were added to a solution of Compound 36b (4.00 g, 15.09 mmol) in dichloromethane (50 mL). After the resulting reaction mixture was stirred for 10 hr at 25° C., a saturated solution of sodium chloride (100 mL) was added to the reaction system at 0° C. to quench the reaction. The resulting mixture was diluted with 100 mL of a saturated solution of sodium chloride, and extracted with ethyl acetate (100 mL×3). The organic phases were combined, washed with a saturated solution of sodium chloride (100 mL×3), dried over anhydrous sodium sulfate, filtered, and concentrated under reduced pressure to give a residue. The residue was separated and purified by silica gel column chromatography (petroleum ether/ethyl acetate=100-0%), to give Compound 36c (5.20 g). $^1$H NMR (400 MHz, DMSO-d$_6$) δ11.78 (brs, 1H), 8.72 (s, 1H), 8.56 (s, 1H).

Step III

Compound 36d (2.87 g) was obtained from Compound 36c according to the synthesis method of Compound 33c in Example 33.

Step IV

At 0° C., 20 mL of a solution of sodium nitrite (1.21 g, 17.51 mmol) in water was slowly added dropwise to a solution of Compound 36d (2.85 g, 11.67 mmol) in concentrated hydrochloric acid (42.89 mL, 12 N) and 50 mL of acetic acid, and the resulting mixture was stirred for 1 hr. A suspension of cuprous chloride (3.47 g, 35.01 mmol) in concentrated hydrochloric acid (42.89 mL, 12 N) was added to the reaction system. After the resulting reaction mixture was further stirred for 1 hr, the reaction system was dispersed in 200 mL of a saturated solution of sodium chloride and 250 mL of ethyl acetate. The organic phase was separated, washed successively with a saturated solution of sodium chloride (100 mL×3) and a saturated solution of sodium bicarbonate (100 mL×3), dried over anhydrous sodium sulfate, filtered, and concentrated under reduced pressure to give a residue. The residue was separated and purified by silica gel column chromatography (petroleum ether/ethyl acetate=100-0%), to give Compound 36e (2.60 g). $^1$H NMR (400 MHz, DMSO-d$_6$) δ8.59 (s, 1H), 8.32 (s, 1H), 3.93 (s, 3H).

Step V

Sodium methanesulfinate (3.02 g, 29.58 mmol) was added to a solution of Compound 36e (2.60 g, 9.86 mmol) in N,N-dimethylformamide (30 mL). After the resulting reaction mixture was stirred for 1 hr at 50° C., water (100 mL) was added to the reaction system to quench the reaction, and the resulting mixture was filtered. The resulting solid was washed with water, dissolved in ethyl acetate (100 mL), dried over anhydrous sodium sulfate, filtered, and concentrated under reduced pressure to give a residue. The residue was separated and purified by silica gel column chromatography (petroleum ether/ethyl acetate=100-0%), to give Compound 36f (2.50 g). $^1$H NMR (400 MHz, DMSO-d$_6$) δ8.68 (s, 1H), 8.42 (s, 1H), 3.93 (s, 3H), 3.50 (s, 3H).

Step VI

Compound 36g (1.45 g) was obtained from Compound 36f according to the synthesis method of Compound 33e in Example 33. $^1$H NMR (400 MHz, DMSO-d$_6$) δ8.99 (s, 1H), 8.87 (s, 1H), 4.76 (s, 2H).

Step VII

At 0° C., sodium borohydride (219 mg, 5.80 mmol) was added in batch to a solution of Compound 36g (1.45 g, 5.27 mmol) in methanol (30 mL). After the resulting reaction mixture was further stirred for 0.5 hr, a saturated solution of ammonium chloride (100 mL) was added to the reaction system at 0° C., and then the resulting mixture was extracted with ethyl acetate (100 mL×3). The organic phases were combined, washed with a saturated solution of sodium chloride (100 mL×3), dried over anhydrous sodium sulfate, filtered, and concentrated under reduced pressure to give a residue. The residue was separated and purified by silica gel column chromatography (petroleum ether/ethyl acetate=100-0%) to give Compound 36h (1.20 g). ¹H NMR (400 MHz, DMSO-d₆) δ8.57 (s, 1H), 8.50 (s, 1H), 6.68-6.66 (d, J=6.0 Hz, 1H), 5.54-5.50 (m, 1H), 4.20-4.15 (m, 1H), 4.20-4.15 (m, 1H).

Step VIII

At 0° C., methanesulfonyl chloride (595 mg, 5.20 mmol) and triethylamine (876 mg, 8.66 mmol) were added to a solution of Compound 36h (1.20 g, 4.33 mmol) in dichloromethane (20 mL). After the resulting reaction mixture was stirred for 1 hr at 25° C., a saturated solution of sodium chloride (100 mL) was added to the reaction system to quench the reaction, and the resulting mixture was diluted with ethyl acetate (200 mL). The organic phase was separated, washed with a saturated solution of sodium chloride (50 mL×3), dried over anhydrous sodium sulfate, filtered, and concentrated under reduced pressure to give a residue. The residue was separated and purified by silica gel column chromatography (petroleum ether/ethyl acetate=100-0%), to give Compound 36i (1.10 g).

Step IX

Compound 36j (900 mg) was obtained from Compound 36i according to the synthesis method of Compound 24d in Example 24. ¹H NMR (400 MHz, DMSO-d₆) δ8.50 (s, 1H), 8.47 (s, 1H), 3.79-3.76 (m, 2H), 3.52-3.49 (m, 2H).

Step X

Under the protection of nitrogen and at −78° C., DIBAL-H (1.15 mL, 1.15 mmol, 1 M) was slowly added dropwise to a solution of Compound 36j (200 mg, 0.77 mmol) in 5 mL of dichloromethane. After the resulting reaction mixture was stirred for 1 hr at −78° C., a saturated solution of ammonium chloride (50 mL) was added to the reaction system to quench the reaction, and then the resulting mixture was extracted with ethyl acetate (50 mL×3). The organic phases were combined, washed with a saturated solution of sodium chloride (50 mL×3), dried over anhydrous sodium sulfate, filtered, and concentrated under reduced pressure to give a residue. The residue was separated and purified by silica gel column chromatography (petroleum ether/ethyl acetate=100-0%), to give Compound 36k (150 mg). ¹H NMR (400 MHz, DMSO-d₆) δ10.31-10.30 (d, J=2.0 Hz, 1H), 8.33 (s, 1H), 8.25 (s, 1H), 3.77-3.74 (m, 2H), 3.55-3.52 (m, 2H).

Step X

Compound 36k reacted with Compound 25b according to the synthesis method in Example 7 to give Compound 36 (38 mg). ¹H NMR (400 MHz, DMSO-d₆) δ8.09 (s, 1H), 7.46-7.42 (m, 1H), 7.14 (s, 1H), 6.96-6.89 (m, 2H), 4.38-4.35 (m, 1H), 4.20 (s, 2H), 4.08-4.03 (m, 1H), 3.60-3.57 (m, 2H), 3.26-3.25 (m, 2H), 3.07-3.06 (m, 1H), 2.91-2.77 (m, 2H), 2.21-2.20 (m, 1H), 1.91-1.90 (m, 1H). MS-ESI calculated value [M+H]⁺ 482, measured value 482.

Example 37

36k + 22b ⟶

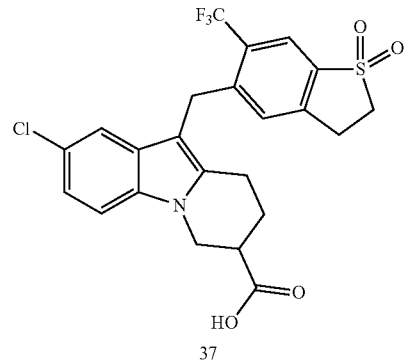

37

Step I

Compound 36k reacted with Compound 22b according to the synthesis method in Example 7 to give Compound 37 (10 mg). ¹H NMR (400 MHz, CD₃OD) δ8.05 (s, 1H), 7.36-7.34 (m, 1H), 7.16-7.08 (m, 3H), 4.41-4.37 (m, 1H), 4.28 (s, 2H), 4.18-4.16 (m, 1H), 3.54-3.51 (m, 2H), 3.27-3.23 (m, 2H), 3.01-2.97 (m, 1H), 2.84-2.81 (m, 2H), 2.32-2.31 (m, 1H), 2.01-2.00 (m, 1H). MS-ESI calculated value [M+H]⁺ 498, measured value 498.

Example 38

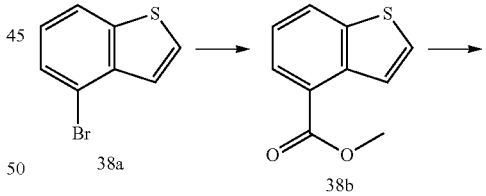

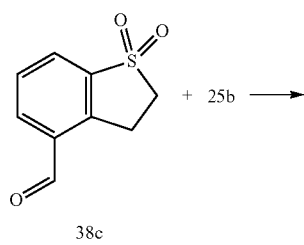

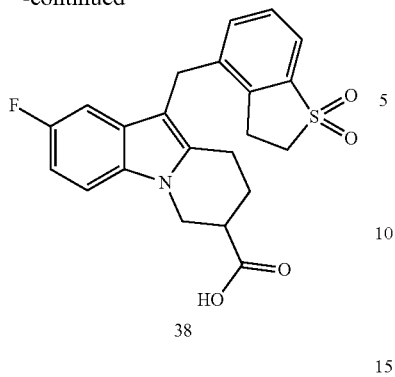

38

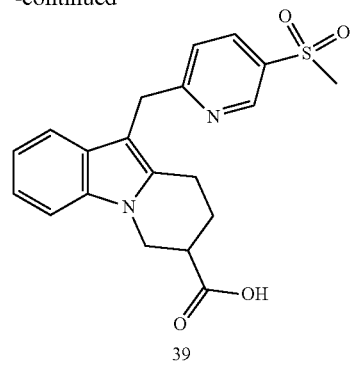

39

Step I

Compound 38b (5.80 g) was obtained from Compound 38a according to the synthesis method of Compound 33c in Example 33. $^1$H NMR (400 MHz, CDCl$_3$) δ8.25-5.24 (d, J=6.4 Hz, 1H), 8.15-8.08 (m, 2H), 7.64-7.63 (d, J=6.4 Hz, 1H), 7.43-7.39 (t, J=8.0, 1H), 4.00 (s, 3H).

Step II

Compound 38c (320 mg) was obtained from Compound 38b according to the synthesis method in Example 24. $^1$H NMR (400 MHz, CDCl$_3$) δ10.20 (s, 1H), 8.09-8.07 (m, 1H), 8.01 (d, J=8.0 Hz, 1H), 7.75 (t, J=8.0 Hz, 1H), 3.84 (t, J=6.8 Hz, 2H), 3.55 (t, J=6.8 Hz, 2H).

Step III

Compound 38c reacted with Compound 25b according to the synthesis method in Example 7 to give Compound 38 (3 mg). $^1$H NMR (400 MHz, DMSO-d$_6$) δ7.55-7.53 (m, 1H), 7.40-7.38 (m, 1H), 7.34-7.33 (m, 1H), 7.29-7.27 (m, 1H), 7.06-7.03 (m, 1H), 6.86 (s, 1H), 4.28-4.27 (m, 1H), 4.05-3.96 (m, 3H), 3.59 (s, 2H), 3.33-3.32 (m, 2H), 2.94-2.69 (m, 3H), 2.15 (s, 1H), 1.85-1.76 (m, 1H). MS-ESI calculated value [M+H]$^+$ 414, measured value 414.

Example 39

1a ⟶

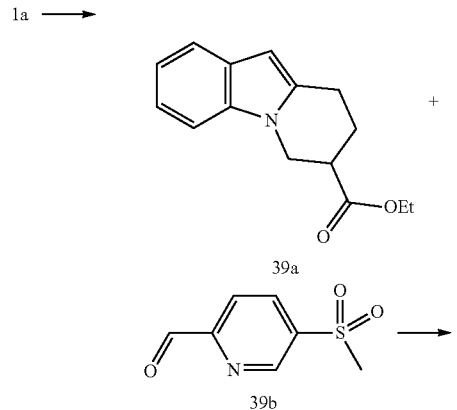

Step I

Compound 39a (275 mg) was obtained from Compound 1a according to the synthesis method in Example 34. MS-ESI calculated value [M+H]$^+$ 244, measured value 244.

Step II

Compound 39a reacted with Compound 39b according to the synthesis method in Example 7 to give Compound 39 (34 mg). $^1$H NMR (400 MHz, CD$_3$OD) δ8.96-8.95 (m, 1H), 8.14-8.12 (m, 1H), 7.36 (d, J=8.4 Hz, 2H), 7.32 (d, J=8.4 Hz, 1H), 7.10 (m, 1H), 7.02-6.97 (m, 1H), 4.42-4.35 (m, 1H), 4.33-4.31 (m, 2H), 4.10 (m, 1H), 3.15 (s, 3H), 3.14-3.08 (m, 2H), 2.97-2.87 (m, 1H), 2.36 (m, 1H), 2.09-1.99 (m, 1H). MS-ESI calculated value [M+H]$^+$ 385, measured value 385.

Example 40

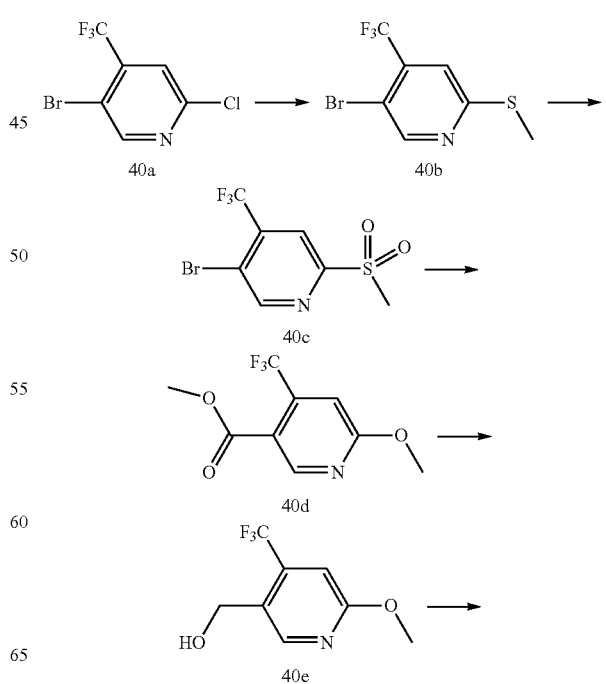

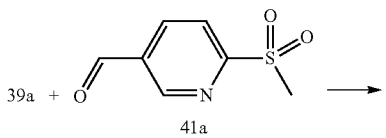

40f

40

Step I

A solution of Compound 40a (3.10 g, 11.90 mmol) and sodium thiomethoxide (918 mg, 13.09 mmol) in dioxane (30 mL) was stirred for 16 hr at 110° C. After completion of the reaction, the reaction mixture was poured into water (150 mL), and the resulting mixture was extracted with ethyl acetate (100 mL×2). The organic phases were combined, washed with saturated brine (100 mL), dried over anhydrous sodium sulfate, filtered, and concentrated to give Compound 40b (2.91 g). $^1$H NMR (400 MHz, CDCl$_3$) δ8.66 (s, 1H), 7.43 (s, 1H), 2.57 (s, 3H).

Step II m-Chloroperoxybenzoic acid (8.68 g, 42.76 mmol, purity: 85%) was added to a solution of Compound 40b (2.91 g, 10.69 mmol) in dichloromethane (100 mL). The reaction mixture was stirred for 5 hr at 25° C. After completion of the reaction, water (50 mL) was added to the reaction mixture to quench the reaction. The resulting mixture was adjusted with a saturated solution of sodium bicarbonate to pH 8, and extracted with dichloromethane (50 mL×2). The organic phases were combined, washed with saturated brine (50 mL×1), dried over anhydrous sodium sulfate, filtered, and concentrated to give Compound 40c (4.14 g, crude product). $^1$H NMR (400 MHz, CDCl$_3$) δ9.01 (s, 1H), 8.33 (s, 1H), 3.27 (s, 3H).

Step III

Compound 40d (1.38 g) was obtained from Compound 40c according to the synthesis method of Compound 33c in Example 33. $^1$H NMR (400 MHz, CDCl$_3$) δ8.79 (s, 1H), 7.08 (s, 1H), 4.03 (s, 3H), 3.93 (s, 3H).

Step IV

At 0° C., lithium aluminium hydride (500 mg, 13.18 mmol) was added to a solution of Compound 40d (1.28 g, 4.52 mmol) in tetrahydrofuran (50 mL). The resulting reaction mixture was warmed to 25° C., and stirred for 1 hr. After completion of the reaction, water (0.5 mL), 15% sodium hydroxide solution (0.5 mL), and water (1.5 mL) were added successively to the reaction mixture to quench the reaction, the resulting mixture was filtered, and the filter cake was washed with ethyl acetate (25 mL×3). The filtrates were combined, and concentrated to give Compound 40e (910 mg). $^1$H NMR (400 MHz, CDCl$_3$) δ8.41 (s, 1H), 6.99 (s, 1H), 4.79 (s, 2H), 3.98 (s, 3H).

Step V

Compound 40f was obtained from Compound 40e according to the synthesis method in Example 24 (161 mg, yield: 18%). $^1$H NMR (400 MHz, CDCl$_3$) δ10.23 (s, 1H), 8.91 (s, 1H), 7.06 (s, 1H), 4.08 (s, 3H).

Step VI

Compound 40 (50 mg) was synthesized from Compound 39a and Compound 40f according to the synthesis method of Compound 7. $^1$H NMR (400 MHz, CD$_3$OD) δ7.71 (s, 1H), 7.36 (d, J=8.4 Hz, 1H), 7.19 (d, J=7.6 Hz, 1H), 7.11 (t, J=7.6 Hz, 1H), 7.06 (s, 1H), 7.01-6.95 (m, 1H), 4.41 (m, 1H), 4.16-4.11 (m, 3H), 3.86 (s, 3H), 3.18-3.08 (m, 1H), 3.05-2.94 (m, 1H), 2.88-2.77 (m, 1H), 2.40-2.30 (m, 1H), 2.09-2 (m, 1H). MS-ESI calculated value [M+H]$^+$ 405, measured value 405.

Example 41

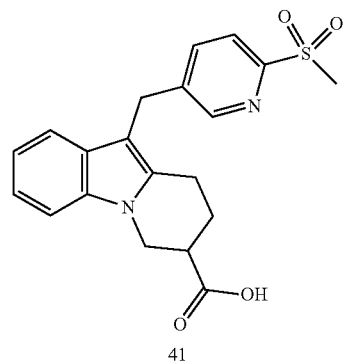

Step I

Compound 41 (32 mg) was synthesized from Compound 39a and Compound 41a according to the synthesis method in Example 7. $^1$H NMR (400 MHz, CDCl$_3$) δ8.63 (d, J=1.6 Hz, 1H), 7.93 (d, J=8.0 Hz, 1H), 7.70 (dd, J=1.6 Hz, J=8.0 Hz, 1H), 7.38-7.33 (m, 2H), 7.23-7.19 (m, 1H), 7.13-7.11 (m, 1H), 4.45-4.41 (m, 1H), 4.21-4.15 (m, 3H), 3.19 (s, 3H), 3.15-3.05 (m, 2H), 2.90-2.87 (m, 1H), 2.42-2.40 (m, 1H), 2.11-2.09 (m, 1H). MS-ESI calculated value [M+H]$^+$ 385, measured value 385.

Example 42

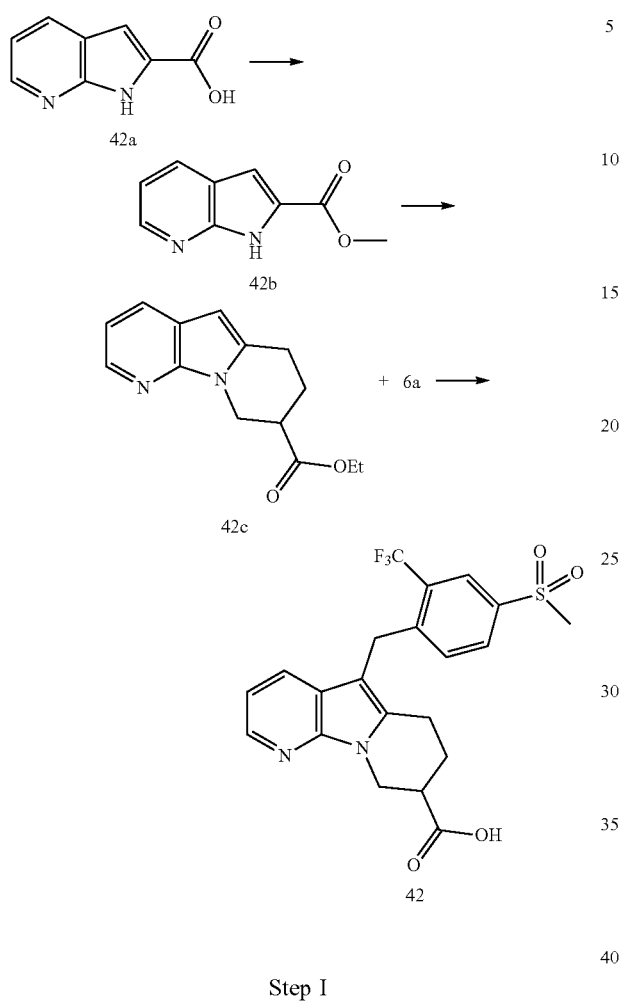

Step I

Sulfur dichloride (33.02 g, 277.52 mmol) was added to a solution of Compound 42a (30.00 g, 185.01 mmol) in methanol (250 mL). The resulting reaction mixture was heated to 80° C., and stirred for 16 hr. After completion of the reaction, the reaction mixture was concentrated to dryness, slurried in ethyl acetate (200 mL), and filtered, to give Compound 42b (31.60 g). $^1$H NMR (400 MHz, CD$_3$OD) δ8.87-8.85 (m, 1H), 8.61-8.59 (m, 1H), 7.67 (m, 1H), 7.54 (s, 1H), 4.01 (s, 3H). MS-ESI calculated value [M+H]$^+$ 177, measured value 177.

Step II

Compound 42c (390 mg) was obtained from Compound 42b via a multi-step reaction according to the synthesis method in Example 34. MS-ESI calculated value [M+H]$^+$ 245, measured value 245.

Step III

Compound 42 (5 mg) was synthesized from Compound 42c and Compound 6a according to the synthesis method of Compound 7. $^1$H NMR (400 MHz, CD$_3$OD) δ8.38-8.36 (m, 1H), 8.30 (s, 1H), 8.26 (d, J=7.6 Hz, 1H), 8.03-7.98 (m, 1H), 7.53-7.47 (m, 1H), 7.33 (d, J=8.4 Hz, 1H), 4.63 (m, 1H), 4.49 (m, 1H), 4.47 (s, 2H), 3.16 (s, 3H), 3.11-2.94 (m, 2H), 2.66 (s, 1H), 2.41 (m, 1H), 2.16 (m, 1H). MS-ESI calculated value [M+H]$^+$ 453, measured value 453.

Example 43

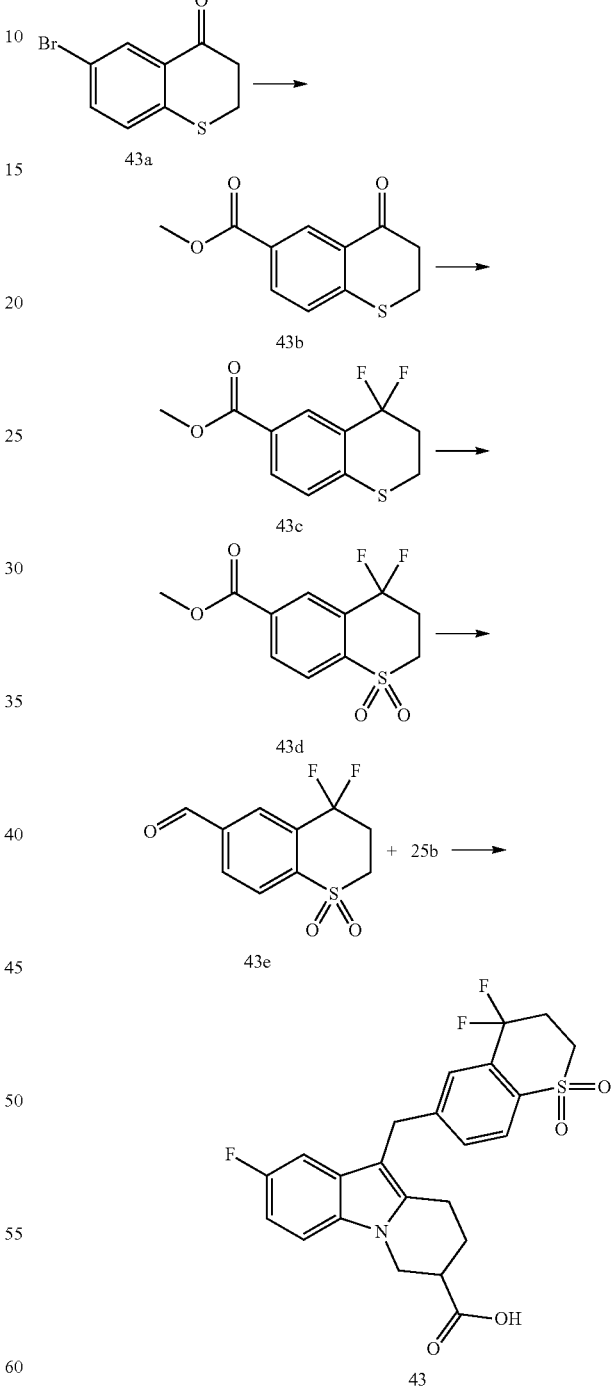

Step I

Compound 43b (7.80 g) was obtained from Compound 43a according to the synthesis method in Example 33. $^1$H NMR (400 MHz, CDCl$_3$) δ8.75 (s, 1H), 8.03-8.00 (dd, J=6.0 Hz, J=8.0 Hz, 1H), 7.37-7.35 (d, J=8.0 Hz, 1H), 3.93 (s, 3H), 3.32-3.28 (m, 2H), 3.04-3.00 (m, 2H).

Step II

Compound 43b (7.00 g, 31.49 mmol) was slowly added in batch to bis(2-methoxyethyl)aminosulfur trifluoride (35 mL). The resulting reaction mixture was stirred for 4 hr at 90° C. After completion of the reaction, the reaction mixture was cooled to the room temperature, and diluted with dichloromethane (40 mL). The resulting reaction mixture was slowly added to a saturated aqueous solution of sodium bicarbonate (100 mL) at 0° C. to quench the reaction. The resulting mixture was extracted with dichloromethane (50 mL×2). The organic phases were combined, washed with saturated brine (100 mL×1), dried over anhydrous sodium sulfate, filtered, and concentrated under reduced pressure. The resulting residue was separated and purified by silica gel column chromatography (petroleum ether/ethyl acetate=100-0%), to give Compound 43c (5.80 g). $^1$H NMR (400 MHz, CDCl$_3$) δ8.38 (s, 1H), 7.94-7.91 (m, 1H), 7.25-7.23 (m, 1H), 3.93 (s, 3H), 3.22-3.19 (m, 2H), 2.65-2.54 (m, 2H).

Step III

Compound 43c (5.56 g, 22.93 mmol) was dissolved in dichloromethane (60 mL), and m-chloroperoxybenzoic acid (9.31 g, 45.85 mmol, 85%) was added at 0° C. The resulting reaction mixture was stirred for 3 hr at 25° C. After completion of the reaction, the reaction mixture was filtered. A saturated solution of sodium thiosulfate (20 mL) was added to the filtrate to quench the reaction. The organic phase was washed with a saturated aqueous solution of sodium bicarbonate (50 mL), dried over anhydrous sodium sulfate, filtered, and concentrated under reduced pressure. The resulting residue was separated and purified by silica gel column chromatography (petroleum ether/ethyl acetate=100-0%), to give Compound 43d (4.40 g). $^1$H NMR (400 MHz, CDCl$_3$) δ8.47 (s, 1H), 8.36-8.34 (m, 1H), 8.05-8.03 (m, 1H), 4.00 (s, 3H), 3.65-3.62 (m, 2H), 3.12-3.06 (m, 2H).

Step IV

Compound 43e (3.70 g) was obtained from Compound 43d according to the synthesis method in Example 33. $^1$H NMR (400 MHz, CDCl$_3$) δ10.14 (s, 1H), 8.31 (s, 1H), 8.23-8.21 (m, 1H), 8.15-8.13 (m, 1H), 3.68-3.64 (m, 2H), 3.12-3.06 (m, 2H).

Step V

Compound 43 (37 mg) was synthesized from Compound 43e and Compound 25b via a multi-step reaction according to the synthesis method in Example 7. $^1$H NMR (400 MHz, CD$_3$OD) δ7.79-7.76 (m, 1H), 7.64 (s, 1H), 7.57-7.54 (m, 1H), 7.31-7.28 (m, 1H), 6.99-6.96 (m, 1H), 6.89-6.82 (m, 1H), 4.39-4.34 (m, 1H), 4.21-4.07 (m, 3H), 3.68-3.62 (m, 2H), 3.15-2.94 (m, 4H), 2.89-2.79 (m, 1H), 2.37-2.30 (m, 1H), 2.07-1.96 (m, 1H). MS-ESI calculated value [M+H]$^+$ 464, measured value 464.

Example 44

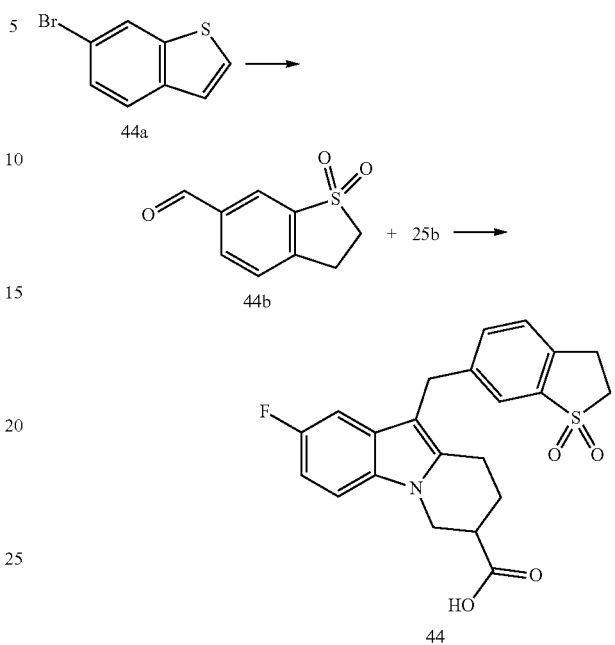

Step I

Compound 44b (180 mg) was obtained from Compound 44a according to the synthesis method in Example 38. $^1$H NMR (400 MHz, CDCl$_3$) δ10.06 (s, 1H), 8.23 (s, 1H), 8.13-8.10 (m, 1H), 7.58-7.56 (m, 1H), 3.60-3.56 (m, 2H), 3.51-3.48 (m, 2H).

Step II

Compound 44 (36 mg) was synthesized from Compound 44b and Compound 25b according to the synthesis method of Compound 7. $^1$H NMR (400 MHz, CD$_3$OD) δ7.54-7.44 (m, 2H), 7.37-7.35 (m, 1H), 7.32-7.28 (m, 1H), 6.99-6.96 (m, 1H), 6.88-6.83 (m, 1H), 4.40-4.35 (m, 1H), 4.16-4.06 (m, 3H), 3.54-3.48 (m, 2H), 3.36-3.34 (m, 2H), 3.14-3.02 (m, 2H), 2.93-2.81 (m, 1H), 2.40-2.30 (m, 1H), 2.05-1.95 (m, 1H). MS-ESI calculated value [M+H]$^+$ 414, measured value 414.

Biological Activity Assay

Experimental Method:

DiscoverX Corporation in the U.S was entrusted to complete this experiment by β-arrestin assay. The experimental method and results were listed below: PathHunter® CHO-K1 CRTH2 β-arrestin cells (DiscoverX, catalogue number 93-0291C$_2$) grew under standard conditions, and were inoculated into a white-wall 384-well microplate at a density of 5,000 cells/well. 20 μL of Cell Plating Reagent 1 was used in each well. Before the test, the cells were incubated overnight at 37° C./5% CO$_2$. A test compound was serially diluted in DMSO with a dilution factor of 3-fold to give 8 concentrations of the test compound. Shortly before the test, the serially diluted test compound was further diluted with the test buffer to 5 times of the test concentration. 5 μL of the further diluted test compound was added to the cells, and the cells were incubated for 30 min at 37° C. The concentration of the solvent was 1%. 5 μL of 6× EC$_{80}$ agonist (PGD2) buffer was added to the cells, and the cells were incubated for 90 min at 37° C. Measured signals were generated by one-time addition of 15 μL (50% v/v) of PathHunter detection mixture reagent and subsequent one-hour incubation. The microplate was read through the chemiluminescent signals of PerkinElmer Envision™ reader. Biological activity of the test compound was analyzed by CBIS data analysis suite (ChemInnovation, CA), and was denoted as IC$_{50}$ value. The experimental results were shown in Table 1.

TABLE 1

| Compound | IC$_{50}$ |
|---|---|
| Example 1 | + |
| Example 2 | ++ |
| Example 6 | ++ |
| Example 7 | + |
| Example 8 | + |
| Example 9 | + |
| Example 10 | + |
| Example 11 | + |
| Example 15 | + |
| Example 16 | +++ |
| Example 16 peak1 | + |
| Example 16 peak2 | +++ |
| Example 17 | ++ |
| Example 18 | + |
| Example 20 | + |
| Example 21 | + |
| Example 22 | +++ |
| Example 22 peak1 | +++ |
| Example 22 peak2 | + |
| Example 23 | ++ |
| Example 24 | + |
| Example 25 | +++ |
| Example 25 peak1 | ++ |
| Example 25 peak2 | +++ |
| Example 26 | ++ |
| Example 27 | + |
| Example 28 | + |
| Example 29 | + |
| Example 30 | + |
| Example 31 | + |
| Example 32 | ++ |
| Example 33 | + |
| Example 34 | +++ |
| Example 35 | +++ |
| Example 36 | + |
| Example 37 | + |
| Example 38 | + |
| Example 39 | + |
| Example 40 | + |
| Example 41 | + |
| Example 42 | + |
| Example 43 | + |
| Example 44 | + |

Note:
+>1.0 μM;
++0.1-1.0 μM;
+++<0.1 μM;

Conclusion: The compounds of the present application have a strong antagonistic effect on a CRTH2 receptor.

What is claimed is:

1. A compound represented by formula (I), a pharmaceutically acceptable salt, tautomer, stereoisomer, or solvate thereof,

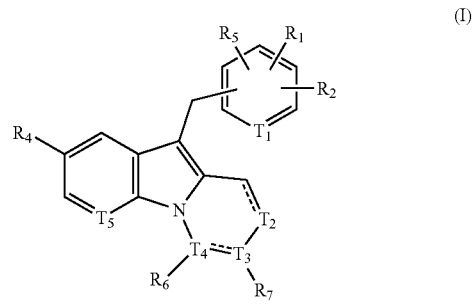

wherein
T$_1$ is selected from the group consisting of N and CH;
T$_2$ is selected from the group consisting of a single bond, N, NH, CH$_2$, and CH;
T$_3$ and T$_4$ are each independently selected from the group consisting of C, CR$_3$, and N;
T$_5$ is selected from the group consisting of N and CH;
R$_1$ and R$_2$ together with the ring-forming atoms they are attached to form a 5- to 6-membered ring, which is optionally substituted with 1, 2, or 3 R;
one of R$_6$ and R$_7$ is -L-COOH, and the other is selected from the group consisting of H and C$_{1-3}$ alkyl optionally substituted with 1, 2, or 3 R;
L is selected from the group consisting of a single bond and —CH$_2$—;
R$_3$ is selected from the group consisting of H and C$_{1-3}$ alkyl optionally substituted with 1, 2, or 3 R;
R$_4$ is selected from the group consisting of H, halogen, —OH, and —NH$_2$; or is selected from the following groups: C$_{1-3}$ alkyl and C$_{1-3}$ alkoxy, wherein the C$_{1-3}$ alkyl and C$_{1-3}$ alkoxy are optionally substituted with 1, 2, or 3 R;
R$_5$ is selected from the group consisting of H and the following groups: C$_{1-3}$ alkyl and C$_{1-3}$ alkoxy, wherein the C$_{1-3}$ alkyl and C$_{1-3}$ alkoxy are optionally substituted with 1, 2, or 3 R;
each R is independently selected from the group consisting of F, Cl, Br, I, —CN, —OH, and —COOH; or is independently selected from the following groups which are optionally substituted with 1, 2, or 3 R': —NH$_2$, C$_{1-6}$ alkyl, C$_{3-6}$ cycloalkyl, 3- to 6-membered heterocycloalkyl, phenyl, and 5- to 6-membered heteroaryl; and
each R' is independently selected from the group consisting of F, Cl, Br, I, —OH, —CN, —NH$_2$, —COOH, Me, Et, —CF$_3$, —CHF$_2$, —CH$_2$F, —NHCH$_3$, and —N(CH$_3$)$_2$.

2. The compound according to claim 1, wherein each R is independently selected from the group consisting of F, Cl, Br, I, —CN, —OH, and —COOH; or is independently selected from the group consisting of —NH$_2$ and C$_{1-4}$ alkyl, wherein the —NH$_2$ and C$_{1-4}$ alkyl are optionally substituted with 1, 2, or 3 R'.

3. The compound according to claim 1, wherein R$_5$ is selected from the group consisting of H, —CF$_3$, and MeO.

4. The compound according to claim 1, wherein R$_3$ is selected from the group consisting of H and Me.

5. The compound according to claim 1, wherein R$_4$ is selected from the group consisting of H, F, Cl, Br, I, —OH, —NH$_2$, methoxy, and difluoromethoxy.

6. The compound according to claim 1, wherein R$_1$ and R$_2$ together with the ring-forming atoms they are attached to form a benzene ring, a cyclobutyl sulfone ring, or a cyclopentyl sulfone ring, and wherein the benzene ring, the cyclobutyl sulfone ring, and the cyclopentyl sulfone ring are optionally substituted with 1, 2, or 3 R.

7. The compound according to claim 1, wherein when $R_1$ and $R_2$ together with the ring-forming atoms they are attached to form the 5- to 6-membered ring, the structural unit

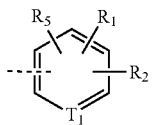

is selected from the group consisting of:

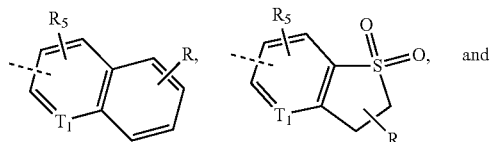

8. The compound according to claim 1, wherein each R is independently selected from the group consisting of F, Cl, Br, I, —CN, —OH, —NH$_2$, —COOH, Me, Et, —CF$_3$, —CHF$_2$, —CH$_2$F, —NHCH$_3$, —N(CH$_3$)$_2$,

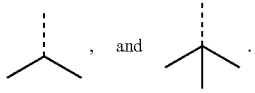

9. The compound according to claim 1, wherein when $R_1$ and $R_2$ together with the ring-forming atoms they are attached to form the 5- to 6-membered ring, the structural unit

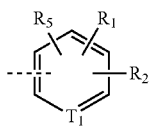

is selected from the group consisting of:

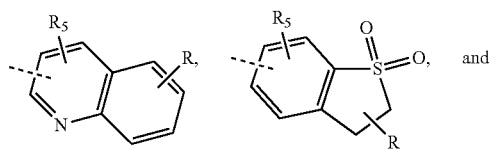

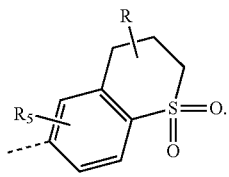

10. The compound according to claim 1, wherein when $R_1$ and $R_2$ together with the ring-forming atoms they are attached to form the 5- to 6-membered ring, the structural unit

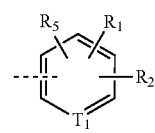

is selected from the group consisting of:

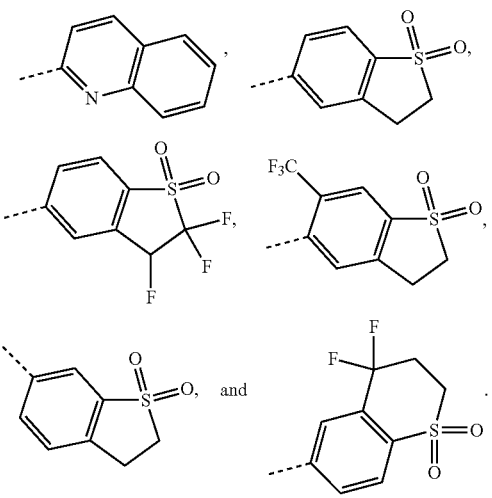

11. A compound, which is selected from the group consisting of:

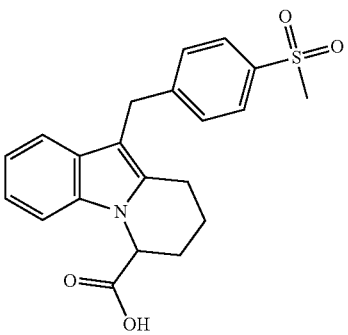

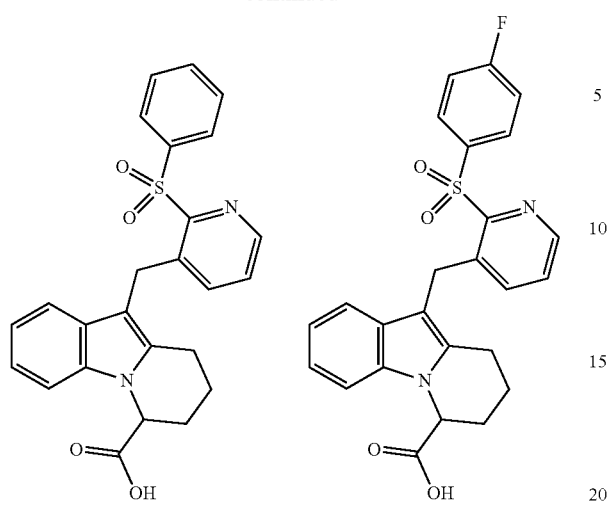
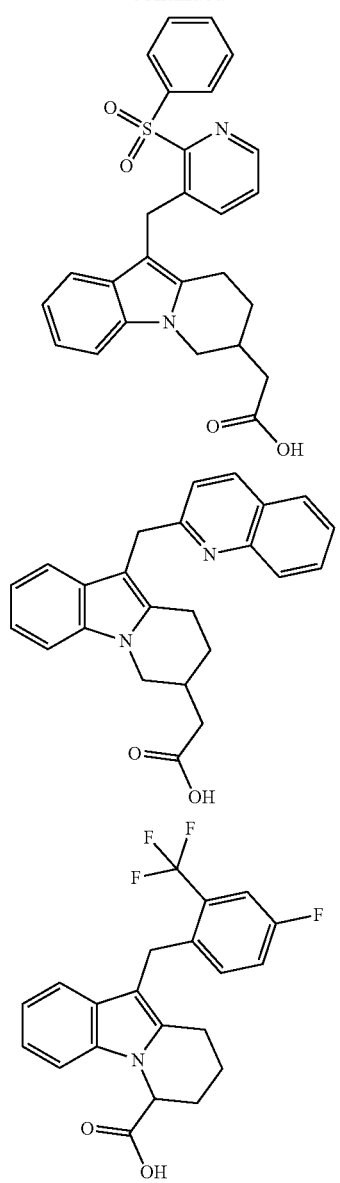

99
-continued
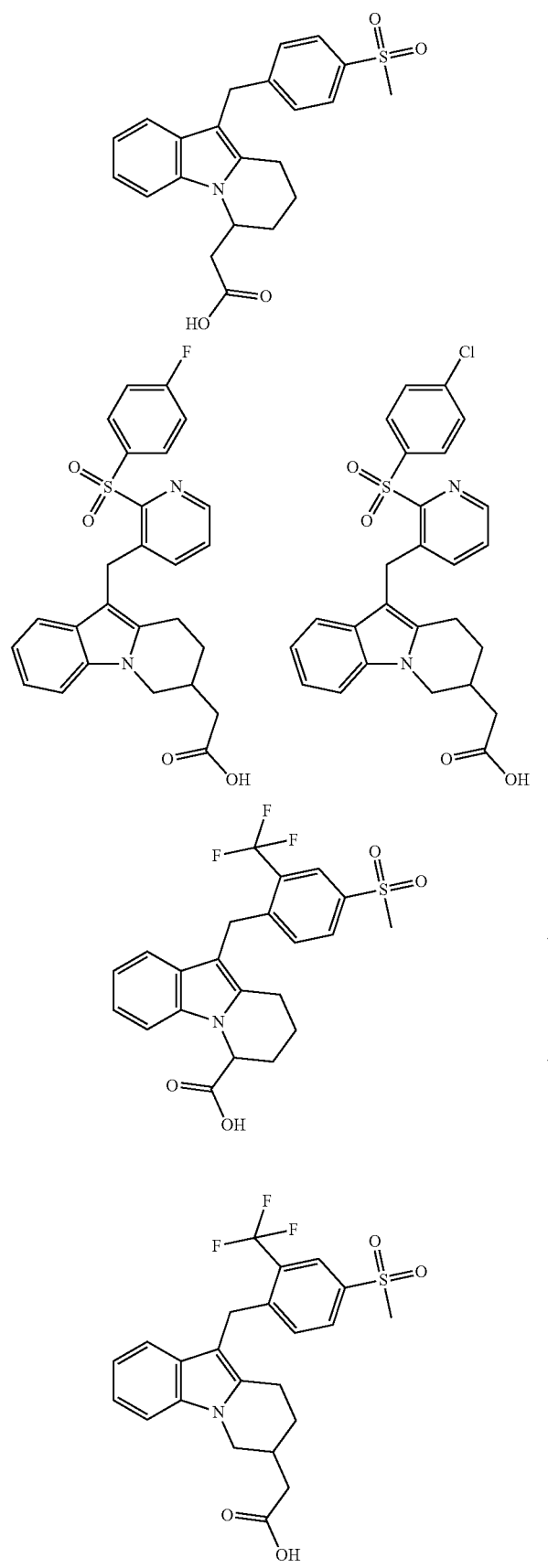
100
-continued
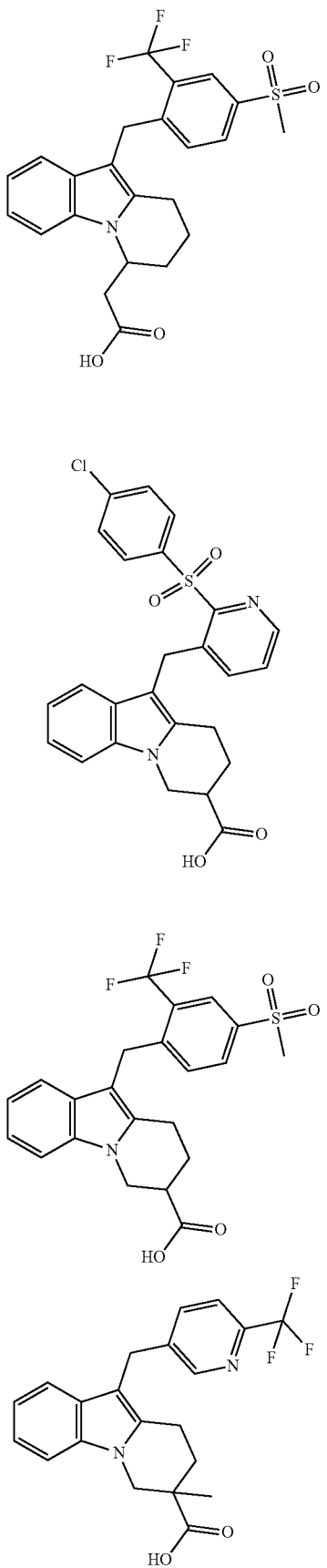

101
-continued
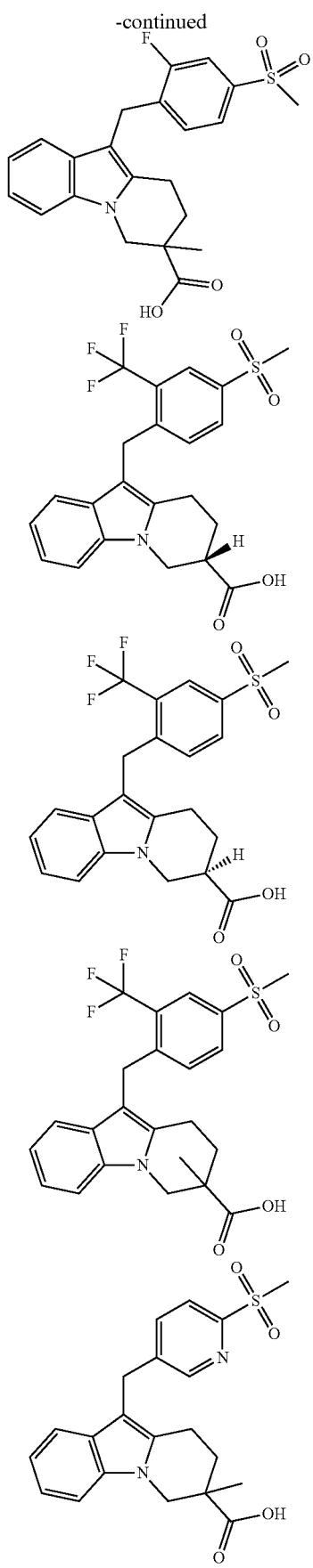
102
-continued
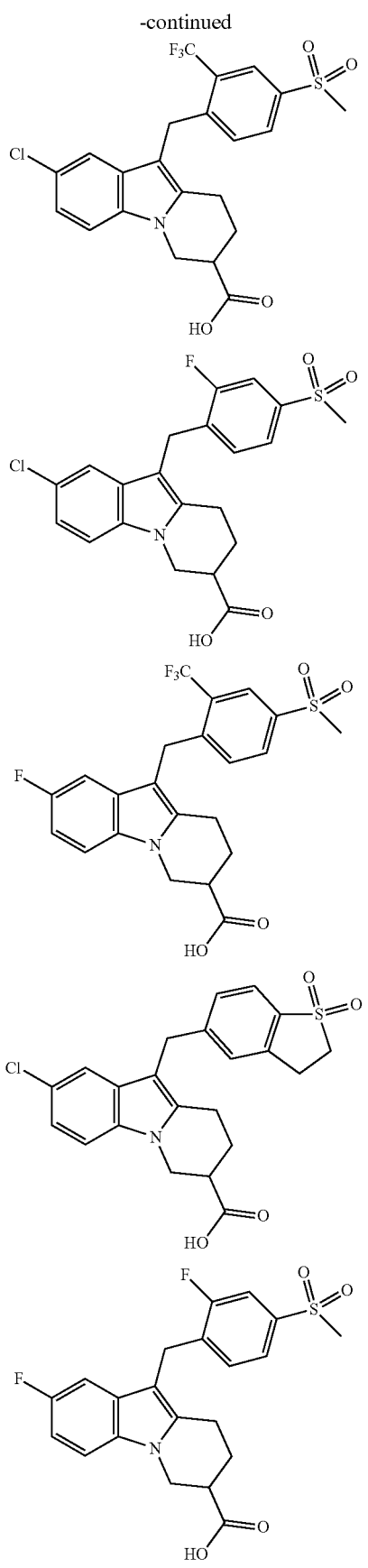

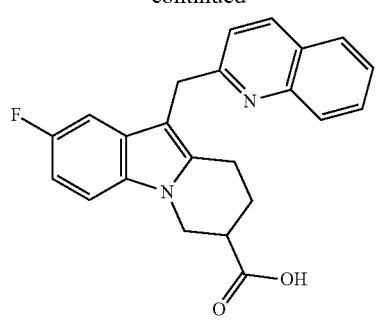
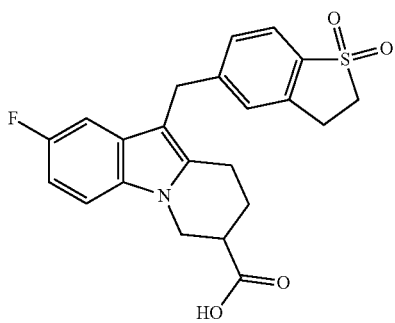
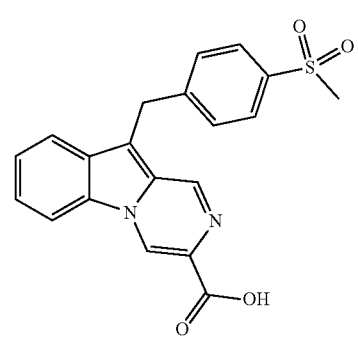
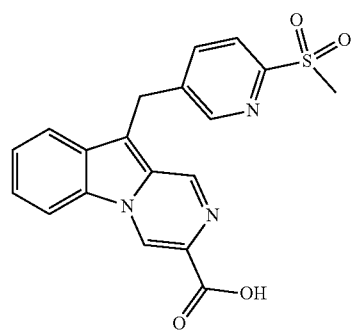
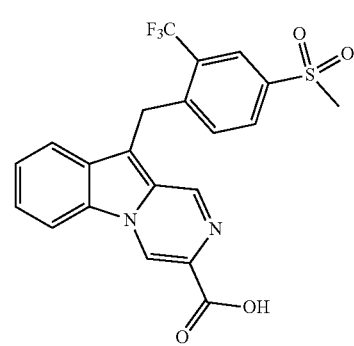
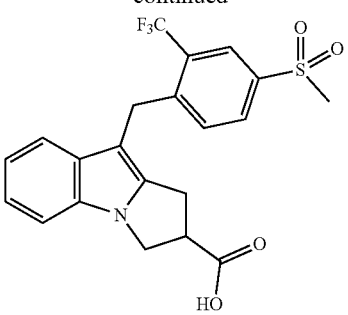
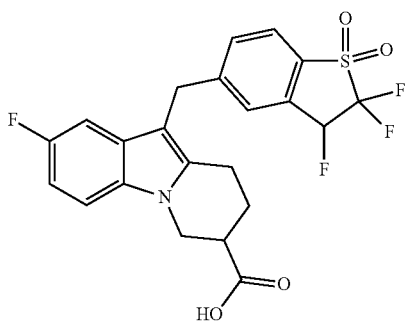
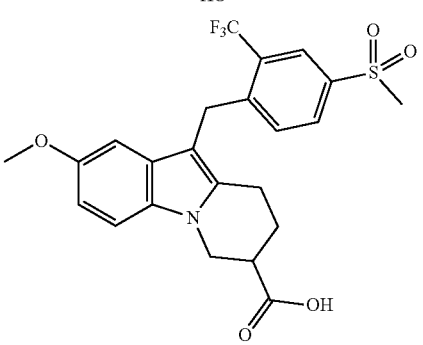
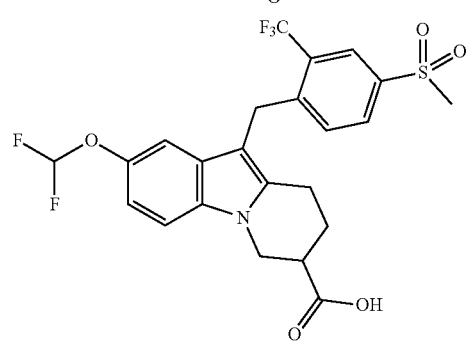
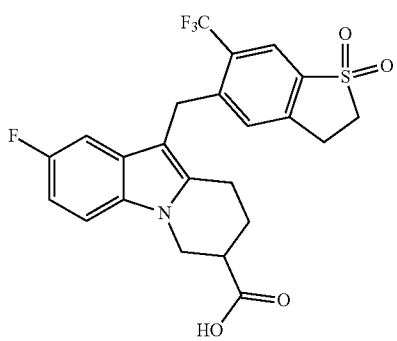

105
-continued
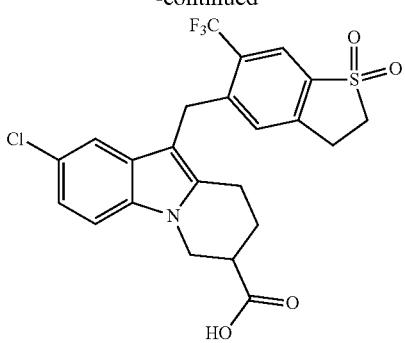
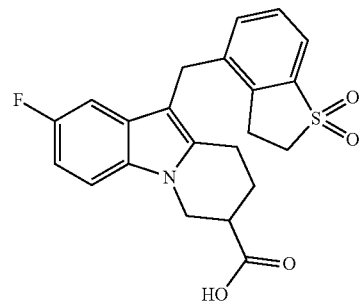
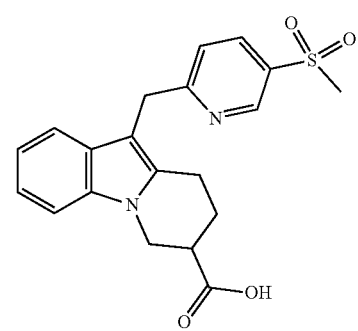
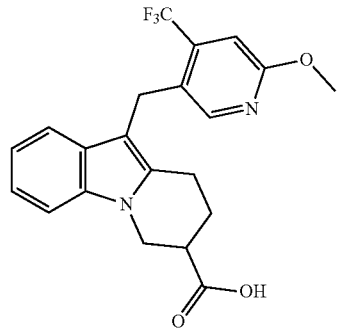
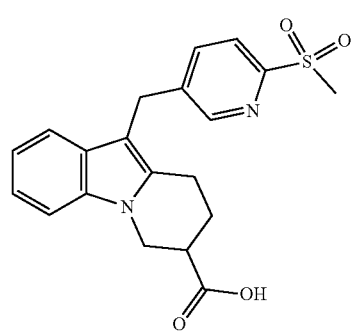
106
-continued
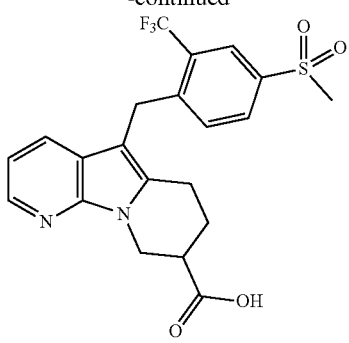
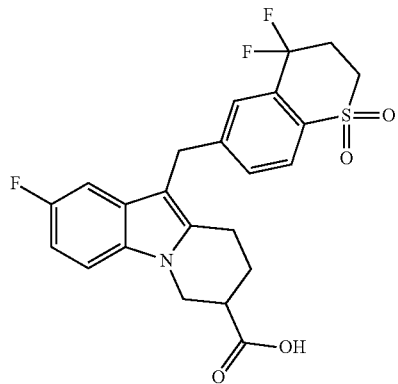
and
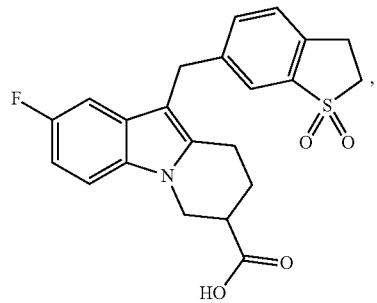
or a pharmaceutically acceptable salt, tautomer, stereoisomer, or solvate thereof.
12. A compound represented by formula (I), a pharmaceutically acceptable salt, tautomer, stereoisomer, or solvate thereof,
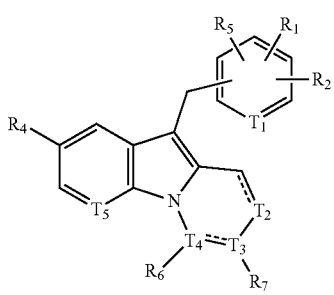
(I)
wherein
$T_2$ is selected from the group consisting of a single bond, N, NH, $CH_2$, and CH;

$T_3$ and $T_4$ are each independently selected from the group consisting of C, $CR_3$, and N;
$T_5$ is selected from the group consisting of N and CH;
wherein the structural unit

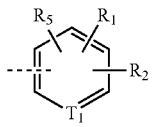

is selected from the group consisting of:

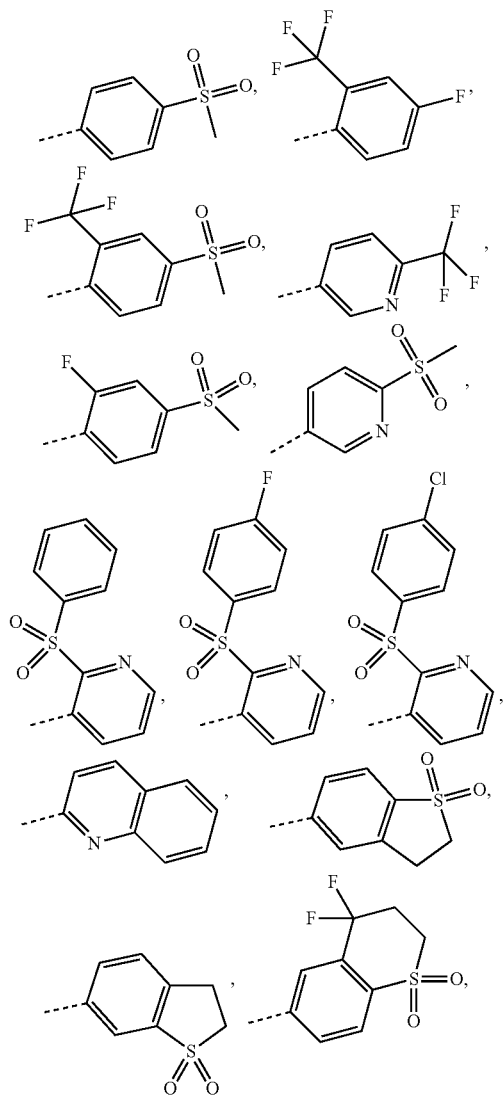

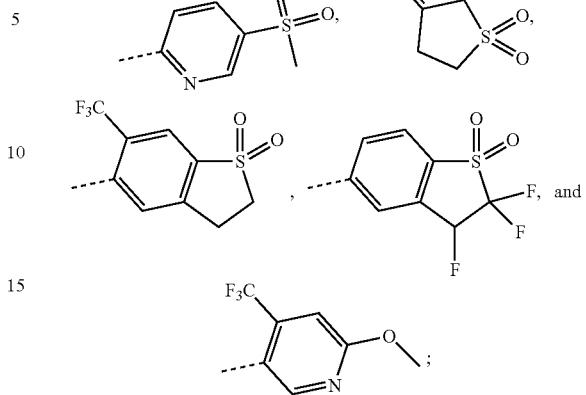

one of $R_6$ and $R_7$ is -L-COOH, and the other is selected from the group consisting of H and $C_{1-3}$ alkyl optionally substituted with 1, 2, or 3 R;

L is selected from the group consisting of a single bond and —$CH_2$—;

$R_3$ is selected from the group consisting of H and $C_{1-3}$ alkyl optionally substituted with 1, 2, or 3 R;

$R_4$ is selected from the group consisting of H, halogen, —OH, and —$NH_2$; or is selected from the following groups: $C_{1-3}$ alkyl and $C_{1-3}$ alkoxy, wherein the $C_{1-3}$ alkyl and $C_{1-3}$ alkoxy are optionally substituted with 1, 2, or 3 R;

each R is independently selected from the group consisting of F, Cl, Br, I, —CN, —OH, and —COOH; or is independently selected from the following groups which are optionally substituted with 1, 2, or 3 R': $C_{1-6}$ alkyl, $C_{3-6}$ cycloalkyl, 3- to 6-membered heterocycloalkyl, phenyl, and 5- to 6-membered heteroaryl; and each R' is independently selected from the group consisting of F, Cl, Br, I, —OH, —CN, —$NH_2$, —COOH, Me, Et, —$CF_3$, —$CHF_2$, —$CH_2F$, —$NHCH_3$, and —$N(CH_3)_2$.

13. A pharmaceutical composition, comprising the compound represented by formula (I) according to claim 1, or a pharmaceutically acceptable salt, tautomer, stereoisomer, or solvate thereof, and a pharmaceutically acceptable adjuvant.

14. A method for treating a disease mediated by a CRTH2 receptor in a mammal, comprising administering to a mammal in need thereof a therapeutically effective amount of the compound represented by formula (I) according to claim 1, or a pharmaceutically acceptable salt, tautomer, stereoisomer, or solvate thereof.

15. A method for treating a disease mediated by a CRTH2 receptor in a mammal, comprising administering to a mammal in need thereof a therapeutically effective amount of the pharmaceutical composition according to claim 13.

* * * * *